(12) United States Patent
Desimone et al.

(10) Patent No.: US 11,351,399 B2
(45) Date of Patent: **\*Jun. 7, 2022**

(54) COMBINED LOCAL DELIVERY OF THERAPEUTIC AGENTS USING INTERVENTIONAL DEVICES AND RADIATION

(71) Applicant: The University of North Carolina At Chapel Hill, Chapel Hill, NC (US)

(72) Inventors: Joseph Desimone, Chapel Hill, NC (US); Joel Tepper, Chapel Hill, NC (US); James Byrne, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/709,377

(22) Filed: Dec. 10, 2019

(65) Prior Publication Data

US 2021/0086000 A1    Mar. 25, 2021

Related U.S. Application Data

(63) Continuation of application No. 14/978,262, filed on Dec. 22, 2015, now Pat. No. 10,532,226.
(Continued)

(51) Int. Cl.
*A61N 5/10* (2006.01)
*A61N 1/05* (2006.01)
(Continued)

(52) U.S. Cl.
CPC .......... *A61N 5/1077* (2013.01); *A61M 5/007* (2013.01); *A61M 37/00* (2013.01); *A61N 1/0509* (2013.01);
(Continued)

(58) Field of Classification Search
CPC ...... A61N 5/1077; A61N 5/10; A61N 5/1007; A61N 1/0509; A61N 1/327; A61M 5/007; A61M 37/00
See application file for complete search history.

(56) References Cited

U.S. PATENT DOCUMENTS 10,532,226 B2 * 1/2020 Desimone ................ A61N 5/10
2003/0233136 A1  12/2003 Williams et al.
(Continued)

FOREIGN PATENT DOCUMENTS

WO   WO 2000/006243 A2   2/2000
WO   WO 2002/049501 A2   6/2002
(Continued)

OTHER PUBLICATIONS

Byrne, James D. et al.; "Local Iontophoretic Administration of Cytotoxic Therapies to Solid Tumors"; Science Translational Medicine; Feb. 4, 2015; vol. 7, Issue 273; pp. 1-11.
(Continued)

*Primary Examiner* — John P Lacyk
(74) *Attorney, Agent, or Firm* — Alston & Bird LLP

(57) ABSTRACT

A method and system for combination therapy utilizing local drug delivery and radiotherapy at a target site of body tissue are provided. The delivery system comprises a source electrode adapted to be positioned proximate to a target site of internal body tissue. A counter electrode is in electrical communication with the source electrode, and is configured to cooperate with the source electrode to form a localized electric field proximate to the target site. A cargo may be delivered to the target site when exposed to the localized electric field. Radiotherapy is applied to the target site in combination with the local drug delivery.

29 Claims, 48 Drawing Sheets

Related U.S. Application Data

(60) Provisional application No. 62/096,780, filed on Dec. 24, 2014.

(51) Int. Cl.
*A61M 5/00* (2006.01)
*A61M 37/00* (2006.01)
*A61N 1/32* (2006.01)

(52) U.S. Cl.
CPC .............. *A61N 1/327* (2013.01); *A61N 5/10* (2013.01); *A61N 5/1007* (2013.01); *A61M 2037/0007* (2013.01); *A61N 2005/1098* (2013.01)

(56) References Cited

U.S. PATENT DOCUMENTS

| | | |
|---|---|---|
| 2010/0016828 A1 | 1/2010 | Walker et al. |
| 2010/0261946 A1 | 10/2010 | Kaplan |
| 2011/0306878 A1 | 12/2011 | Desimone et al. |
| 2012/0259153 A1 | 10/2012 | Wang et al. |
| 2014/0121609 A1 | 5/2014 | de Juan, Jr. et al. |

FOREIGN PATENT DOCUMENTS

| | | |
|---|---|---|
| WO | WO 2009/110939 A2 | 9/2009 |
| WO | WO 2010/030995 A2 | 3/2010 |
| WO | WO 2010/099321 A1 | 9/2010 |

OTHER PUBLICATIONS

International Search Report and Written Opinion from corresponding International Patent Application No. PCT/IB2015/059898 dated May 19, 2016.
Lawrence, Theodore S. et al.; "The Mechanism of Action of Radiosensitization of Conventional Chemotherapeutic Agents"; Seminars in Radiation Oncology; vol. 13, No. 1; Jan. 2003; pp. 13-21.
European Search Report corresponding to Patent Application No. 15872073.0 dated Sep. 9, 2018; 4 pages.
Office Action for European Application No. 15872073.0 dated Sep. 21, 2018; 4 pages.

\* cited by examiner

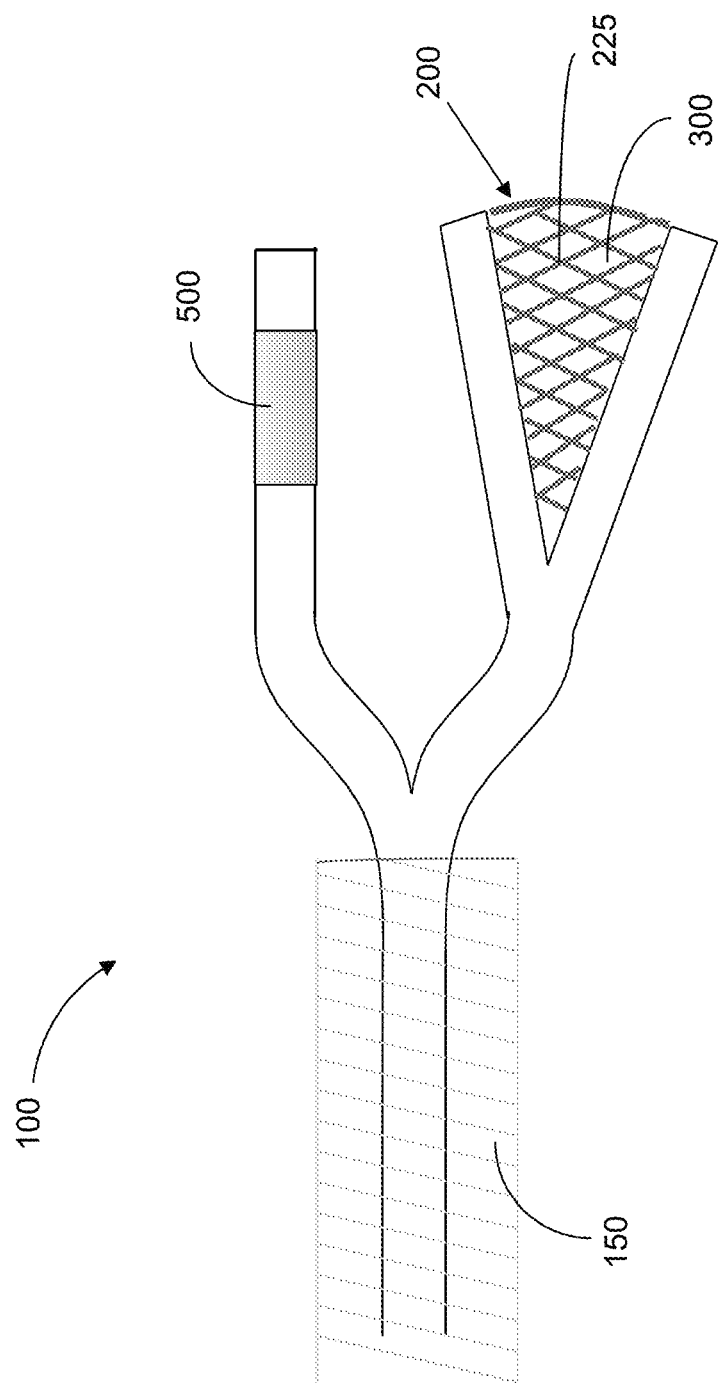

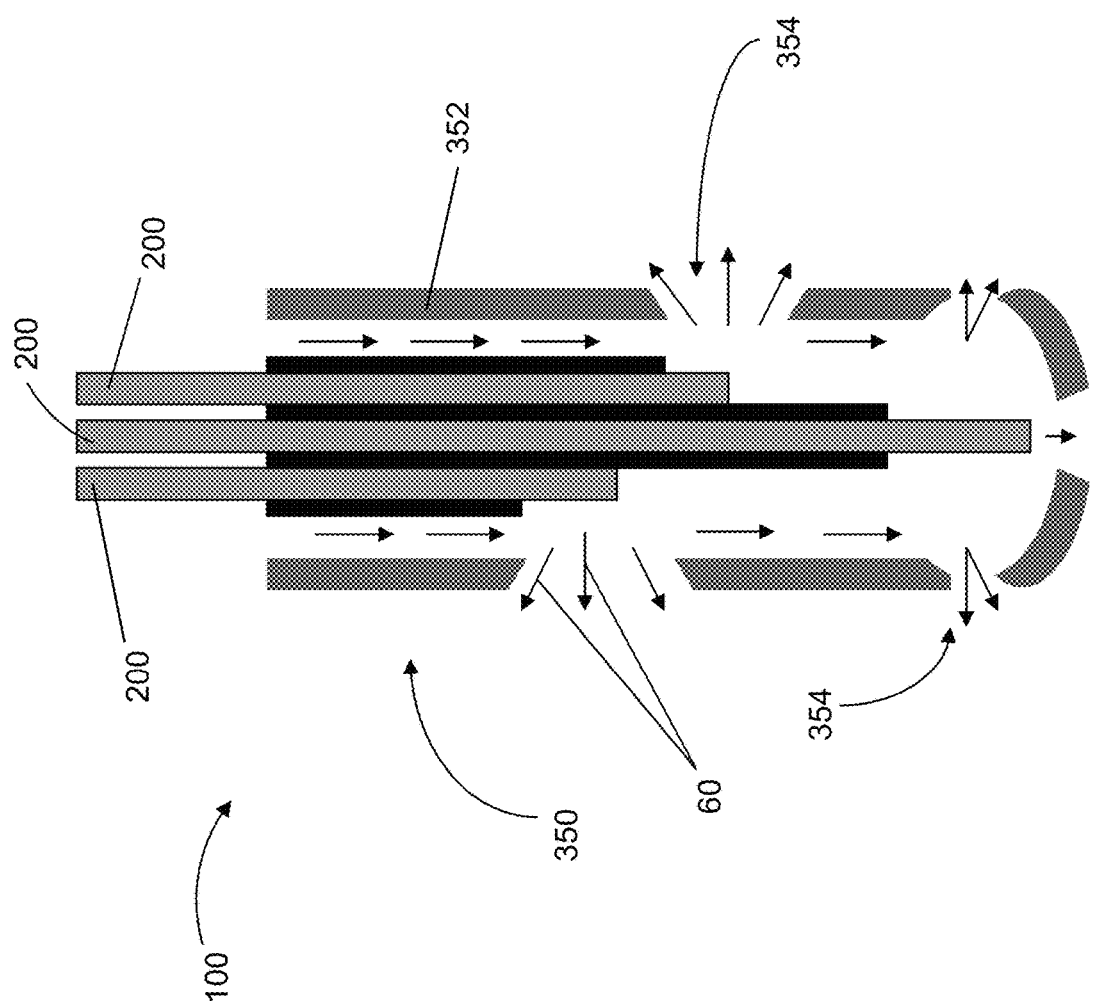

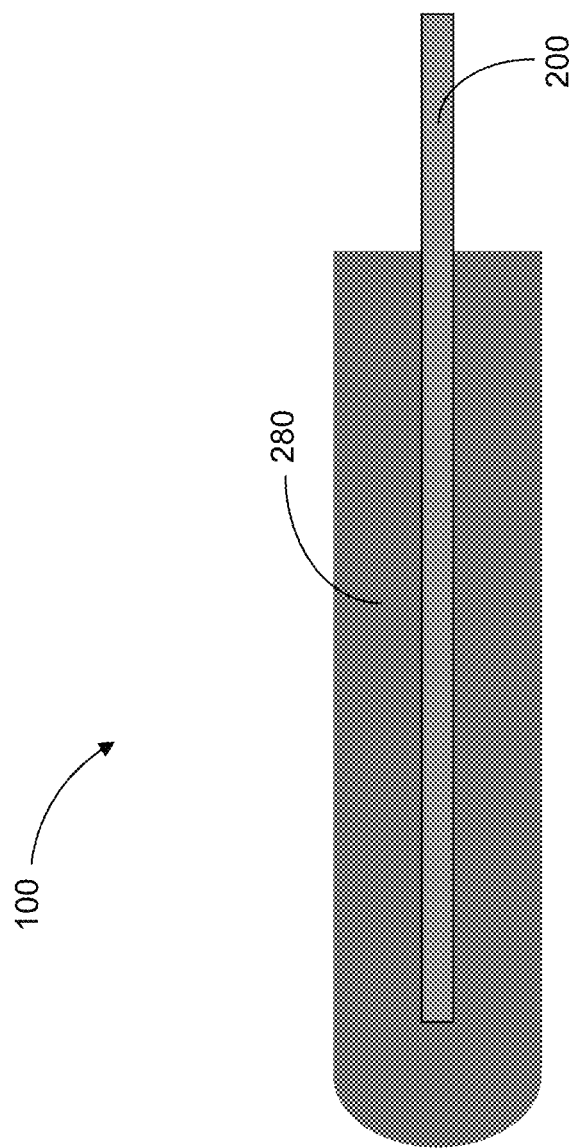

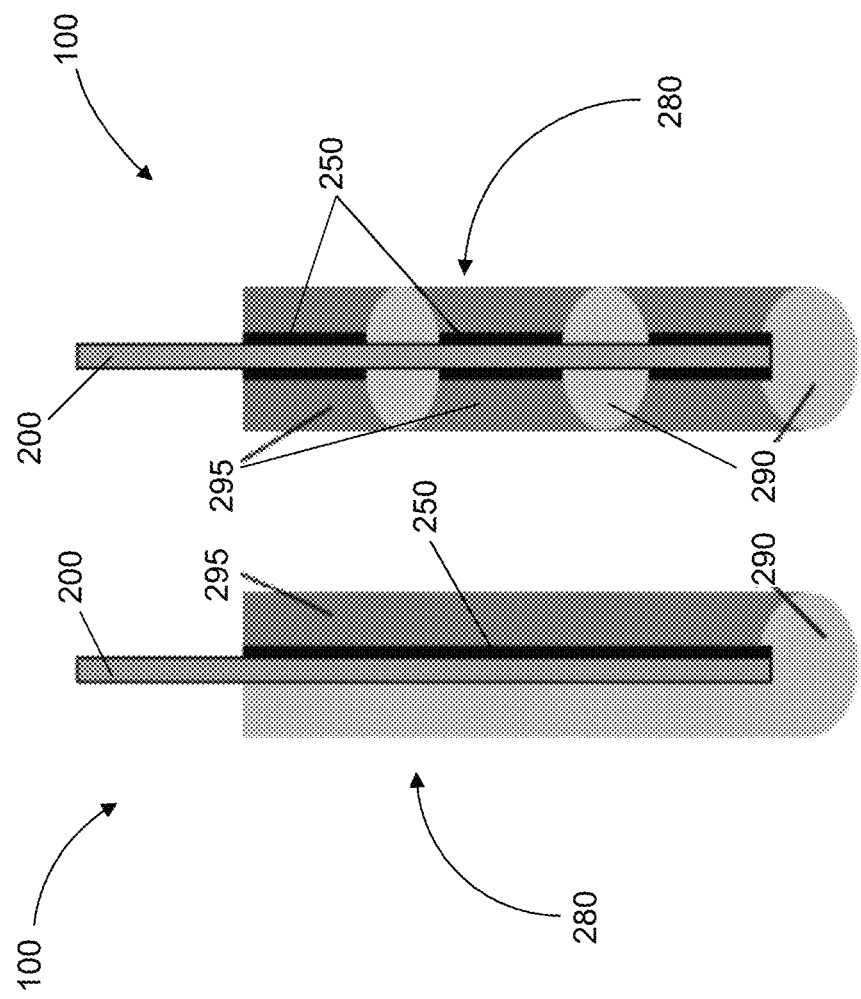

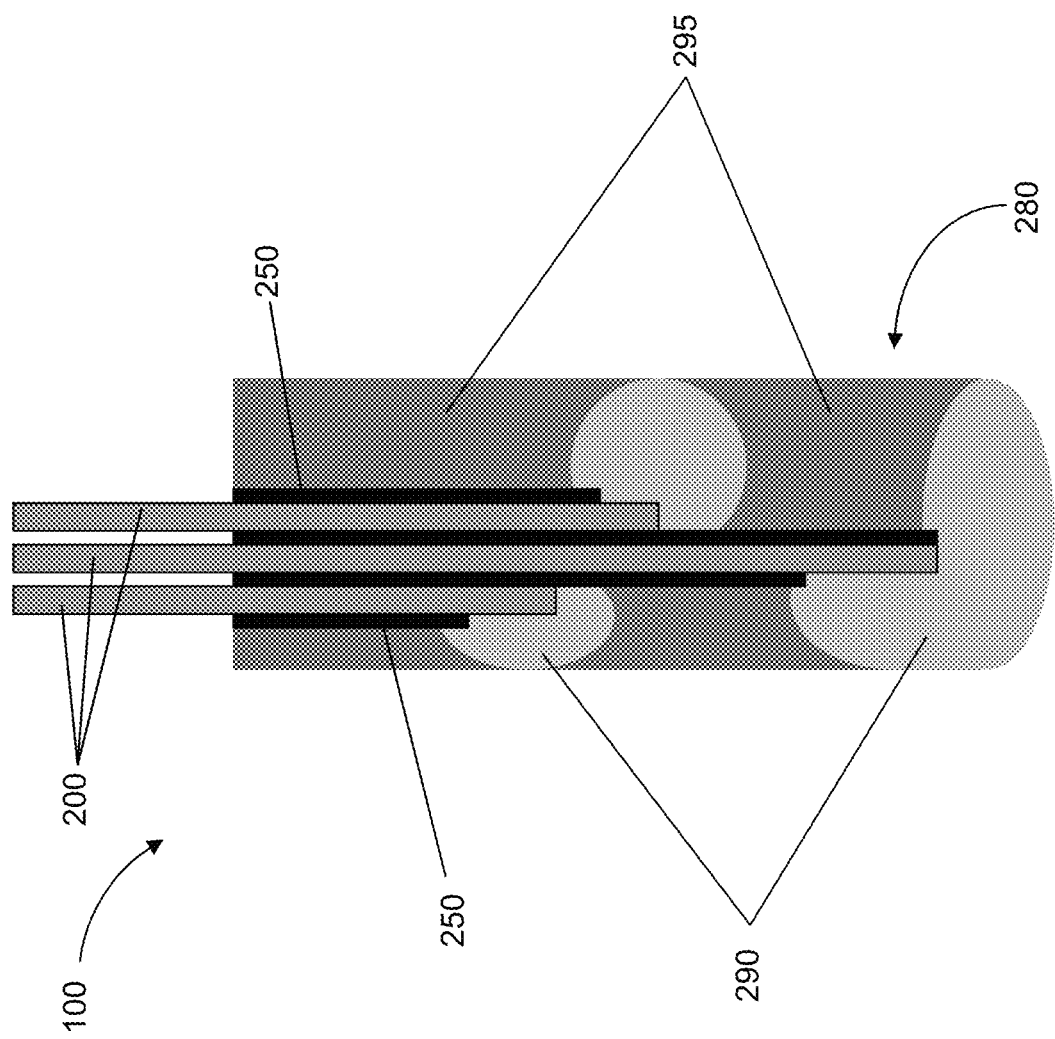

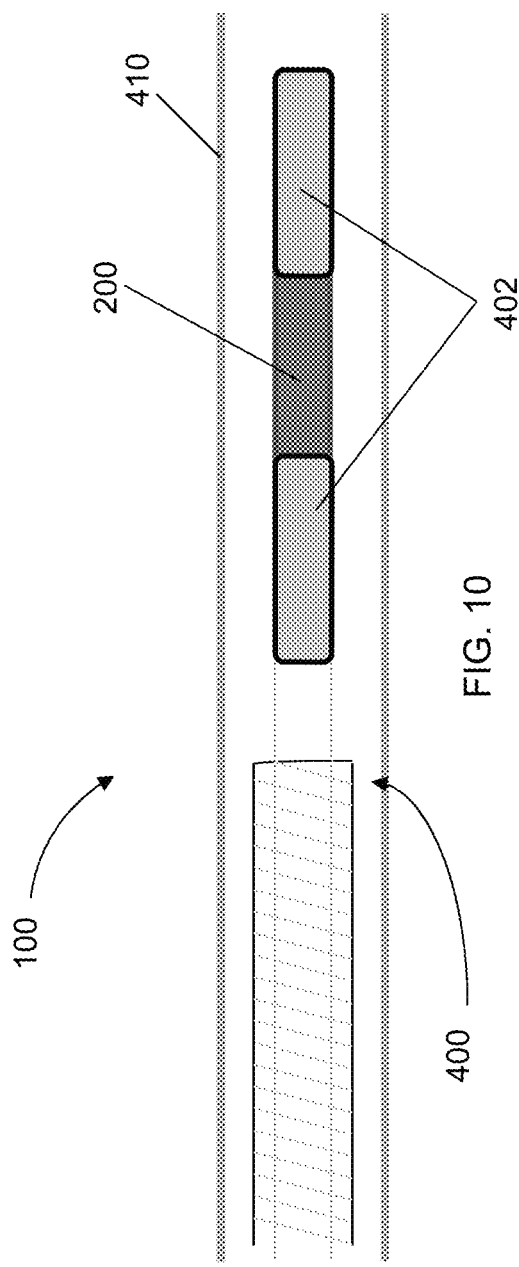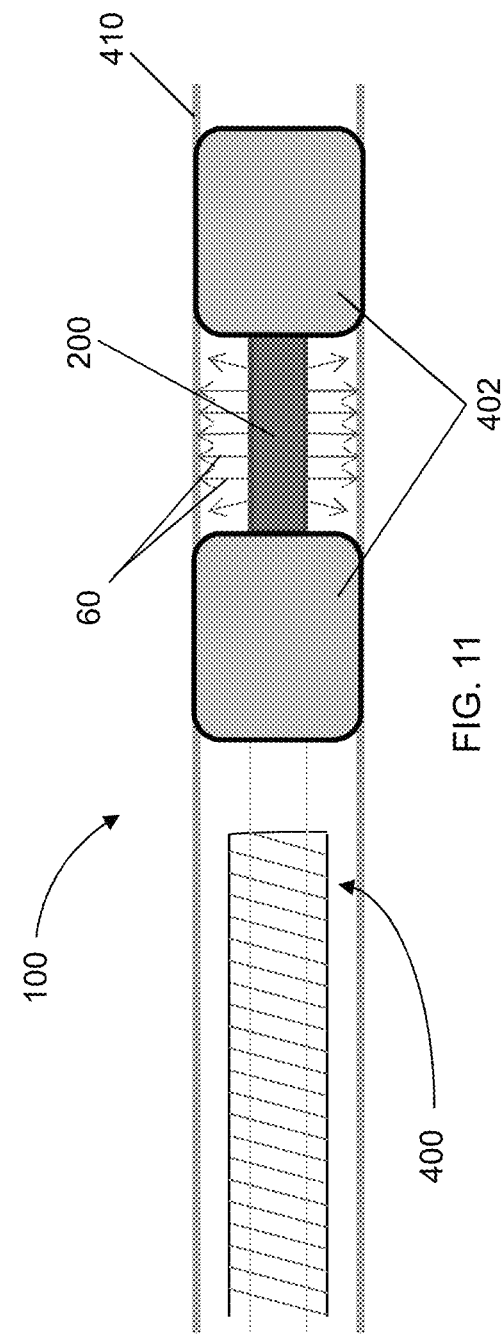

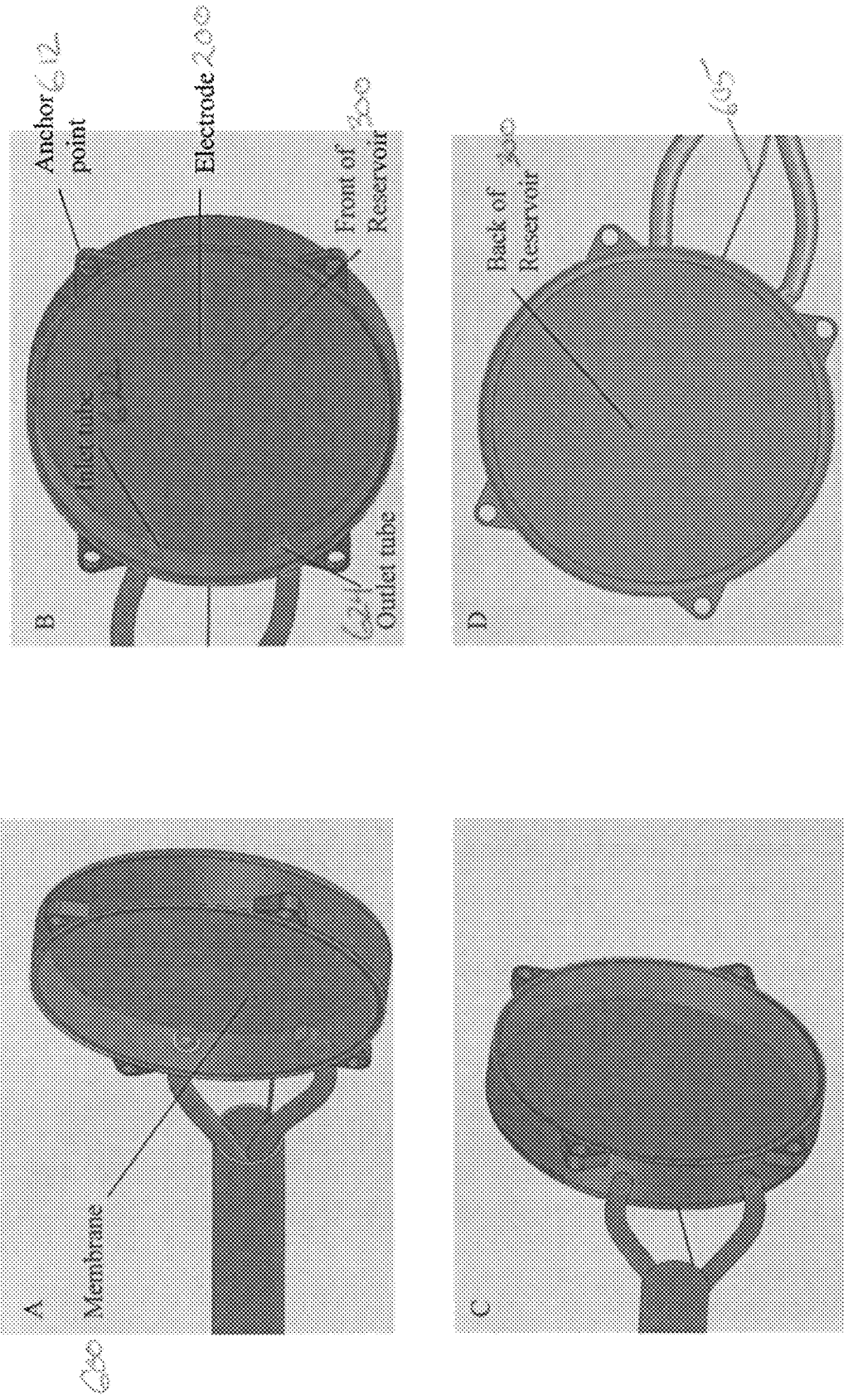
FIGS. 20A-D

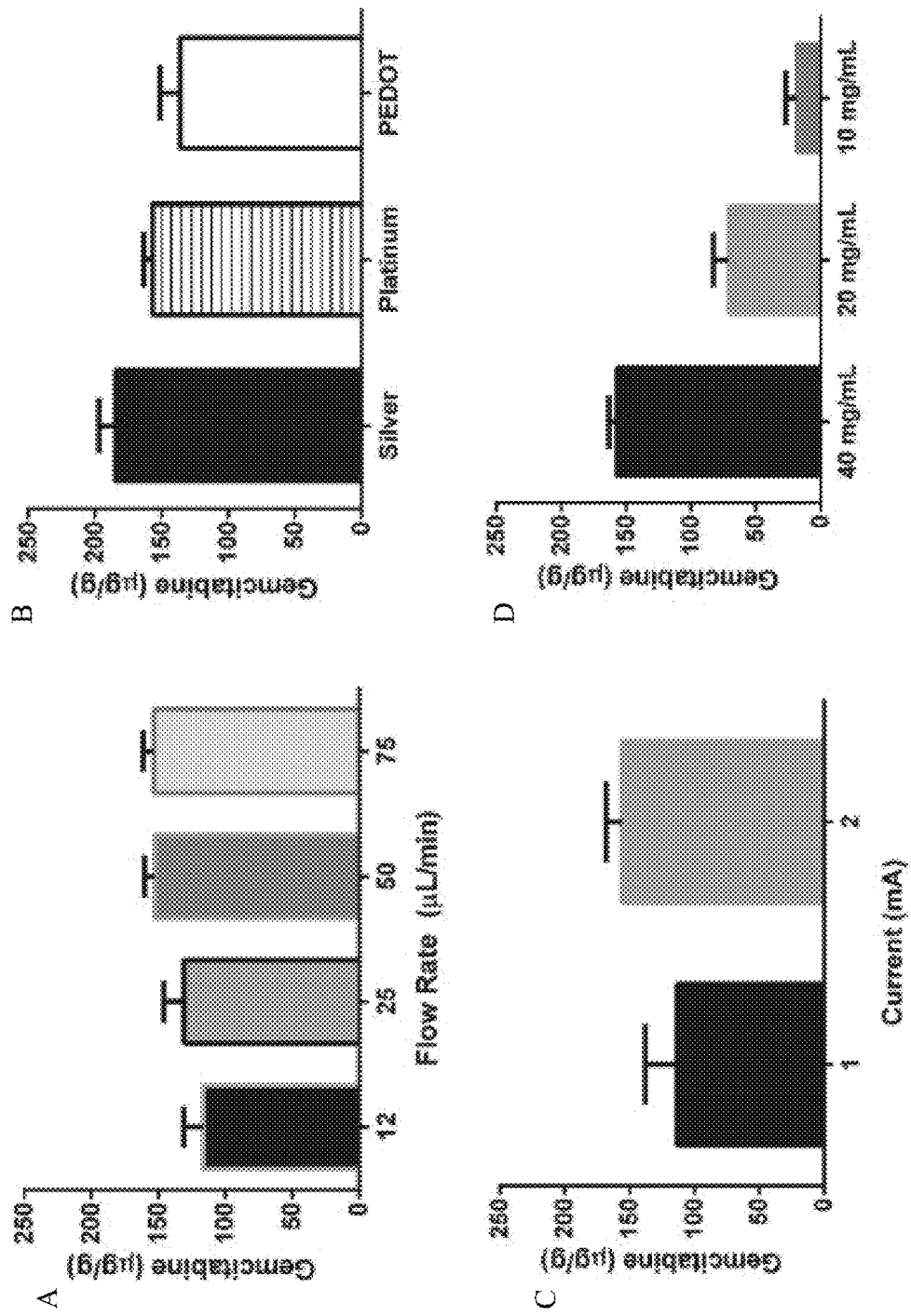
FIGS. 21A-D

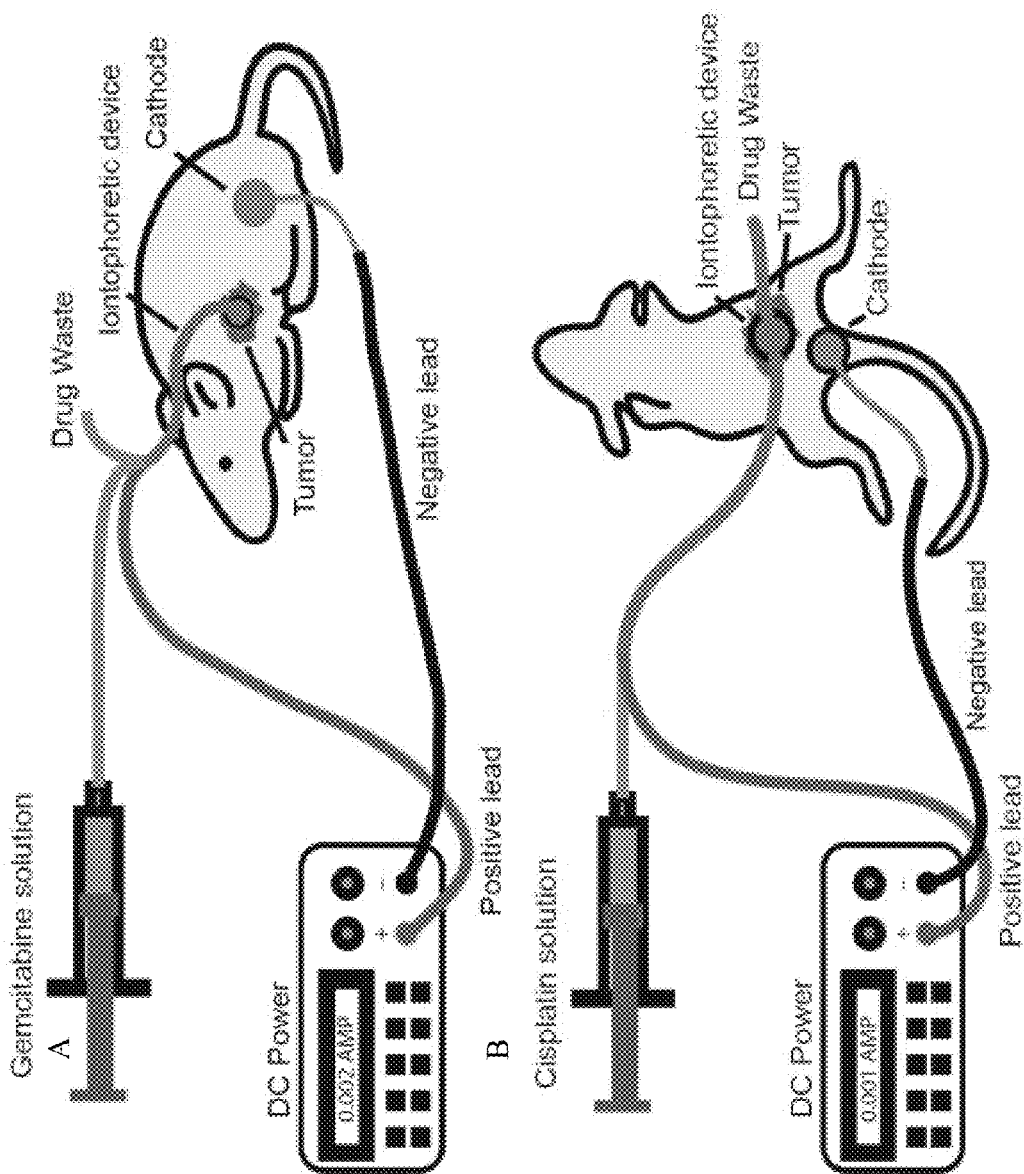
FIGS. 22A-B

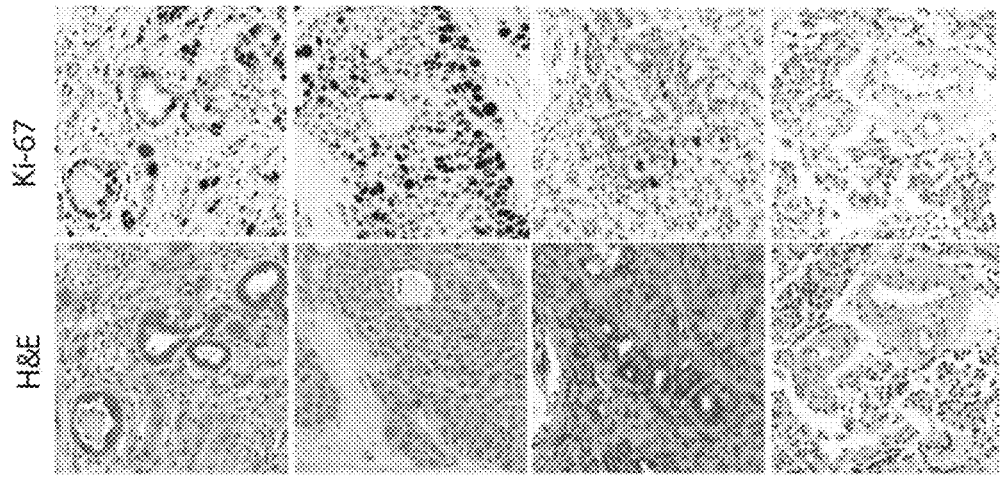
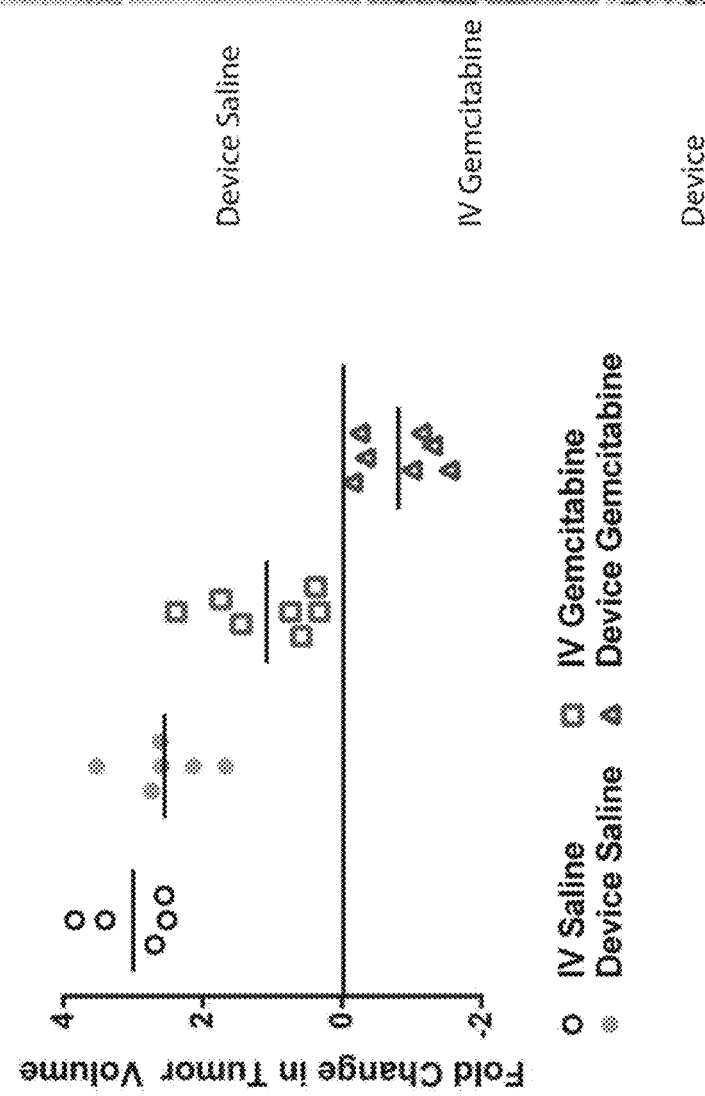
FIG. 32B
FIG. 32A

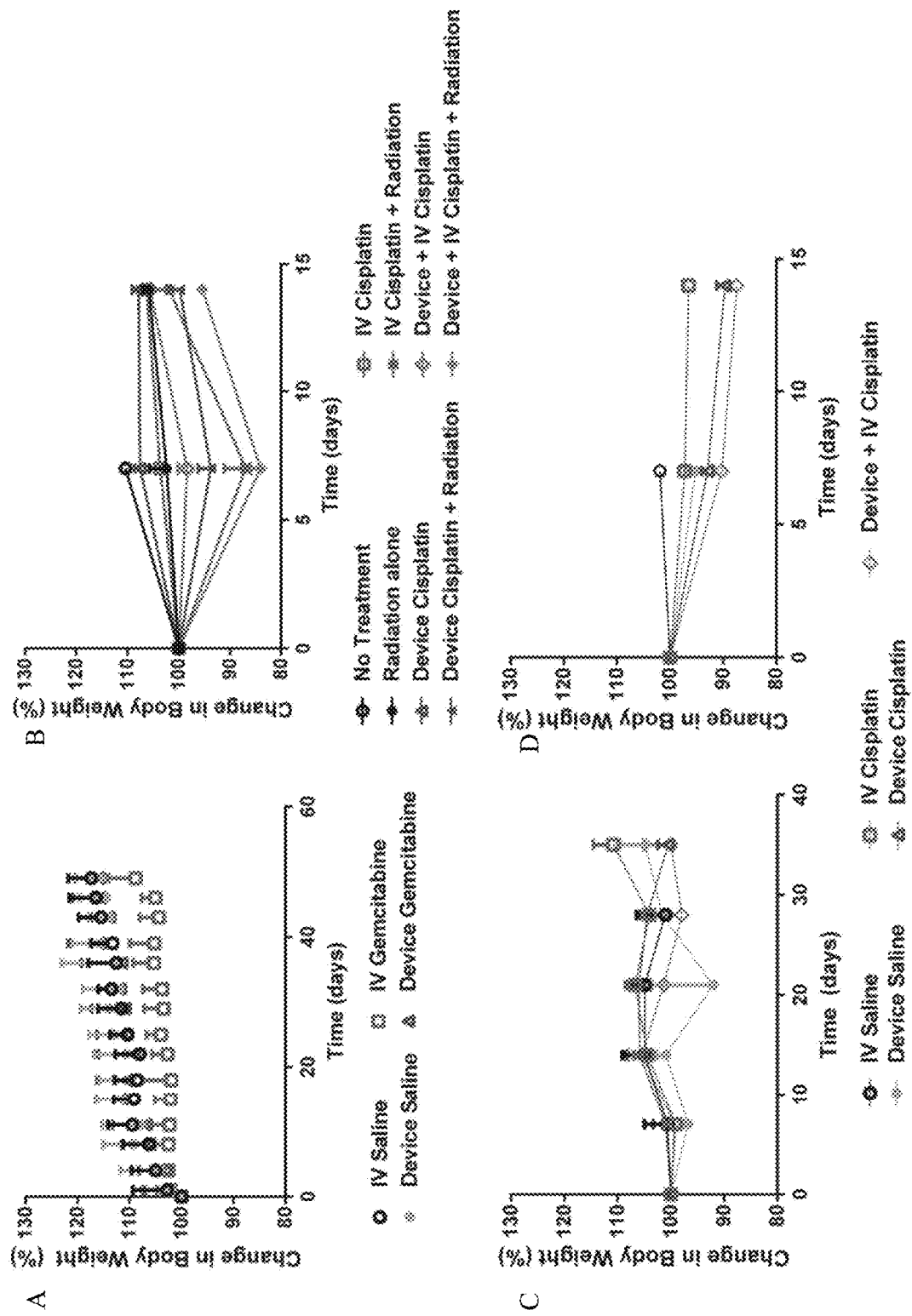
FIGS. 33 A-D

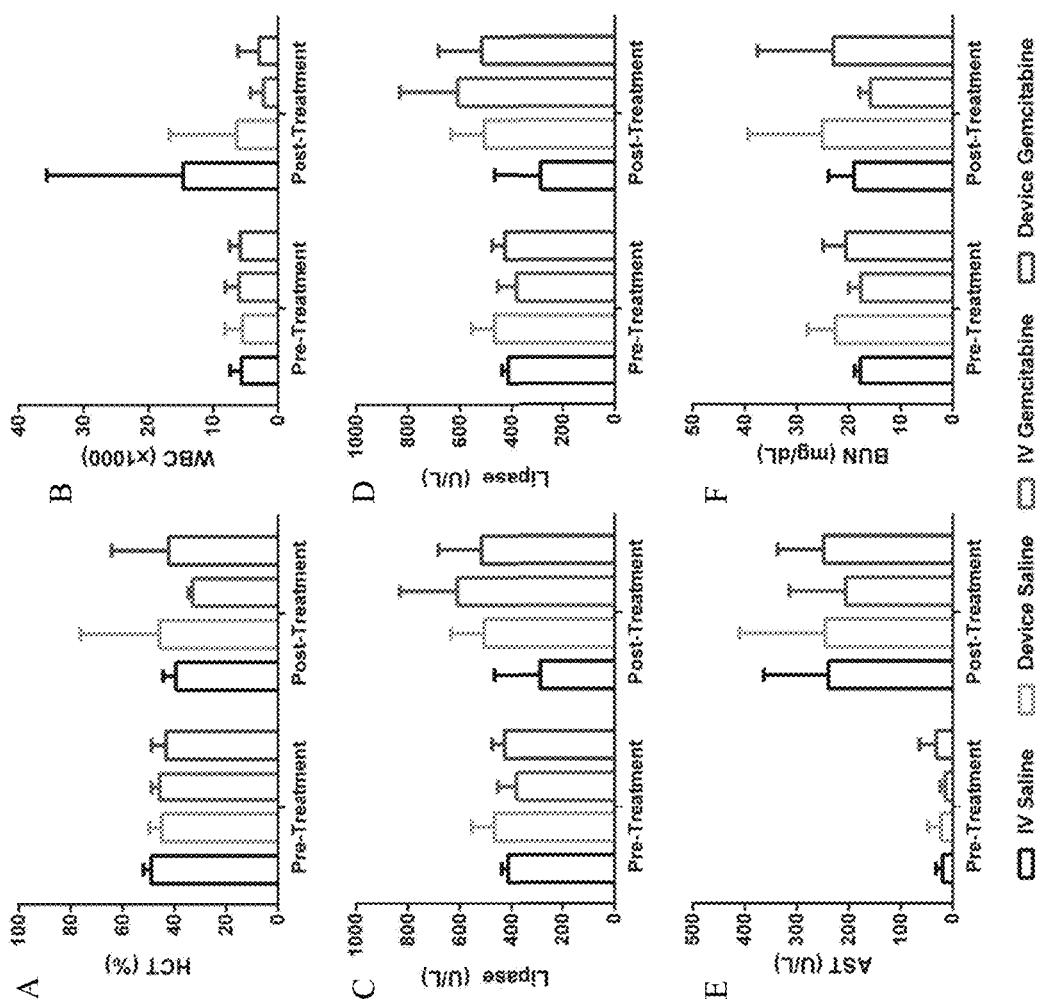
FIGS. 34 A-F

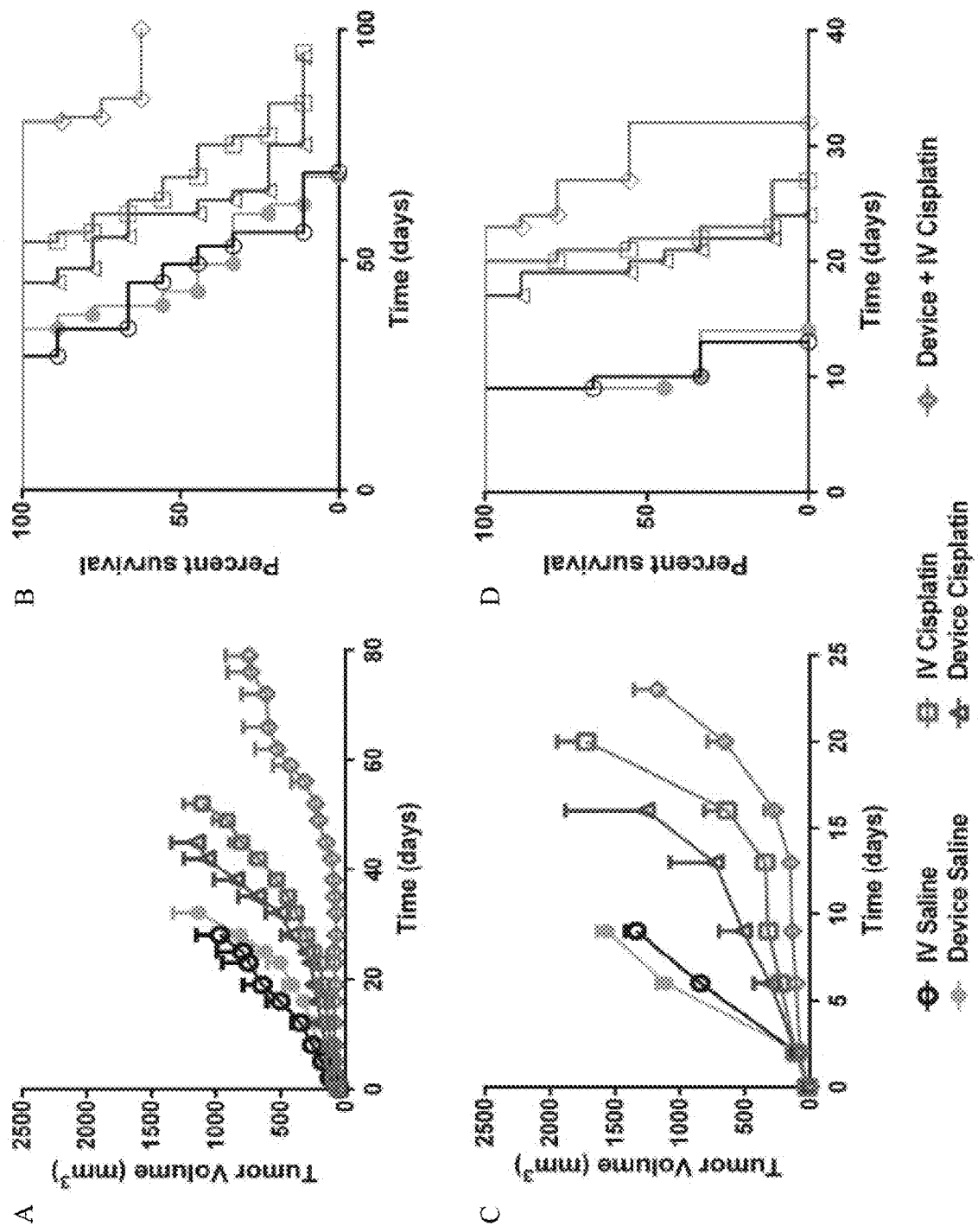
FIGS. 35 A-D

COMBINED LOCAL DELIVERY OF THERAPEUTIC AGENTS USING INTERVENTIONAL DEVICES AND RADIATION

CROSS-REFERENCE TO RELATED APPLICATIONS

The present application is a continuation of U.S. application Ser. No. 14/978,262 titled "COMBINED LOCAL DELIVERY OF THERAPEUTIC AGENTS USING INTERVENTIONAL DEVICES AND RADIATION," filed Dec. 22, 2015, which claims the benefit of U.S. Provisional Patent Application No. 62/096,780, filed Dec. 24, 2014, the entire contents of each of the foregoing applications is hereby incorporated by reference herein in its entirety.

FEDERALLY SPONSORED RESEARCH OR DEVELOPMENT

This invention was made with government support under Grant Number CA174425 awarded by the National Institutes of Health. The government has certain rights in the invention.

BACKGROUND

Field of the Invention

Embodiments of the present invention relate to a combination therapy using an interventional drug delivery system and radiotherapy, and more particularly, to a system and method for facilitating delivery of various cargos, such as, for example, therapeutic agents, to target sites of internal body tissue in vivo, in combination with radiotherapy.

Description of Related Art

Many techniques exist for the treatment of diseased tissues, including therapeutic drugs (e.g., chemotherapy) and radiotherapy. Additionally, many techniques exist for the delivery of drugs, therapeutic agents, and radiotherapy to the body. Traditional drug delivery methods include, for example, oral administration, topical administration, intravenous administration, and intramuscular, intradermal, and subcutaneous injections. With the exception of topical administration which permits more localized delivery of therapeutic agents to particular area of the body, the aforementioned drug delivery methods generally result in systemic delivery of the therapeutic agent throughout the body. Accordingly, these delivery methods are not optimal for localized targeting of drugs and therapeutic agents to specific internal body tissues.

Both traditional drug delivery and traditional radiotherapy techniques may suffer from limited efficacy in treating perfusion limited tissues, such as solid tumors. Dense stromal environments and poor vascularization impede diffusion, reducing drug exposure to the primary tumor. Radiotherapy typically subjects the target tissue, either directly or indirectly, to ionizing radiation, which disrupts the growth of the tissue. In some instances, radiotherapy forms free radicals from oxygen in the tissue to destroy the target cells; however, solid tumors that lack sufficient vascularization are often hypoxic and cannot produce the free radicals necessary to treat the tumor. Radiotherapy may be used in combination with radiosensitizers, which increase the susceptibility of tissue to ionizing radiation; however, because of the above-mentioned diffusion limitations, it is often difficult to administer radiosensitizers to solid tumors while also avoiding harm to the body caused by systemic toxicity.

Accordingly, it would be desirable to provide an improved system and method for treating body tissues that overcomes the aforementioned limitations by selectively and locally targeting delivery of various drugs and therapeutic agents in combination with radiotherapy to synergistically improve the effectiveness of both the local drug treatment and radiotherapies.

SUMMARY

The above and other needs are met by aspects of the present invention which provide, in one instance, a delivery system, and in particular, a delivery system for local drug delivery to a target site of body tissue in combination with radiotherapy applied to the target site. Some embodiments of the present invention may be directed to a method of delivering a cargo to a target site of body tissue in combination with radiotherapy. In some embodiments the method may include disposing a source electrode proximate to a target site of body tissue in vivo; disposing a counter electrode in electrical communication with the source electrode, the counter electrode being configured to cooperate with the source electrode to form a localized electric field proximate to the target site; disposing a cargo proximate the electric field and capable of being delivered to the target site when exposed to the localized electric field formed between the source electrode and the counter electrode; applying a voltage potential across the source and counter electrodes to form an electric field, thereby delivering at least a portion of the cargo to the target site; and/or applying a radiation to the target site.

In some embodiments the method may include disposing the cargo in a reservoir such that the reservoir is configured to place the cargo in the localized electric field. The method may include disposing the reservoir at least partially about the source electrode, such that upon activation of the electric field the cargo diffuses out of the reservoir and toward the counter electrode. The method may additionally or alternatively include disposing a cellulose membrane across an opening of the reservoir such that the membrane partially seals the reservoir while allowing the cargo to diffuse out of the reservoir toward the counter electrode. In some embodiments, the method includes disposing an inlet and an outlet in the reservoir such that cargo is configured to flow continuously across the source electrode.

In some embodiments, the cargo may include at least one radiosensitizer. The at least one radiosensitizer may include one of 1,2,4-benzotriazin-3-amine 1,4-dioxide (SR 4889) and 1,2,4-benzotriazine-7-amine 1,4-dioxide (WIN 59075), gemcitabine, cisplatin, carboplatin, oxaliplatin, 5-fluorouracil, or fluorodeoxyuridine. In some embodiments, the cargo includes at least one cytotoxic agent.

In some embodiments of the method, the radiation is applied to the target site from an external source. The radiation may be applied by an external beam irradiator. The radiation may additionally or alternatively be applied by brachytherapy. In some embodiments, the radiation may be applied by disposing a radiation source proximate the target site. In some embodiments, the radiation may be applied by disposing at least one radiation source on a reservoir. The radiation may be applied by disposing a radiation source within the target site. Some embodiments of the method may apply the radiation after the cargo is delivered to the target site. Additionally or alternatively, the radiation may be applied substantially concurrently with the delivery of the cargo to the target site.

Some embodiments of the method may provide intravenous delivery of a second cargo. In some embodiments, the cargo comprises at least one of small ionic molecules, nucleic acids, proteins, organic nanoparticles, therapeutic agents, and imaging agents. In some embodiments of the method, disposing a source electrode and a counter electrode further comprises disposing a source electrode and a counter electrode comprised of one of a metallic material, a conductive polymer material, and combinations thereof. Disposing a counter electrode may further comprise disposing a counter electrode such that the counter electrode contacts the target site so as to promote directional transport of the cargo toward the target site. In some embodiments, the body tissue comprises a solid tumor.

In another embodiment of the present invention, a system for treating a target site of body tissue may be provided. The system may include a source electrode proximate to a target site of body tissue in vivo; a counter electrode in electrical communication with the source electrode, the counter electrode being configured to cooperate with the source electrode to form a localized electric field proximate to the target site; wherein the localized electric field is configured to deliver at least a portion of a cargo to the target site by applying a voltage potential across the source and counter electrodes to form the localized electric field; and/or a radiation source configured to apply a radiation to the target site. Some embodiments of the system include a reservoir such that the reservoir is configured to place the cargo in the localized electric field. The reservoir may be disposed at least partially about the source electrode, such that upon activation of the electric field the cargo diffuses out of the reservoir and toward the counter electrode. In some embodiments, the system may include a cellulose membrane configured to be disposed across an opening of the reservoir such that the membrane is configured to partially seal the reservoir while allowing the cargo to diffuse out of the reservoir toward the counter electrode. Some embodiments of the system include an inlet and an outlet defined in the reservoir such that cargo is configured to flow continuously across the source electrode.

In some embodiments, the cargo includes at least one radiosensitizer. The at least one radiosensitizer may include one of 1,2,4-benzotriazin-3-amine 1,4-dioxide (SR 4889) and 1,2,4-benzotriazine-7-amine 1,4-dioxide (WIN 59075), gemcitabine, cisplatin, carboplatin, oxaliplatin, 5-fluorouracil, or fluorodeoxyuridine. In some embodiments, the cargo includes at least one cytotoxic agent.

Some embodiments of the radiation source are configured to apply the radiation from an external position. In some embodiments, the radiation source is an external beam irradiator. Additionally or alternatively, the radiation source may be a brachytherapeutic device. The radiation source may be configured to be disposed proximate the target site. In some embodiments, the radiation source may be configured to be disposed on a reservoir. The radiation source may additionally or alternatively be configured to be disposed within the target site. In some embodiments, the radiation may be configured to be applied after the cargo is delivered to the target site. In some embodiments of the system, the radiation may be configured to be applied substantially concurrently with the delivery of the cargo to the target site. Embodiments of the system may include a second cargo configured to be introduced to the target site intravenously. In some embodiments, the cargo comprises at least one of small ionic molecules, nucleic acids, proteins, organic nanoparticles, therapeutic agents, and imaging agents.

In some embodiments, each of the source electrode and the counter electrode may comprise one of a metallic material, a conductive polymer material, and combinations thereof. The counter electrode may be configured to contact the target site so as to promote directional transport of the cargo toward the target site. In some embodiments of the system, the body tissue may comprise a solid tumor.

As such, embodiments of the present invention are provided to enable highly targeted and efficient delivery of various cargos to predetermined target sites in combination with radiotherapy. In this regard, aspects of the present invention provide significant advantages as otherwise detailed herein.

BRIEF DESCRIPTION OF THE DRAWINGS

In order to assist the understanding of embodiments of the invention, reference will now be made to the appended drawings, which are not necessarily drawn to scale. The drawing is exemplary only, and should not be construed as limiting the invention.

FIGS. 1A-1G are schematic drawings of various embodiments of a delivery system having a source electrode and counter electrode configured to cooperate to form an electric field for delivering a cargo, according to one embodiment of the present disclosure;

FIG. 6 is a partial view of a delivery system employing a catheter device for positioning of a source electrode, wherein the delivery system includes a plurality of independently controlled source electrodes and a plurality of insulating members configured to provide controlled delivery zones for specific targeting of target sites, according to one embodiment of the present disclosure;

FIG. 7 is a partial view of a delivery system having a source electrode encapsulated by a polymer matrix reservoir having a cargo contained therein, according to one embodiment of the present disclosure;

FIGS. 8A and 8B are partial views of a delivery system having a source electrode with at least one insulating member engaged therewith, the source electrode and at least one insulating member being encapsulated by a polymer matrix reservoir having a cargo contained therein;

FIG. 9 is a partial view of a delivery system having a plurality of independently controlled source electrodes and a plurality of insulating members arranged to provide controlled delivery zones, wherein the source electrodes and the insulating members are encapsulated in a polymer matrix, according to one embodiment of the present disclosure;

FIG. 10 is a partial view of a delivery system having a source electrode serially disposed between a pair of expandable members configured to occlude a target site, wherein the expandable members are in a relaxed state, according to one embodiment of the present disclosure;

FIG. 11 is a partial view of the delivery system of FIG. 10, illustrating the expandable members in an expanded state so as to occlude the target site such that delivery of a cargo is limited thereto;

FIGS. 20A-D are partial views of the delivery system according to one embodiment of the present disclosure;

FIGS. 21A-D illustrates experimental results of delivery system parameters according to one embodiment of the present disclosure;

FIG. 22A is an illustration of an orthotopic pancreatic cancer model according to one embodiment of the present disclosure;

FIG. 22B is an illustration of an orthotopic breast cancer model according to one embodiment of the present disclosure;

FIG. 32A illustrates experimental results of saline and gemcitabine delivery in a pancreatic cancer PDX model according to one embodiment of the present disclosure;

FIG. 32B is a histological staining of tumors for saline and gemcitabine delivery in a pancreatic PDX model according to one embodiment of the present disclosure;

FIG. 33A illustrates experimental results of body weight changes in PDX mice according to one embodiment of the present disclosure;

FIG. 33B illustrates experimental results of body weight changes in T11 syngeneic mice including radiation according to one embodiment of the present disclosure;

FIG. 33C illustrates experimental results of body weight changes in SUM149 orthotopic xenograft mice according to one embodiment of the present disclosure;

FIG. 33D illustrates experimental results of body weight changes in T11 orthotopic syngeneic mice according to one embodiment of the present disclosure;

FIGS. 34A-F illustrate pertinent laboratory values for gemcitabine treatment in an orthotopic PDX model of pancreatic cancer according to one embodiment of the present disclosure;

FIGS. 35A and 35B illustrate experimental results of cisplatin treatment in SUM 149 tumor xenografts according to one embodiment of the present disclosure;

FIGS. 35C and 35D illustrate experimental results of cisplatin treatment in T11 syngeneic breast cancer models according to one embodiment of the present disclosure;

DETAILED DESCRIPTION OF THE PREFERRED EMBODIMENTS

Figure 1B:
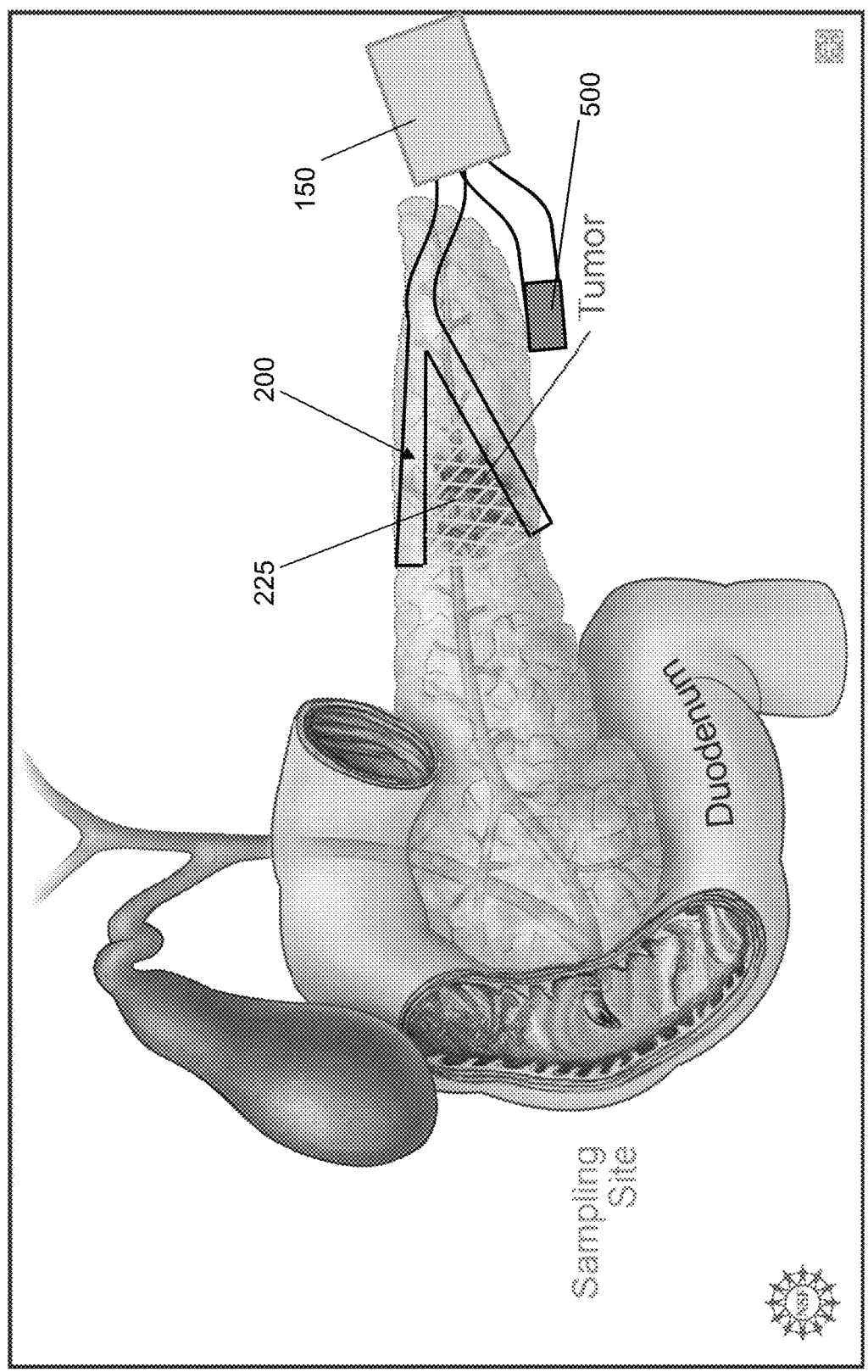

Embodiments of the present invention now will be described more fully hereinafter with reference to the accompanying drawings. The invention may be embodied in many different forms and should not be construed as limited to the embodiments set forth herein; rather, these embodiments are provided so that this disclosure will satisfy applicable legal requirements. Like numbers refer to like elements throughout.

Brief Overview

Embodiments of the present invention are directed to systems and methods for treating diseased tissue by providing local delivery of treatment or therapeutic agents (otherwise referred to herein as "cargo") to specific locations, including intracellular locations, in combination with radiation treatment. The local delivery systems may deliver the cargo to a target site in effective amounts without endangering normal tissues or cells and thus reduce or prevent the occurrence of undesirable side effects. Further, such delivery systems may electrically enhance the local delivery of treatment agents into the wall tissues or cells of the living body. These systems are designed to target certain tissue and cell locations and deliver the treatment agents directly to those locations, while minimizing any effects on non-targeted tissues and cells. In combination with the local delivery system, radiotherapy may be used on the diseased site to aid in the treatment of the tissue. In particular, embodiments of the present invention are directed to delivering local therapeutic agent synergistically with targeted radiotherapy to a particular diseased site while minimizing the harmful, systemic effects on the patient. An interventional drug delivery system and associated methods are described in related U.S. patent application Ser. No. 13/202,810, published as U.S. 2011/0306878, which is a national stage entry of PCT/US 10/25416, which claims the benefit of U.S. Provisional Application No. 61/155,880, each of which is hereby incorporated by reference in its entirety.

Interventional Drug Delivery System

Embodiments of the local delivery system may rely on the transport of charged and uncharged species under the influence of a localized electric field generated at the site of interest. The overall transport of charged and uncharged species is based upon three characteristic driving forces, which includes passive diffusion, electroosmosis, and electromigration. Passive diffusion involves the movement of a chemical species from a region of high concentration to an area of low concentration. Electroosmosis is the movement of a solute species via a solvent flow accompanied by the movement of an extraneous charged species. Electroosmosis encompasses the solvent flow referred to as hydrokinesis. Electromigration is the movement of a charged species through an applied electric field to an electrode of opposite polarity. Transport of a neutrally charged species is driven by passive diffusion and electroosmosis only, whereas all transport modalities, passive diffusion, electroosmosis, and electromigration contribute to the flux of a charged species.

In this regard, the local delivery system may provide an interventional drug delivery system and methods for localized delivery of therapeutic agents to internal locations in the human body using a controlled electrical field. The system may be constructed to deliver the agents specifically to the site of interest, improving penetration of the agent while limiting effect upon non-targeted tissue. The delivery system may be fashioned to deliver the agents via intravascular, intraperitoneal, minimally invasive surgery, and natural orifice transluminal endoscopic surgery (NOTES) modalities. The action of the electric field may be controlled through a programmable power supply or a function generator. By using various electrode designs and placement configurations, highly localized and focused delivery of cargo to the tissue of interest may be achieved. The overall controlled release characteristics of the delivery system may be dependent upon the charge, size, conductivity, concentration, and $pK_a$ of the chemical species and nanoparticles, pH of the surrounding environment, resistance of the site of interest, current and voltage applied, electrode design and amount of extraneous ions at site of interest.

Embodiments of the delivery system may be implemented in the delivery of therapeutic agents for such diverse areas as oncology, pulmonary, gastrointestinal (GI), and neurology applications. In particular, the local delivery system may be useful in, but not limited to, areas for which radiotherapy is a viable treatment, so as to combine the beneficial effects of the localized delivery of therapeutic agents with radiation. For example, embodiments of the present invention find application in the field of interventional oncology for the treatment of various cancers, which may include, for example, pancreatic cancers, breast cancers, lung cancer, esophageal cancers, bladder cancers, colorectal cancers, liver cancers, hepatic metastases, bile duct cancers, renal cancers, cervical cancers, prostate cancers, ovarian cancer, thyroid cancers, uterine cancers, and leukemia. In particular, accessing bone marrow tissue may be advantageous. Other applications may cover pulmonary diseases, neurological disorders as well as cardiovascular applications.

In some instances, embodiments of the delivery system may employ an approach using iontophoresis. As used herein, the term "iontophoresis" means the migration of ionizable molecules through a medium driven by an applied low level electrical potential. This electrically mediated movement of molecules into tissues is superimposed upon concentration gradient dependent diffusion processes. If the medium or tissue through which the molecules travel also carries a charge, some electro-osmotic flow occurs. However, generally, the rate of migration of molecules with a net negative charge towards the positive electrode and vice versa is determined by the net charge on the moving molecules and the applied electrical potential. The driving force may also be considered as electrostatic repulsion. Iontophoresis usually requires relatively low constant DC current in the range of from about 2-5 mA. The applied potential for iontophoresis will depend upon number of factors, such as the electrode configuration and position on the tissue and the nature and charge characteristics of the molecules to be delivered. For example, embodiments of the present invention may use iontophoresis to overcome the high hydrostatic pressure in some body tissues, such as solid tumors. The localized iontophoretic devices of the present invention may overcome the perfusion limitations of solid tumors by administering the treatment directly into the target tissues in accordance with the embodiments described herein.

In general, such a delivery system may be used to administer a cargo including, but not limited to, therapeutic agents such as drug molecules, proteins, peptides, antibodies, antibody scaffolds or fragments of antibodies, nucleotides, contrast agents and dyes (including radiolabels, fluorophores and chelated magnetic species), liposomes, micelles, nanoparticles, multi-molecular aggregates (such as, for example, albumin/paclitaxel or Abraxane™) and combinations thereof, with or without cargo and/or targeting capabilities. Small molecules may include chemotherapeutic agents such as alkylating agents, anti-metabolites, plant alkaloids and terpenoids, vinca alkaloids, podophyllotoxin, taxanes, topoisomerase inhibitors, and antitumor antibiotics, as well as analgesics and local anesthetics. The system may also include the delivery of pro-drugs, small molecules and nanoparticles, in some instances having neutral charge before delivery, that may be subsequently charged or triggered to release cargo under physiological conditions.

Furthermore, the cargo may include small ionic molecules, nucleic acids, proteins, therapeutic agents, diagnostic agents, and imaging agents as well as organic nanoparticles which may encapsulate a wide range of therapeutic, diagnostic, and imaging agents. The cargo may be configured to traffic preferentially based on size, shape, charge and surface functionality; and/or controllably release a therapeutic. Such cargos may include but are not limited to small molecule pharmaceuticals, therapeutic and diagnostic proteins, antibodies, DNA and RNA sequences, imaging agents, and other active pharmaceutical ingredients. Further, such cargo may include active agents which may include, without limitation, analgesics, anti-inflammatory agents (including NSAIDs), anticancer agents, antimetabolites, anthelmintics, anti-arrhythmic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immunological agents, therapeutic proteins, enzymes, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators, xanthines, and antiviral agents. In addition, the cargo may include a polynucleotide. The polynucleotide may be provided as an antisense agent or interfering RNA molecule such as an RNAi or siRNA molecule to disrupt or inhibit expression of an encoded protein.

The cargo may also include, without limitation, radiosensitizers such as, for example, 1,2,4-benzotriazin-3-amine 1,4-dioxide (SR 4889) and 1,2,4-benzotriazine-7-amine 1,4-dioxide (WIN 59075), gemcitabine, the platinum coordination complexes (e.g., cis-diammino-platinum(II) (cisplatin), cis-diammine-1,1-cyclobutane dicarboxylatoplatinum(II) (carboplatin), cis-[(1R,2R)-1,2-cyclohexanediamine-N,N'] [oxalate(2-(-O,O']platinum (oxaliplatin)), the fluoropyrimidines (e.g., 5-fluorouracil, fluorodeoxyuridine).

Other cargo may include, without limitation, MR imaging agents; contrast agents; gadolinium chelates; gadolinium-based contrast agents; platinum coordination complexes such as cisplatin and carboplatin; anthracenediones, such as mitoxantrone; substituted ureas, such as hydroxyurea; and adrenocortical suppressants, such as mitotane and aminoglutethimide.

FIGS. 1-20 illustrate various embodiments and aspects of a delivery system 100 in accordance with portions of the present invention. In general, the delivery system is provided for delivering a cargo to, or through, a localized area of a passageway or other internal body tissue in order to treat the localized area of the passageway or tissue with minimal, if any, undesirable effect on other body tissue. Such a system may be implemented intraluminally, through natural orifices, or by minimally invasive surgery such that the system may be used in vivo. The delivery system 100 may generally include a source electrode, a counter electrode, a reservoir for carrying a cargo (e.g., a therapeutic agent), and/or an electrode deployment device.

As described previously, the delivery apparatus 100 which may deliver cargo iontophoretically to target sites for localized treatment. In general, iontophoresis technology uses an electrical potential or current across a target site (e.g., a semipermeable barrier) to drive ionic fixatives or drugs (or drive nonionic fixatives or drugs) in an ionic solution. Iontophoresis facilitates both transport of the fixative or drug across the target site and enhances tissue penetration. In the application of iontophoresis, two electrodes, a source electrode and a counter electrode (in some instances, the electrodes may be positioned on opposing sides of the target site, though such a configuration or arrangement is not required), are utilized to develop the required potential or current flow. The positioning of the electrodes may be accomplished using an electrode deployment device 150. The electrode deployment device 150 may be capable of positioning the source electrode, the counter electrode, and the reservoir such that the therapeutic agents may be delivered through intravascular, intraperitoneal, and natural orifice transluminal endoscopic surgery (NOTES) modalities. Some versions of the delivery system may employ the technique of reverse iontophoresis, wherein a small molecule or other substance may be extracted from the surrounding medium. In this manner, toxic substances or excess cargo materials may be removed from locations in vivo.

In some instances, the electrode deployment device 150 may comprise a catheter device to be deployed in vivo using the intravascular route. In other embodiments, the electrode deployment device 150 may comprise an endoscopic device for deployment via natural orifices in the body. In other instances, the electrode deployment device 150 may comprise a laparoscopic device for minimally invasive surgical intervention. In other embodiments, the electrode deployment device 150 may be surgically implanted in a suitable location in vivo, such as, for example, the peritoneal cavity. In yet other instances, the electrode deployment device 150 may implement combinations of two or more of the embodiments listed above. According to some embodiments, the electrode deployment device 150 may locate the source electrode, counter electrode, and/or reservoir at the target site of interest through use of an imaging system.

FIGS. 1-11 and 17-20 illustrate various embodiments of a source electrode 200 implemented by the delivery system 100. The repulsive force for driving the charged cargo through the target site tissue is generated by placing the source electrode 200 at or proximate to the target site of interest. The delivery system 100 may include one or more source electrodes 200. By optimizing the placement and geometric profile of the source electrode(s) 200, considerable control may be achieved over the penetration depth, direction and overall area of delivery of the cargo to the target site. The source electrode(s) 200 may be configured as a single probe or an array of probes comprised, for example, of thin wires, foil, mesh, pellets, disks, stents, clamps, prongs, clips, needles, hollow tubes or combinations thereof. For example, as shown in FIG. 1, the source electrode 200 may include a mesh arrangement 225 (see also FIGS. 1B, 1C, and 18B) opposably positioned with respect to a counter electrode 500. In accordance with such an embodiment, in some instances, the counter electrode 500 may be positioned, for example, on an exterior surface of the pancreas/organ of interest. The source electrode 200 having the mesh arrangement 225 may also be placed on the exterior surface to cover a specific target tissue such as, for example, a tumor, as shown in FIG. 1B.

Figure 1C:
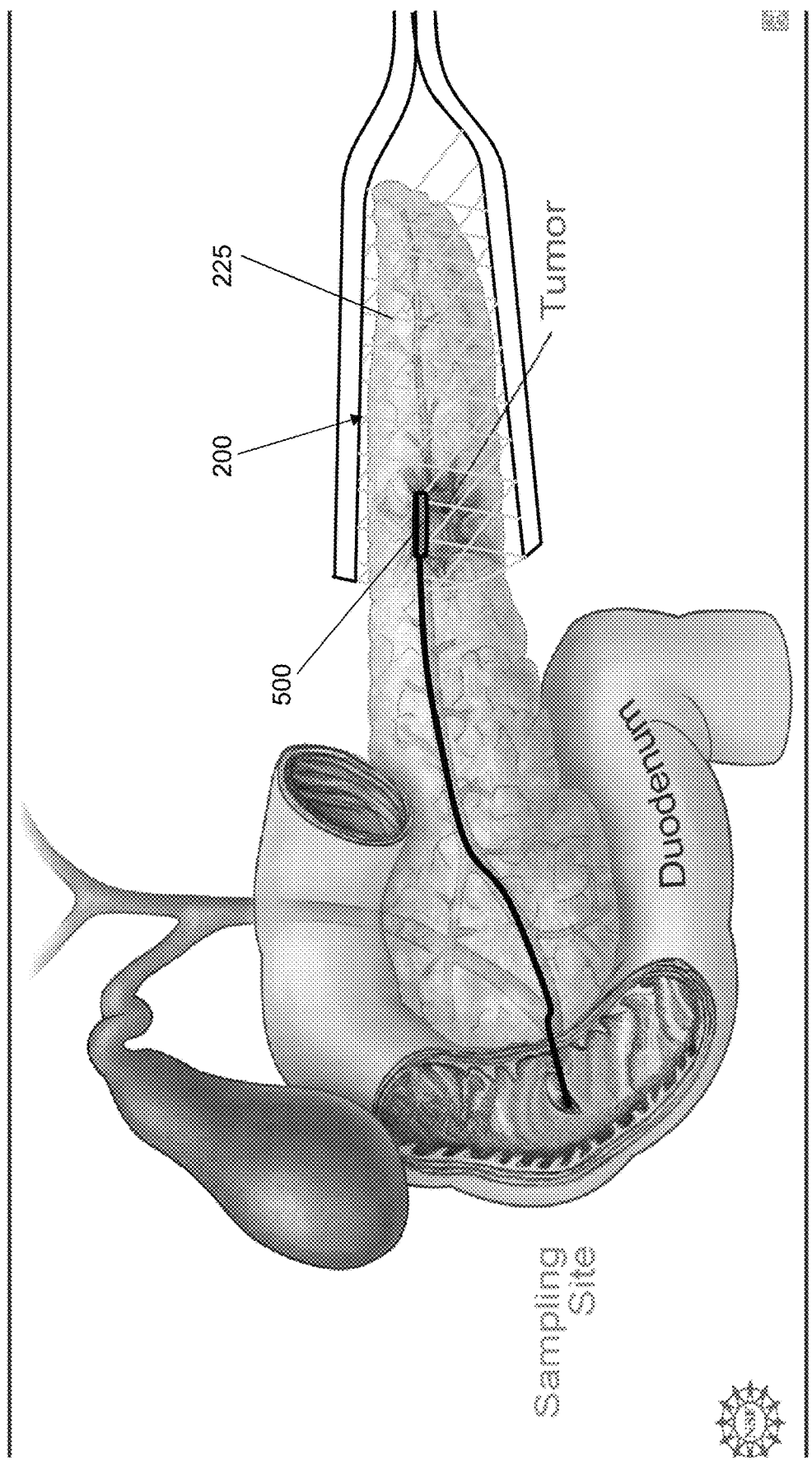
Figure 1D:
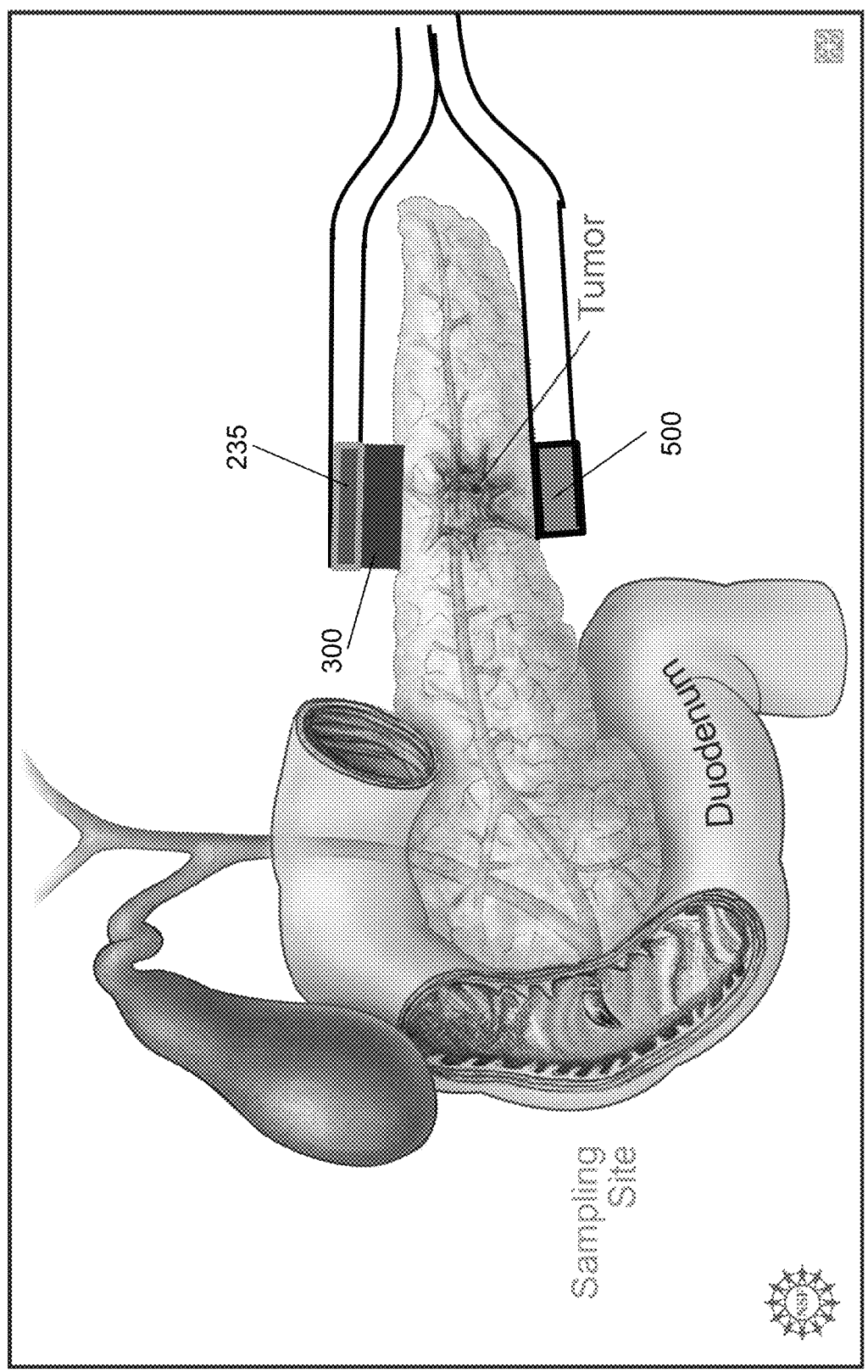
Figure 1E:
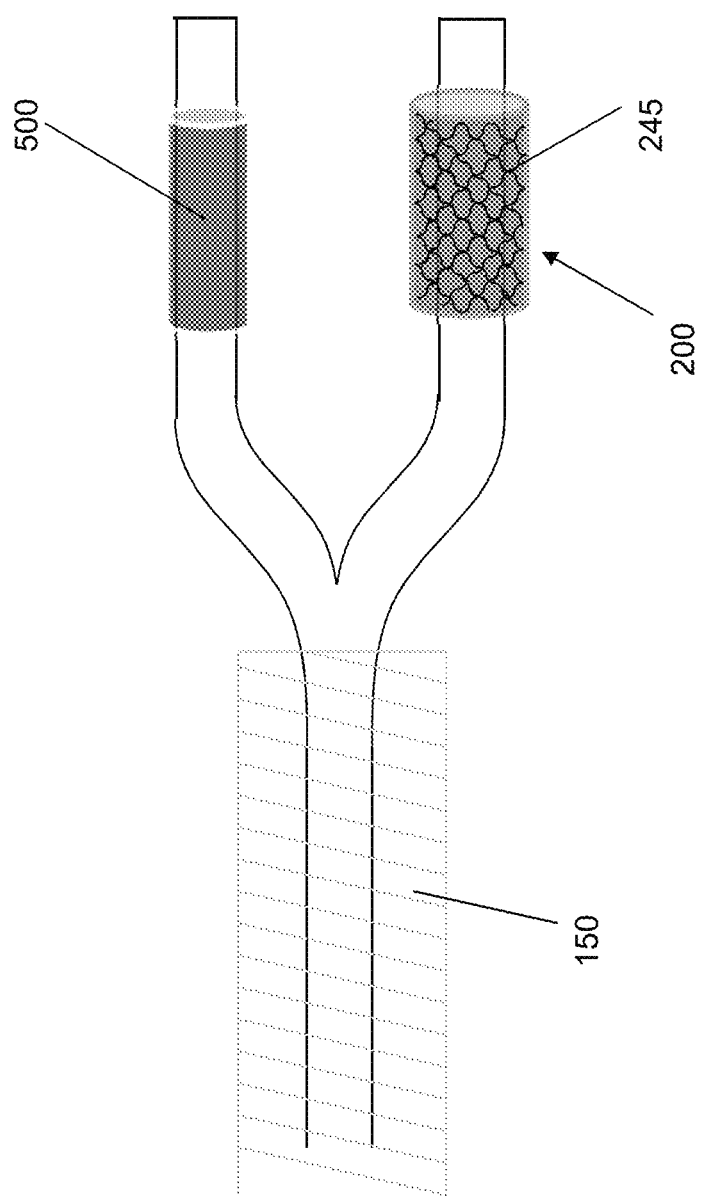
Figure 1F:
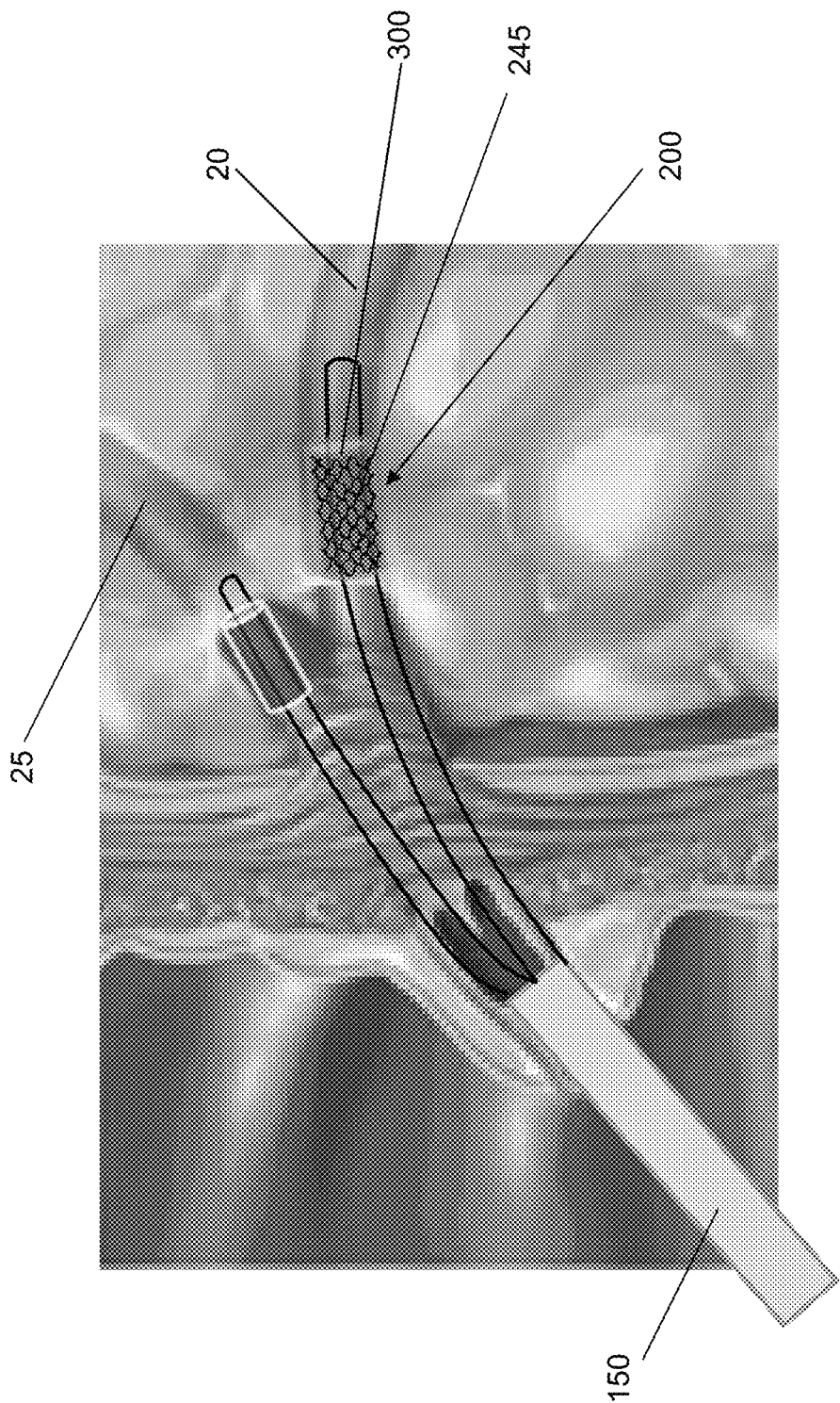
Figure 1G:
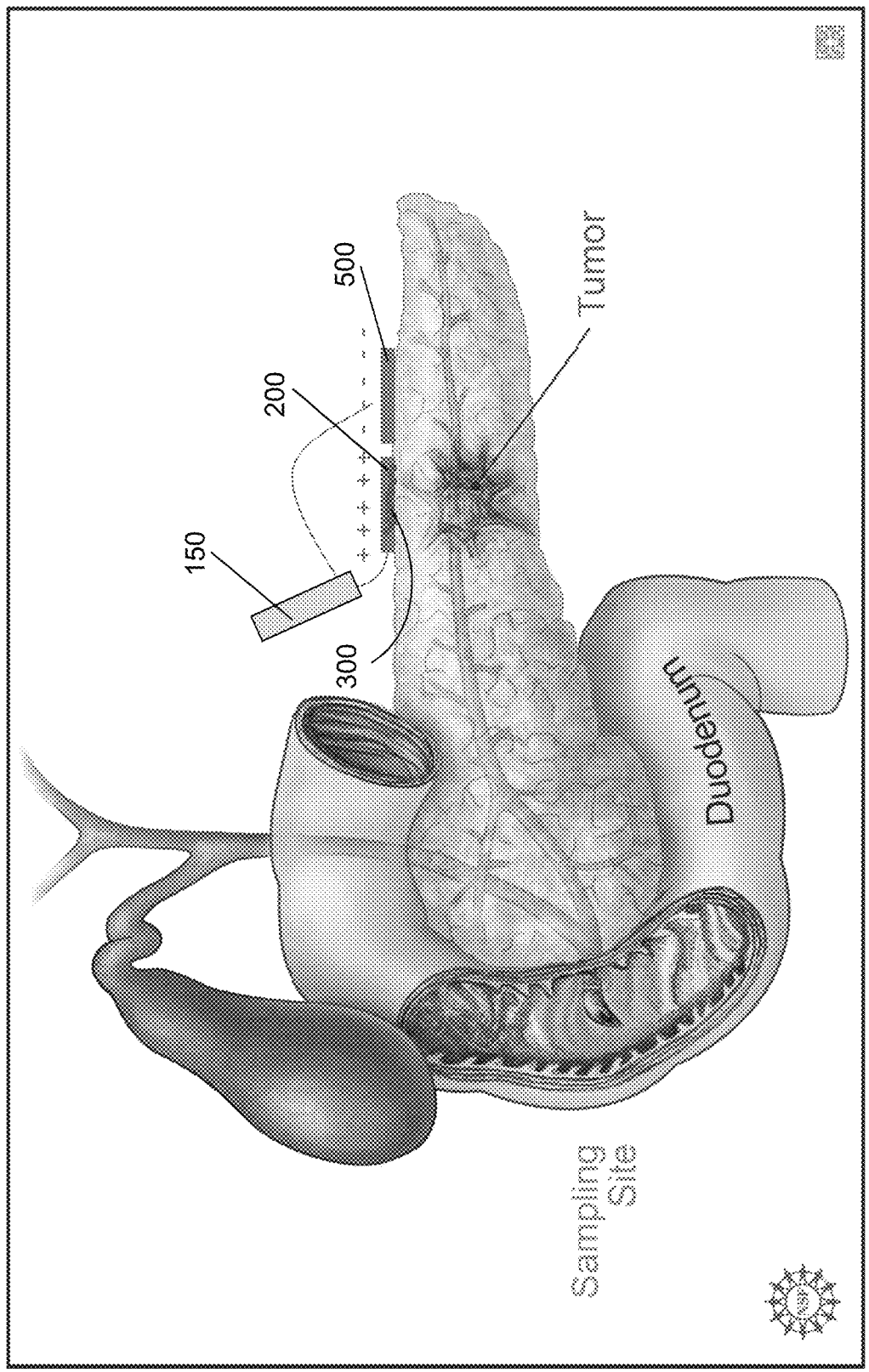
Figure 2:
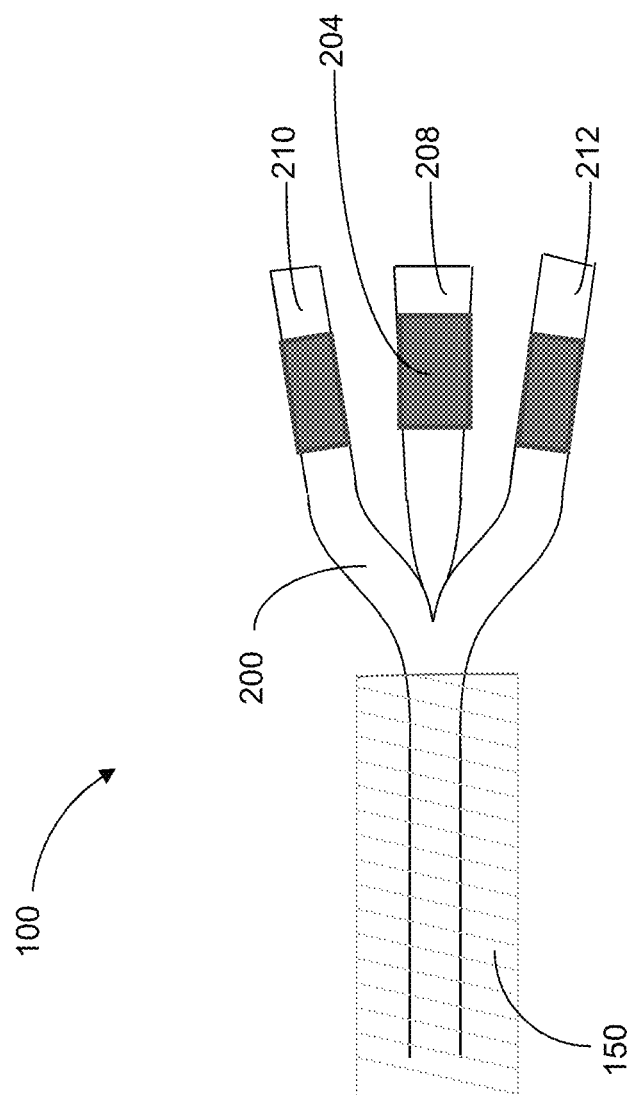
FIG. 2 is a partial view of a delivery system having a source electrode with an array of probes, according to an alternative embodiment of the present disclosure.

In another embodiment, the mesh arrangement 225 source electrode 200 may be configured to encase part or a portion of the target tissue (e.g., a conical mesh encasing the tail of the pancreas, as shown in FIG. 1C). In other instances, the source electrode 200 may be configured or arranged as foil or patch electrodes 235, as shown in FIG. 1D, wherein the drug reservoir 300 is coupled to the source electrode 200. The patch source electrode 235 may be configured as clamps or prongs situated at the end of the electrode deployment device 150, such as, for example, an endoscopic or laproscopic device, as shown in FIG. 2, wherein an intermediary prong 208 may include the patch source electrode 235. In this regard, the configuration may be modified to be internally deployed by the electrode deployment device 150, wherein the mesh arrangement 225 may be replaced by a stent device 245 (acting as the source electrode 200), as shown in FIG. 1E, that is positioned within the pancreatic duct 20, while the counter electrode 500 may be positioned within an alternate branch of the same duct or, alternatively, the bile duct 25 for example, as shown in FIG. 1F. In some instances, the source electrode may include a reservoir 300 coupled or otherwise attached thereto for holding the cargo to be delivered to the target site. In this manner, the reservoir 300 and/or the tissue of interest may be at least partially disposed between the source electrode 200 and the counter electrode 500. The source electrode(s) 200 may be fabricated from various materials including, but not restricted to, conducting metals, such as silver, silver chloride, platinum, aluminum, or conducting polymers such as polypyrrole, polyaniline, polyacetylene, or poly(3,4-ethylenedioxythiophene). In some instances, both the source electrode 200 and the counter electrode 500 may be patch source electrodes 235, which may be positioned in a side-by-side or otherwise proximally positioned on an organ, tissue, or other target site, as shown in FIG. 1G. That is, the cargo of the reservoir 300 may penetrate the target site to reach, for example, a tumor when the voltage potential is applied between the source electrode 200 and the counter electrode 500. Of course, the patch source electrodes 235 may be on opposite sides of the organ, tissue, or target site, or may be otherwise appropriately configured to deliver the cargo to the target site.

Figure 3:
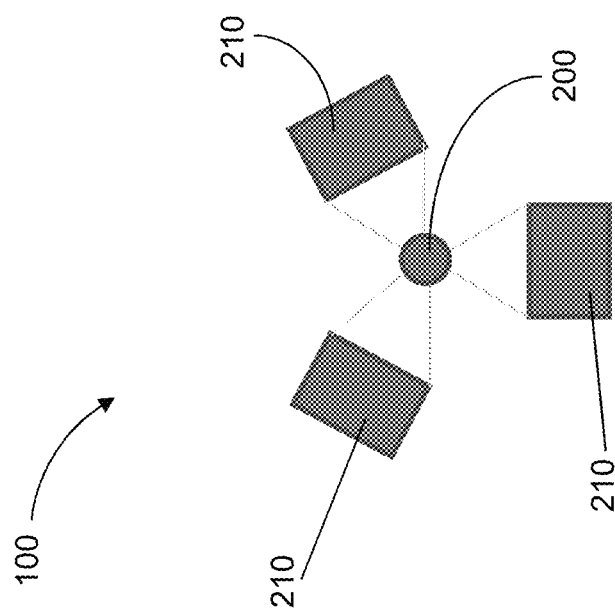
FIG. 3 is a partial view of a delivery system having a source electrode with an array of probes, according to yet another embodiment of the present disclosure.

According to some embodiments, the source electrode 200 may include an array of multi-functional probes, combining imaging and drug delivery functionalities, as illustrated in FIGS. 2 and 3. In this regard, the use of paramagnetic or radio-opaque materials in the probe body may be used for imaging purposes. In other instances, catheter devices may be capable of simultaneous delivery of imaging agents. According to other embodiments, the incorporation of a light source and camera may be incorporated into the probe for endoscopic devices. Various combinations of such imaging and delivery probes may be implemented by the delivery system 100. For example, as illustrated in FIG. 2, the intermediary prong 208 may include the electrode element 204, while the outer prongs 210, 212 include imaging devices and/or agents capable of assisting with positioning of the source electrode 200. With reference to FIG. 3, the electrode element 204 may be radially surrounded by imaging devices 210 or agents, other source electrodes 200 or other probe members, which may be configured as dependent on the location of the target site within a patient's body.

Figure 4:
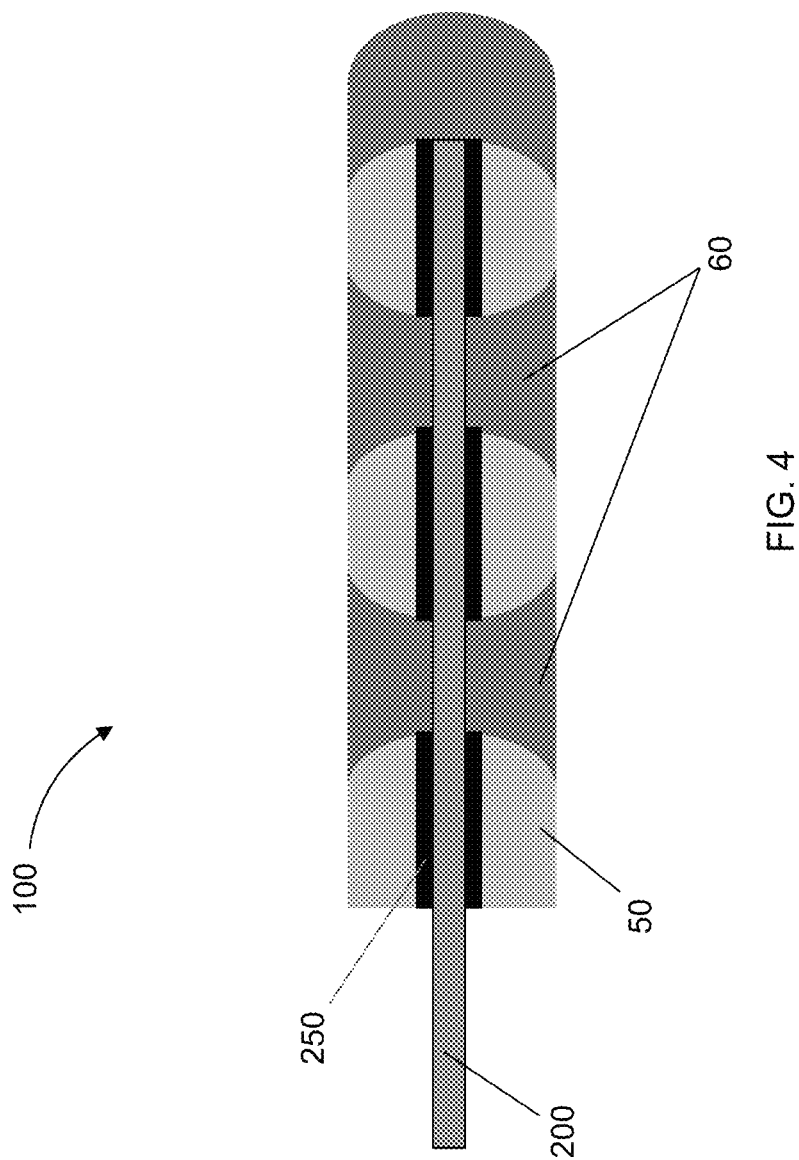
FIG. 4 is a partial view of a delivery system according to one embodiment of the present disclosure, illustrating a source electrode having a plurality of insulating members engaged therewith.

In some instances, the source electrode 200 may have one or more insulating layers or members 250 attached, connected, or otherwise engaged therewith. The insulating members 250 are provided to confer directionality to the transport profile of the cargo 60 with respect to the target site, as shown in FIG. 4, illustrating the source electrode 200 disposed within a tissue lumen 50. That is, the flux of the cargo will be attenuated corresponding to the insulated areas of the source electrode 200. In this regard, a partially insulated source electrode 200 may be for control over targeted delivery to specific in vivo locations. That is, by insulating a portion of the source electrode surface, control over delivery to the tissue or organ systems may be accomplished in a well defined manner. In this regard, the extent of transport from the sections of the target site exposed to the unshielded sections of the source electrode 200 may be greater than that of the transport from the shielded or insulated region of the source electrode 200.

Figure 5:
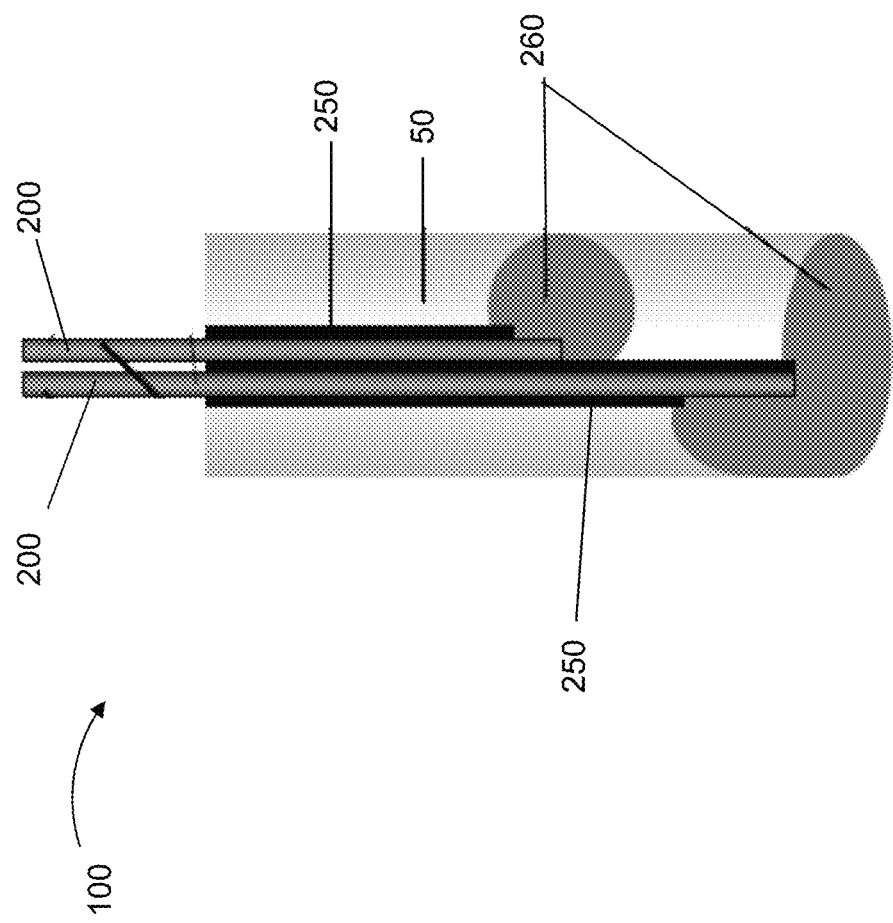
FIG. 5 is a partial view of a delivery system disposed within a tissue lumen, the delivery system having a plurality of independently controlled source electrodes and a plurality of insulating members configured to provide controlled delivery zones for specific targeting of target sites of the tissue lumen, according to one embodiment of the present disclosure.

In some aspects of the delivery system, a plurality of source electrodes 200 may be provided, wherein each source electrode 200 is independently controlled with respect to the other source electrodes 200. In this manner, the delivery system 100 may be manipulated to target various sites for delivery of the cargo 60, as shown in FIG. 5, illustrating the source electrodes 200 disposed within a tissue lumen 50. That is, by allowing independent control over parameters for iontophoretic delivery such as current, voltage and time, variable delivery zones may be created at distinct sites within the same tissue lumen. In addition, the source electrodes 200 may terminate at various lengths to further provide control over deliver of the cargo to the target site(s). Furthermore, in some instances, the plurality of source electrodes 200 may have the insulating members 250 disposed therebetween and thereabout to also specifically designate delivery regions 260 for delivery of the cargo 60 to the target site(s). According to an alternative embodiment, the source electrodes may be disposed within the electrode deployment device 150, such as, for example, a catheter device 350, as illustrated in FIG. 6. The catheter device 350 may be comprised of a perforated polymer sheath 352. That is, the catheter device 350 may have a plurality of perforations 354 defined thereby such that the cargo 60 may exit the catheter device 350. In one particular embodiment, the source electrodes 200 terminate at different lengths and may be independently powered such that the probes are capable of being variably controlled. The source electrodes 200 may include the insulating members 250 disposed about and between the source electrodes 200 so as to form cargo delivery zones substantially aligned with the perforations 354 of the catheter device 350. In this regard, the cargo 60 may be fed through the catheter device 350 proximate to the target site at the terminal portion of the catheter device 350, where the cargo 60 may be drawn therefrom due to the electrical field applied across the source electrode 200 and the counter electrode.

Referring to FIG. 7, in some instances, the source electrode 200 (and/or the counter electrode) may be encapsulated in a gelatinous solid, such as, for example, a soft polymer matrix 280, that prevents injury from the insertion and extraction of the source electrode 200 (and/or the counter electrode). The polymer matrix 280 may also serve as a cargo reservoir 300 from where the therapeutic agent(s) may be mobilized. That is, the cargo 60 may be incorporated in the polymer matrix 280 such that, upon actuation of the electric field, the cargo 60 may diffuse out of the polymer matrix 280 and be delivered to the target site. FIGS. 8A and 8B illustrate the source electrode 200 having one or more insulating members 250 disposed thereabout such that both the source electrode 200 and the insulating members 250 are encapsulated in the polymer matrix 280. FIG. 8A shows a single insulating member 250 disposed longitudinally along the source electrode 200 such that the cargo 60 may be directed toward the target site. FIG. 8B shows a plurality of insulating members 250 engaged with the source electrode 200 such that various cargo delivery regions or zones are defined for delivering the cargo 60 to specific areas of the target site. In this regard, there may be a region or regions 290 of depleted cargo within the polymer matrix 280 and a normal region or regions 295 at some duration after actuation of the electric field to drive the cargo 60 toward the target site.

FIG. 9 illustrates an embodiment of the delivery system 100 similar to that of FIG. 5, wherein a plurality of independently controlled source electrodes 200 may be provided such that various target sites and/or regions may be targeted for delivery. As described previously, the length at which the source electrodes 200 terminate may alter and the insulating members 250 may be provided to further control delivery of the cargo 60. In some instances, as shown in FIG. 9, the source electrodes 200 and insulating members 250 may be encapsulated in a gelatinous solid such as, for example, the polymer matrix 280 carrying the cargo 60 therewith. In this manner, there may be a region 290 of depleted cargo within the polymer matrix 280 and a normal region 295 at some duration after actuation of the electric field to drive the cargo 60 toward the target site.

In one embodiment, as illustrated in FIGS. 10 and 11, a catheter device, such as, for example, a balloon catheter 400 having a pair of expandable members 402 may be used to deliver the cargo 60 to the target site. The source electrode 200 may be serially disposed between the pair of expandable members 402, which are configured to occlude a target site. In this regard, the expandable members 402 may be used to enclose or occlude an intraluminal area before and/or after the source electrode 200, to limit the delivery of the cargo (e.g., therapeutic agent) to the area of interest. That is, the expandable members 402 may be in a relaxed state (FIG. 10) during positioning of the catheter and/or source electrode 200 proximate to the target site. Thereafter, the expandable members 402 may be inflated to an expanded state (FIG. 11) so as to contact a duct or other passageway 410 to enclose the target site such that the cargo delivery is isolated to the target site, thereby limiting exposure of healthy tissue to the cargo materials. In one embodiment, the delivery system 100 may include inflatable members 402, as schematically shown in FIGS. 10 and 11, which illustrate the distal end of the catheter device 400 with the expandable member 402 in its relaxed and inflated/expanded states, respectively. The catheter device 400 may include a guide wire for positioning the catheter device 400 near the target site. The term catheter as used in the present application is intended to broadly include any medical device designed for insertion into a body passageway to permit injection or withdrawal of fluids, to keep a passage open or for any other purpose. In other instances, an area to be treated may be occluded by blocking or damming an area using a balloon or a polymer cap or fibers (not shown).

Figure 12:
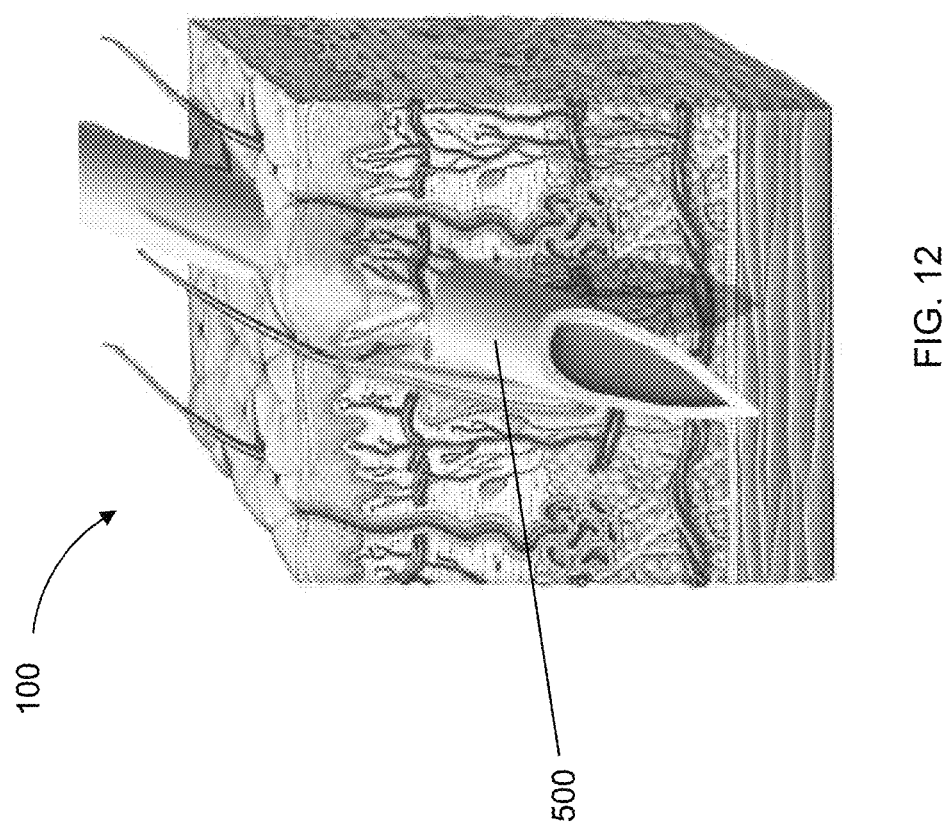
FIG. 12 is a partial view of a delivery system having a source electrode comprising a hollow tube needle member configured to deliver a cargo to a target site of internal body tissue, according to one embodiment of the present disclosure.
Figure 13:
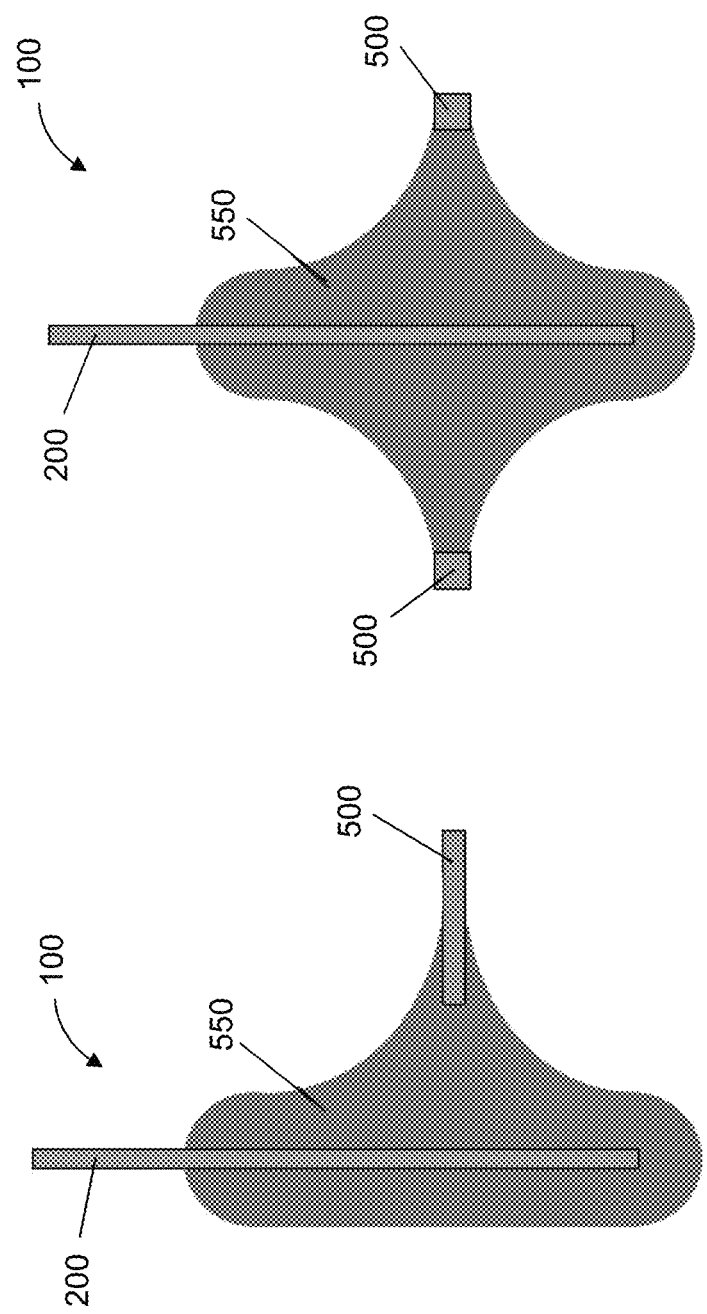
FIGS. 13A and 13B are partial views of a delivery system having a counter electrode positioned at various orientations with respect to the source electrode so as to target delivery of a cargo to a target site to predetermined in vivo locations.

With reference to FIG. 12, placement of the cargo, such as the PRINT nanoparticles, may be achieved by using a hollow tube needle member 500 having an iontophoretic tip to facilitate distribution of the particles into the surrounding target site (tissue). In such embodiments, the needle tip may represent the source electrode 200, while the counter electrode is positioned internally or external to the body so as to create a voltage potential when a power supply is energized, as described previously with respect to iontophoretic techniques. Such a technique may be used for disease states including cancer (brain, prostate, colon, others), inflammation, damaged tissue 'rescue' situations (e.g. cardio/neuro/peripheral vascular), ocular diseases, rhinitis, and other applications. Furthermore, the hollow tube portion of the needle member 500 may serve as a reservoir for the cargo, wherein the needle member 500 may be connected to a port member (not shown) located externally such that the reservoir may be filled and/or refilled externally.

Referring to FIGS. 13A, 13B, 14, 15, and 16, one or more counter electrodes 500 may be provided with the delivery system 100, wherein the counter electrode 500 consists of a probe of opposite polarity to that of the source electrode 200 that completes the electrical circuit of the system. That is, in using embodiments of the delivery system for iontophoretically enhanced drug delivery, a separate electrode of opposite polarity to the source electrode 200 is used in order to generate the potential gradient across the artery or other body tissue. In some instances, the counter electrode 500 may be positioned internally or otherwise external to the body such as on the patient's body (usually the skin) and may be attached using any known means, such as ECG conductive jelly. That is, placement of the source electrode 200 and the counter electrode 500 may be altered to fit the tissue location and disease state to be treated. For example, the source electrode 200 and the counter electrode 500 may be placed internally, externally or one internal and one external as long as appropriate electrical connection can be made. Internally placed electrodes can be proximal or distal in relation to each other and the tissue.

In some instances, as shown in FIGS. 13A and 13B, the counter electrode 500 may be designed to maximize movement of the cargo (e.g., the therapeutic agent) towards itself and away from the source electrode 200 so as to promote distinct and varied delivery zones 550. That is, the position of the counter electrode 500 may be manipulated to exert control over targeted delivery to specific in vivo locations. For example, as shown in the configuration of FIG. 13A, the counter electrode 500 may be positioned substantially perpendicularly with respect to the source electrode 200, whereas, as shown in the configuration of FIG. 13B, the counter electrode 500 may be concentrically positioned about the source electrode 200. Such configurations of the counter electrode 500 may lead to highly directional transport or broader transport bands, as dependent on the configuration and orientation with respect to the source electrode 200.

Figure 14:
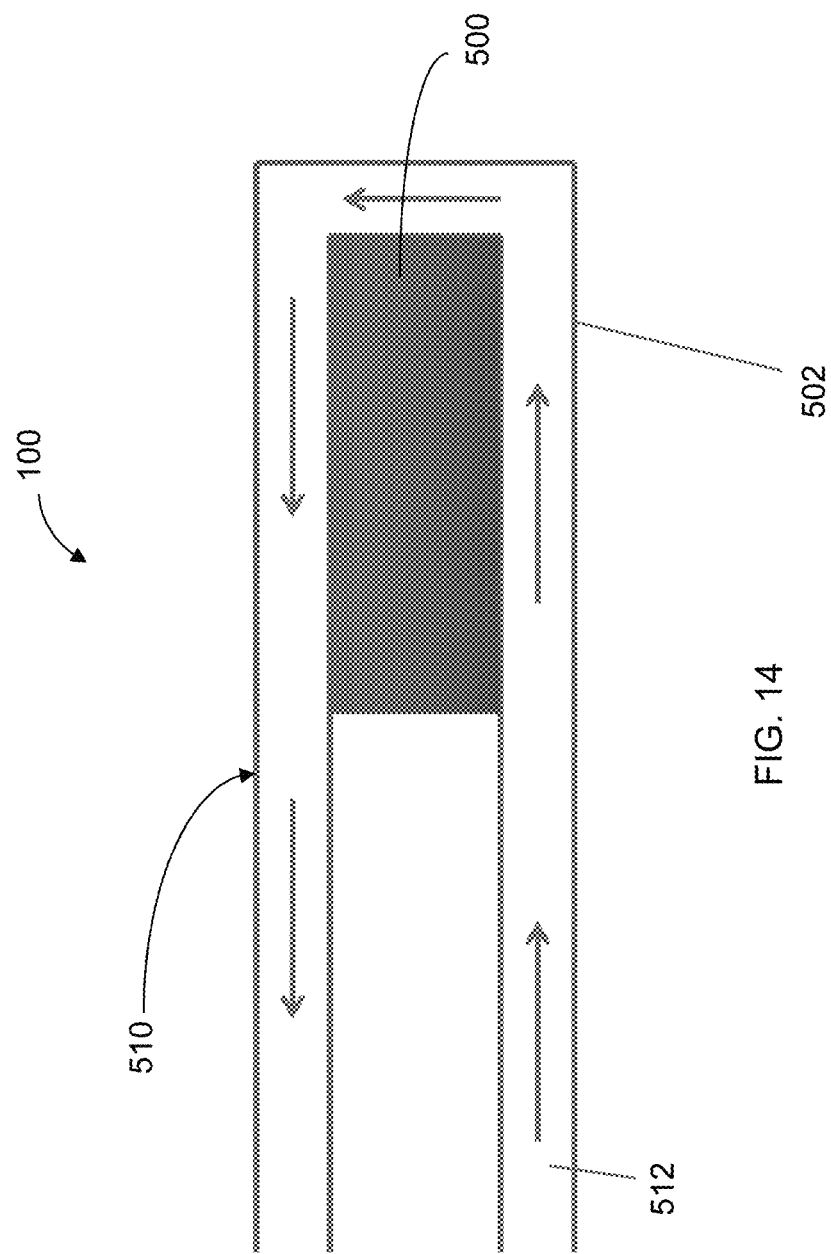
FIG. 14 is a partial view of a delivery system having a coolant device extending about a counter electrode to provide cooling thereto, the coolant device having a membrane portion disposed about the counter electrode, according to one embodiment of the present disclosure.
Figure 15:
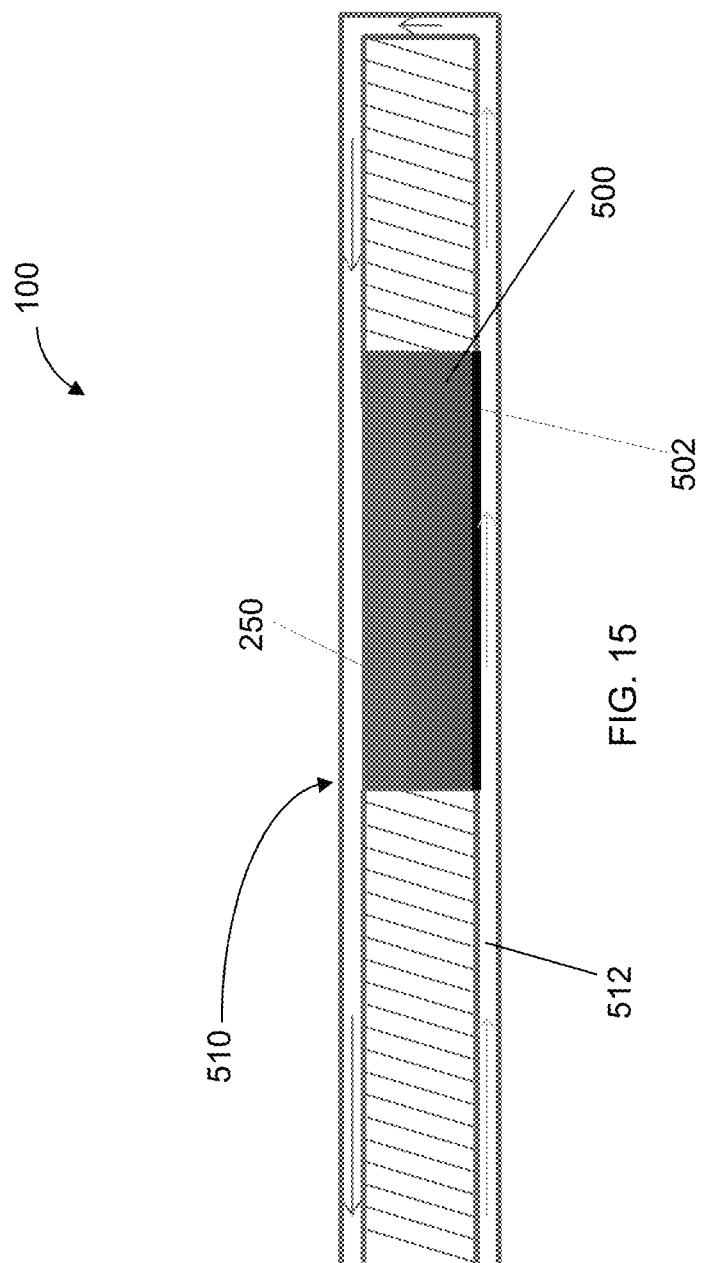
FIG. 15 is a partial view of a delivery system having a coolant device extending about a counter electrode to provide cooling thereto, wherein the counter electrode is disposed between an insulating member and a membrane portion of the coolant device, according to one embodiment of the present disclosure.
Figure 16:
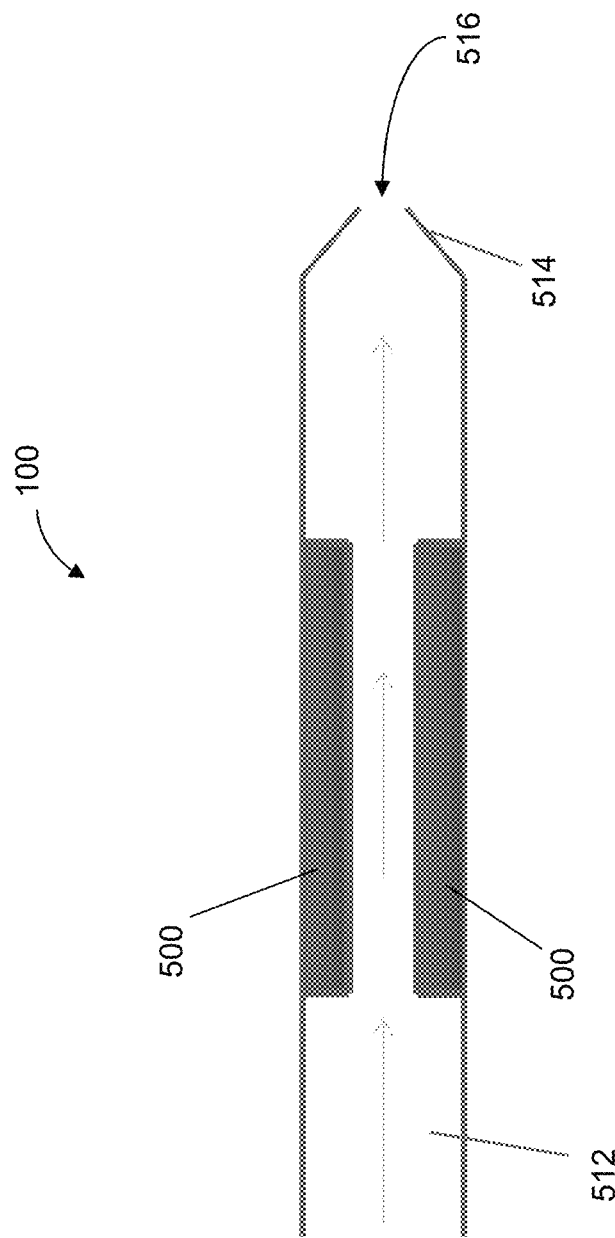
FIG. 16 is a partial view of a delivery system having a coolant device extending about a counter electrode to provide cooling thereto, the coolant device having an aperture disposed at a distal end thereof for permitting a coolant substance to exit therefrom.

In some instances, the counter electrode 500 can have an ion selective membrane portion 502 for the movement of ions to and from the counter electrode 500. In some instances, the counter electrode 500 may have a coolant device 510 for use therewith to maintain the temperature of the counter electrode 500 and to minimize the potential for tissue burns, as illustrated in FIGS. 14-16. The coolant device 510 may be configured to allow a coolant substance 512 to flow at least partially about the counter electrode 500. In this regard, the membrane portion 502 may be positioned to prevent ions that may be part of the coolant substance 512 from interfering with the cargo, drug, or material to be deposited. In some embodiments, the coolant device 510 may include a perforated tubular structure 514 defining an aperture 516 to allow for release of the coolant around the counter electrode 500, as shown in FIG. 16. The coolant substance 512 may be, for example, water, an electrolyte solution, or gel-like substance that has a high heat capacitance to maintain cooler temperatures. In addition to performing a cooling function, the coolant substance 512 may allow for a continuous flow of electrolytes for maximum ion transfer into the tissue, and maintain pH levels around the counter electrode 500. A gelatinous membrane around the counter electrode 500 may also be utilized, to minimize pH changes occurring at the conducting surface and tissue interface. In one particular embodiment, the counter electrode 500 may be disposed between the insulator member 250 and the membrane portion 502 so as to improve delivery control of the cargo to the target site.

Embodiments of the delivery system may further comprise a reservoir (see, for example, FIGS. 1, 6-9, 12, and 17-20) configured to store or otherwise carry the cargo such that the cargo may be at least partially disposed between the source electrode 200 and the counter electrode 500. In this manner, the cargo may interact with the electric field formed between the source electrode 200 and the counter electrode 500 so as to be delivered to the target site. The reservoir can be maintained as a solution, dispersion, emulsion or gelatinous solid, as previously described with respect to FIGS. 7-9. The reservoir entraps the cargo (e.g., the therapeutic agent) until the application of a physical, chemical, or electrical stimulus. In one embodiment, the cargo reservoir may be located remotely from the source electrode 200 and may be connected to the source electrode 200 via a hollow conduit. In another embodiment, the reservoir and the source electrode 200 may be designed to be a single assembly. In any instance, it may be possible to refill the reservoir, either remotely or after every use. Large, medium, and small reservoirs may be provided to allow for directionality and concentration of the cargo (e.g., the therapeutic agent) issued to the tissue of interest.

In one particular embodiment, the intraperitoneal cavity may serve as the drug reservoir. In this regard, the peritoneal cavity may be flooded with a cargo or drug of choice in an appropriate buffer. The source and counter electrodes 200, 500 may be positioned proximate to the target site of the pancreas, such as, for example, in a pancreatic duct and at an appropriate location or locations at the exterior of the pancreas near the tumor. Various arrangements of the source and counter electrodes may be implemented so that the cargo is positioned to interact with the electric field, upon actuation thereof, to drive the cargo to the target site of the pancreas. That is one, both, or neither of the electrodes may be positioned substantially within the pancreas. For example, both electrodes may be positioned exterior to the pancreas and on opposite sides thereof. In one particular example, one of the electrodes may be arranged as a wire mesh arrangement that can be positioned on and contact an exterior surface of the pancreas. A current may then be applied to drive the cargo (e.g., drug or therapeutic agent) from the peritoneal cavity to the pancreas and the site of the tumor. In another instance, the reservoir may be implanted in the intraperitoneal cavity such that the reservoir is provided remotely from the source electrode 200 and the counter electrode 500.

However, embodiments of the delivery system may also be used in association with other cavities of the body, wherein at least some of these cavities are internal body cavities, while others are not. For example, the cargo may be delivered to the cranial cavity (brain cancers), the oral cavity (head and neck cancers, thyroid cancers), the thoracic cavity or mediastinum (thymus cancer, esophageal cancers and heart disease), the pleural cavity (lung cancers, cystic fibrosis, pulmonary fibrosis, emphysema, adult respiratory distress syndrome (ARDS), and sarcoidosis), the abdominopelvic cavity or peritoneal cavity (pancreatic cancer, liver cancers and metastases, stomach cancer, small bowel cancer, genital warts, inflammatory bowel diseases (Crohn's disease and ulcerative colitis), renal cancers and metastases, splenic cancers, and Hodgkin's disease), and the pelvic cavity (testicular cancer, prostate cancer, ovarian cancer fallopian tube, cervical cancer, endometrial cancer, uterine cancers, Kaposi's sarcoma, colorectal cancers, and urinary bladder cancer).

Figure 17B:
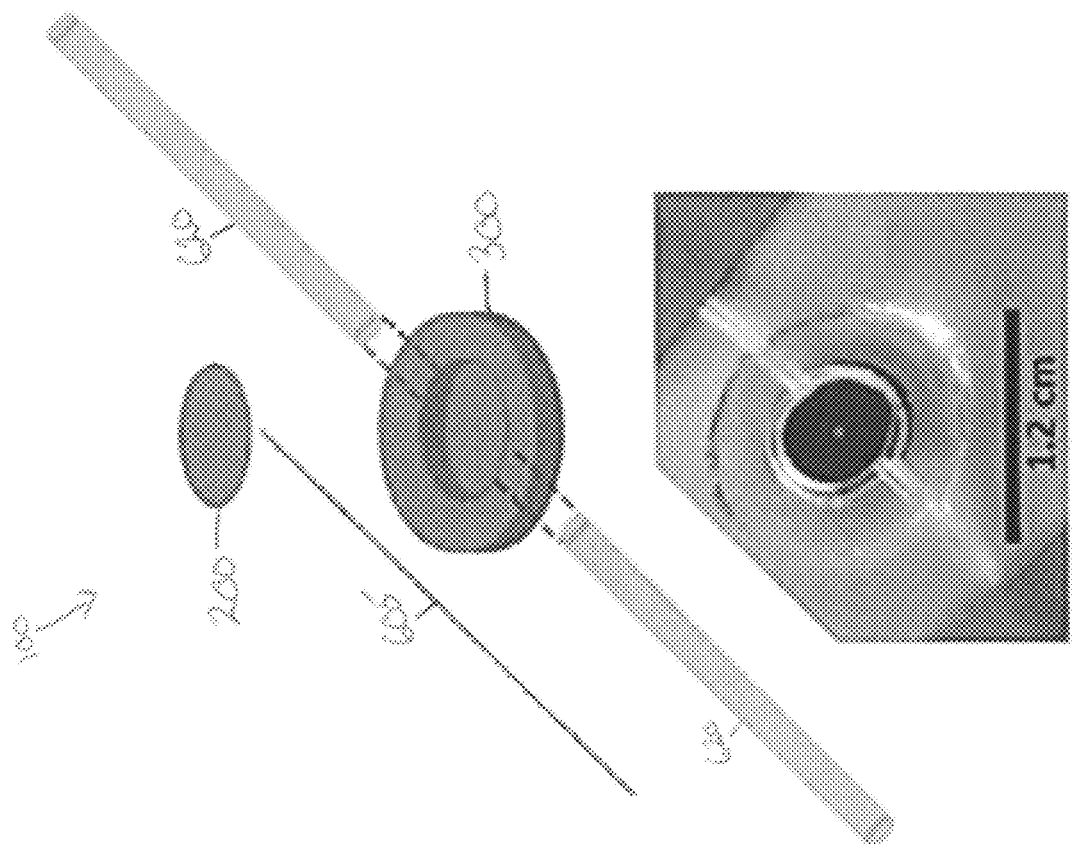
FIG. 17B shows exploded and assembled views of a delivery system according to one embodiment of the present disclosure.
Figure 17A:
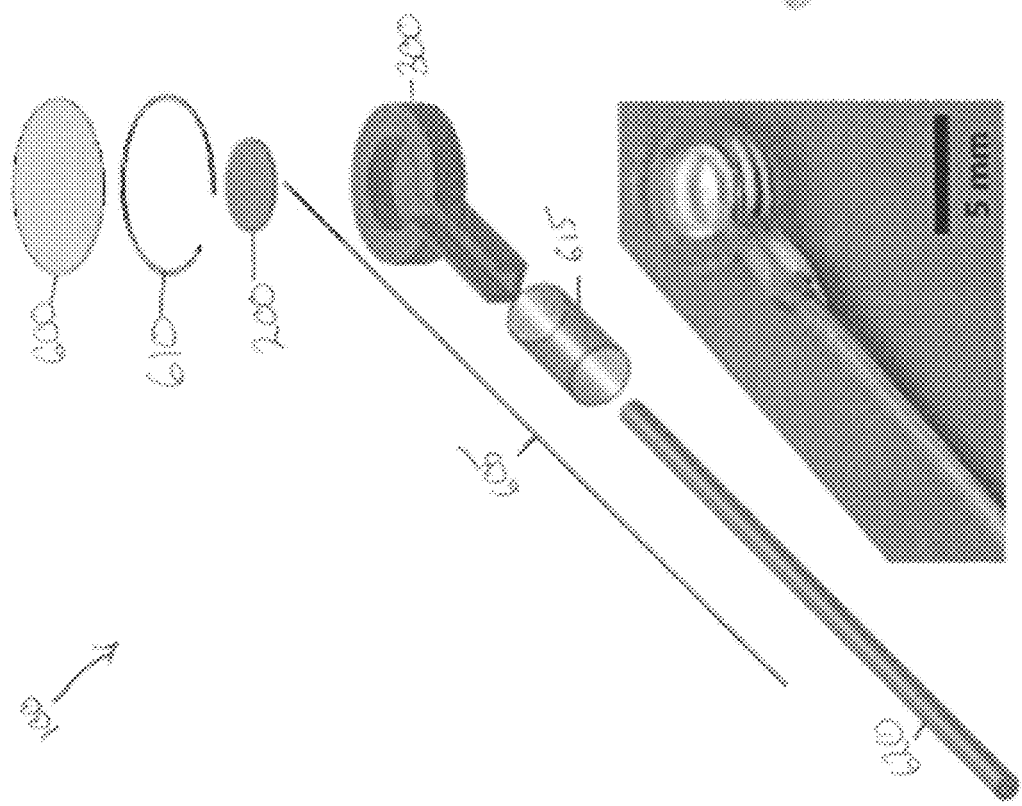
FIG. 17A shows exploded and assembled views of a delivery system according to one embodiment of the present disclosure.
Figure 18B:
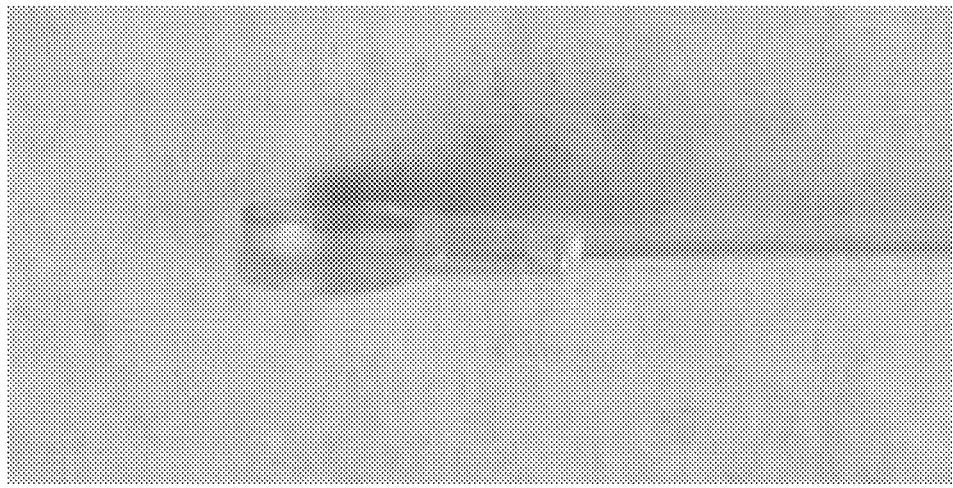
FIGS. 18A and 18B are partial views of the delivery system shown in FIG. 17A according to one embodiment of the present disclosure.
Figure 18A:
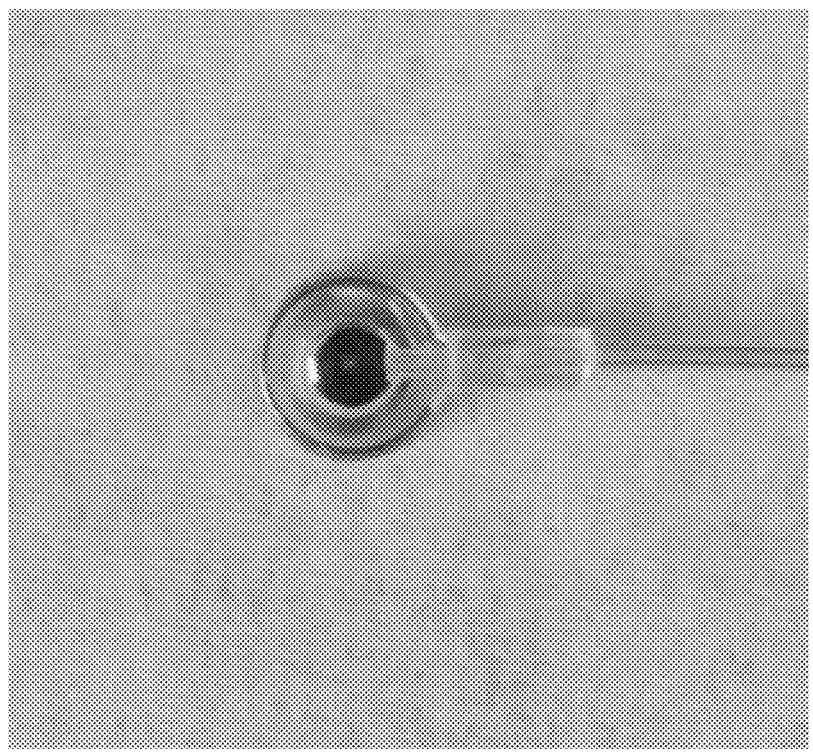
Figure 19B:
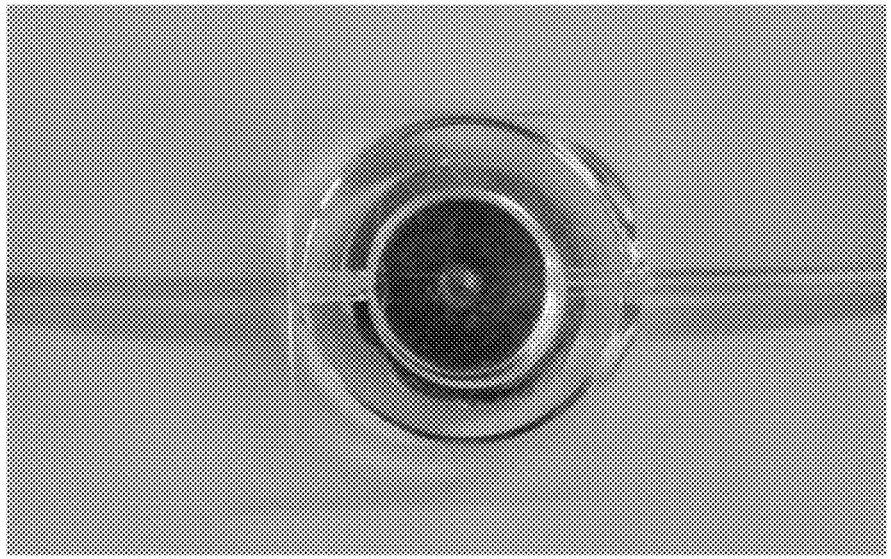
FIGS. 19A and 19B are partial views of the delivery system shown in FIG. 17B according to one embodiment of the present disclosure.
Figure 19A:
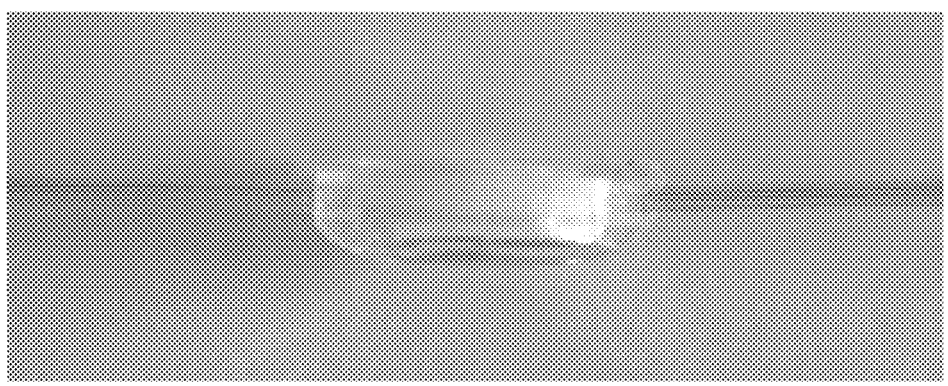

With reference to FIGS. 17-20, some embodiments of the local delivery system utilize a circular or cylindrical reservoir 300 which may have, for example, a polyurethane or polydimethylsiloxane shell. A membrane 600 may be placed over an opening in the reservoir 300 and may be, for example, a semi-permiable 14K cellulose membrane to allow the drug to be delivered to the target tissue from the reservoir and maintain pressure within the reservoir. The reservoir 300 may surround the electrode 200, which may be in direct contact with a cargo solution, and which may have a wire 605 to conduct electricity to the electrode 200. The reservoir 300 may also have an inlet and outlet for continuous cargo flow through the reservoir, for example, via a multiluminal tube 620 (shown in FIGS. 17A-19B) or via separate inlet 622 and outlet 624 lines (shown in FIG. 20). The tube may be connected to the reservoir 300 using press fit, clamps, heat shrink tubing 615, or any other attachment means. As shown in FIGS. 17-19, the conducting wire 605 may be disposed in the multiluminal tube 620. Embodiments of the drug delivery device may be implantable and/or attachable directly to the target tissue, such as the device shown in FIG. 17A. FIGS. 18A, 18B show alternative views of the device shown in FIG. 17A. In some embodiments, such as shown in FIG. 17B, a second multiluminal tube 620 may assist the efflux of the cargo. The second multiluminal tube 620 may be used on transdermal devices, such as the device shown in FIG. 17B. In some embodiments, a first and second multiluminal tube 620, as shown in FIG. 17B, may be used to ensure a constant drug concentration at the electrode by flowing drug through the device. FIGS. 19A, 19B show alternative views of the device shown in FIG. 17B. The reservoir 300 and flow system may allow for a constant drug concentration around the electrode 200 and the removal of the by-products of the redox reaction. The cellulose membrane 600 may minimize uncontrolled drug flow out of the system and may help to maintain fluid pressure within the reservoir 300 in combination with the flow system. Similarly, the counter electrode of the delivery system, as discussed herein, may also be pressurized. Pressurization may allow the drug to flow through the membrane and into the target tumor.

The delivery system may also include attachment features to secure the reservoir 300 and/or counter electrode to the target tissue. For example, the delivery device may include a metal ring 610 (shown in FIG. 17A) attached to or embedded in the surface of the reservoir 300 to allow the device to be sutured to tissue. Alternatively, the reservoir 300 may include anchor points 612 (shown in FIG. 20) for attaching the delivery device to the target tissue. Similarly, the counter electrode may have an attachment feature, such as, for example, to allow it to be secured to the target tissue so that the cargo may flow through the target tissue. These attachment features may be used in either implanted embodiments of the delivery device or in transdermal embodiments.

In order to apply a voltage potential across the source electrode 200 and the counter electrode 500, the source electrode 200 and the counter electrode 500 are in electrical communication. In this regard, the source electrode 200 and the counter electrode 500 are connected to a power source (not shown). In some instances, the power source may comprise a programmable power supply and function generator capable of generating both direct current and pulsed waveforms at various voltages and for various time intervals. The power source can generate the potential difference between the source electrode 200 and the counter electrode 500 necessary to induce electromigration and electroosmosis of the cargo (e.g., the therapeutic agent). A function generator allows for manipulation of the wave generated from the power source. Square, triangular, sawtooth, multistep wave forms may be used to drive a direct current through the source and counter electrodes 200, 500. In the embodiments described herein, the interventional drug delivery system may be connected to external controls outside of the organism being treated.

As described above, the disclosed iontophoretic techniques may take either an inside-out or an outside-in approach in driving the cargo toward the target site of tissue. That is, reverse iontophoretic techniques may be employed in all of the embodiments described hereinabove. In this regard, the source electrode may be disposed exterior to a duct, organ, tissue, or target site, while the counter electrode is positioned within a duct, lumen, organ, etc. such that the cargo is driven from outside the target site inwardly toward the target site.

Radiotherapy

Radiotherapy, or radiation therapy, may be used instead of or in addition to administering therapeutic agents to the target tissue. Radiotherapy may apply high-energy radiation to damage the DNA of a target group of cells and thereby control the growth of the targeted cells. During the radiotherapy, DNA may be damaged, and tumor growth inhibited, by either photons or charged particles directly or indirectly ionizing the atoms in the DNA chain. Radiotherapy is typically used to treat malignant conditions such as, for example, various types of cancer. However, radiotherapy may also have applications for non-cancerous and/or non-malignant conditions. Radiotherapy may be administered for curative, adjuvant, or palliative purposes depending on the type and severity of the condition being treated.

In order to target the desired diseased cells without causing excessive collateral damage, various therapy techniques and methods may be used. For example, radiotherapy may be administered either externally, by irradiating the treated organism from the outside, or internally, by placing a radiation source within the organism. Some methods of external radiation apply high energy photons or charged particles to irradiate the target cells. Photon radiation may generally be high energy X-rays or gamma rays in the kilovolt to megavolt ranges. Alternatively, electron beams or heavier charged particles, such as proton beams, may be used. Some types of external-beam radiation use one or more linear accelerators to direct a beam of particles at the target tissue. One embodiment of the present invention may use an external beam irradiator. In some embodiments, any type of external beam therapy may be used to treat the diseased tissue, including, but not limited to, two dimensional or three dimensional conventional radiation therapy, three dimensional conformal radiation therapy, stereotactic radiosurgery, stereotactic body radiation therapy, intensity-modulated radiation therapy, particle therapy, Auger therapy, image-guided radiation therapy, or tomotherapy.

Some embodiments of the present invention may use internal radiation treatment methods, such as brachytherapy or radioisotope therapy. Brachytherapy involves administering a small radiation source inside or near the target tissue, whereas radioisotope therapy involves administering a radioisotope into the body that is designed to collect in specific, target tissues. Some further embodiments may combine internal radiation therapy into a local cargo delivery system, such as the devices discussed herein, to apply a combination chemotherapy and/or radiosensitizer with the internal radiation treatment.

As discussed above, some types of radiotherapy, particularly sparsely ionizing radiation, have a reduced effect on solid tumors. One cause of this reduced effect may be hypoxia within the tumor, which limits the ability of the radiation to generate free radicals to damage the tumor's DNA. The effect of radiotherapy may be increased by increasing oxygen flow in the tumor and/or apply a hypoxic radiosensitizer prior to or during radiation treatment.

Combination Therapy

To overcome the abovementioned limitations of conventional drug and radiation therapies in the treatment of cancers and other diseases, the present invention utilizes a combination therapy including localized iontophoretic delivery of therapeutic agents and radiotherapy. In some embodiments, the radiotherapy and local drug therapy are administered substantially concurrently with one another, within normal treatment tolerances. In some additional or alternative embodiments, radiotherapy and local drug therapy may be administered consecutively with one another. As discussed above, the drug delivery system used in the present invention allows therapeutic agents such as, but not limited to, various cytotoxic agents, radiosensitizers, and/or other various drug treatments to be directed to and penetrate difficult-to-treat tissues while limiting the effect on non-targeted tissue. These drug delivery systems may be used transdermally or may be implanted within the body of a patient depending on the target tissue. For example, some breast cancers may be treated with a transdermal device, and some pancreatic cancers may be treated with an implanted device. The improved delivery of therapeutic agents may be combined synergistically with radiotherapy to improve the overall treatment effect of both techniques.

Local delivery may be accomplished with any of the interventional drug delivery systems discussed above. Using these interventional delivery systems allows direct, specific targeting of formerly inaccessible tissue. In some embodiments, the drug delivery systems allow for better penetration of the target tissue using iontophoretic techniques to pull the treatment into the target tissue. In some embodiments, pressurized, reservoir-based iontophoretic devices, as detailed above, may be used. Using iontophoresis, the local electrical field generated by the device can overcome the diffusion limitations of traditional, passive drug therapies and can apply high concentrations of the drugs to the target tissue. Such a delivery method may be particularly useful for target tissue having a high hydrostatic pressure, such as solid tumors. For example, due to dense stromal environments and poor vascularization, solid tumors may be perfusion limited. The drug delivery system of the present invention overcomes the difficulties of penetrating solid tumors while minimizing non-target tissue toxicity. Additionally or alternatively, the patient's skin may be perforated (e.g., by either abrasion or with microneedles) in order to further enhance the application of the drugs to the target tissue.

The interventional drug delivery system discussed herein may also enable greater dosage control in addition to improved penetration. By positioning the delivery system directly adjacent or inside the target tissue, the device may apply the therapeutic agents directly to the tissue without first being metabolized by the body, which can allow a more accurate, concentrated dose. The present invention may also maintain external control of the interventional delivery device, thus allowing better fine tuning of the applied dosage. By achieving an accurate drug dosage on the target tissue, the synergistic effects of the radiation may be maximized while minimizing systemic toxicity.

Some embodiments may use either or both of local and systemic (e.g., intravenous) delivery of therapeutic agents. Adding systemic treatment with therapeutic agents may increase the effectiveness of the treatment, but may also increase the toxicity of the treatment. In some embodiments, systemic treatment may be used to treat primary and metastic tumors and lesions. Using local treatment, either independently or together with additional systemic treatment, may reduce the toxic effect of the therapeutic agents on non-targeted tissue. For example, in some embodiments, two different drugs may be simultaneously administered iontophoretically, either with the same or different devices. In some other embodiments, one or more drugs may be administered iontophoretically while one or more additional drugs are administered systemically.

As described above, localized treatment allows the synergistic effect of the radiation to be further amplified by reducing systemic exposure to the administered drugs. In some embodiments, this may allow higher concentrations of existing drug treatments to be applied to cancerous cells or may allow treatments that were previously too toxic for systemic exposure to be applied locally for improved treatment. The localized treatment may reduce side effects of traditional routes of administration and keep the drug dosage below its Maximum Tolerated Dose to allow more effective treatment. For example, FOLFIRINOX is a promising cytotoxic combination but with only limited applicability due to its increased systemic toxicity, but localized delivery of FOLFIRINOX using the drug delivery system of the invention may facilitate treatment late-stage pancreatic cancer while minimizing systemic exposure.

In some embodiments, various types of radiation may be combined with the aforementioned local and/or systemic drug delivery techniques. For example, systemic radiation may be applied in combination with the drug treatments described herein. Additionally or alternatively, external and/or internal radiation may be applied systemically or to a targeted site in combination with the drug treatments described herein.

The combination therapy may further be enhanced by locally applying drugs that improve the efficacy of the radiation treatment. These radiosensitizers, as described herein, may improve the effects of the radiotherapy while simultaneously treating the cancerous cells themselves. As discussed above, the interventional drug delivery system of the present invention allows for higher dosages of more concentrated drugs. In some embodiments, more radiosensitizer or more effective radiosensitizers may be applied than was previously possible, thus compounding the benefit of radiotherapy by further increasing the susceptibility of the target tissue to radiation in addition to the therapeutic benefits of the locally-delivered drug itself. In some embodiments, increasing the effectiveness of radiotherapy may allow smaller doses of radiation to be used, thus reducing the harm to the patient while maintaining the therapeutic effect of the combination therapy. The combined use of locally delivered radiosensitizers and radiotherapy used in embodiments of the present invention may synergistically improve the effect on the targeted tissue beyond either of the two treatments individually.

Radiosensitizers may use a number of mechanisms of action to increase the sensitivity of target cells to ionizing radiation. Some embodiments of the present invention apply cytotoxic radiosensitizers, including chemotherapeutic agents, with the local iontophoretic delivery system in order to treat the targeted tissue while simultaneously increasing the sensitivity of the target tissue to radiotherapy. For example 1,2,4-benzotriazin-3-amine 1,4-dioxide (SR 4889) and 1,2,4-benzotriazine-7-amine 1,4-dioxide (WIN 59075), gemcitabine, the platinums (e.g., cis-diammino-platinum(II) (cisplatin), cis-diammine-1,1-cyclobutane dicarboxylato-platinum(II) (carboplatin), cis-[(1R,2R)-1,2-cyclohexanediamine-N,N'][oxalate(2-)-O,O']platinum (oxaliplatin)), the fluoropyrimidines (e.g., 5-fluorouracil, fluorodeoxyuridine) are all effective chemotherapeutic agents, which may be applied locally in embodiments of the present invention as a radiosensitizer.

As discussed above, one limitation of radiotherapy on the cells solid tumors is the hypoxic environment within the tumor, which prevents the formation of free radicals used to destroy the target cells. Oxygen, therefore, may serve as an effective radiosensitizer. Local application of oxygen-enhancing drugs may additionally or alternatively be used in the interventional drug delivery system to improve the treatment effects of the radiation. Additionally or alternatively, the combined therapy discussed herein may be used with other drug treatments that do not necessarily include a radiosensitizing component and still achieve synergistic benefits of applying both localized drug treatment and radiotherapy.

In some embodiments, external beam radiation may be used in combination with the local delivery of chemotherapies using the interventional devices disclosed herein. In some embodiments, brachytherapy may additionally or alternatively be combined with local delivery of chemotherapies. Brachytherapy techniques may synergize with the local drug delivery methods discussed herein by applying local radiation and local drug treatment to specific, targeted tissue. For example, in some embodiments, a radiation source may be positioned proximate the target tissue either simultaneous with or at a different time than the interventional drug delivery system to administer a combined treatment to the same target tissue. In some other embodiments, a radiation source may be positioned interstitially or directly within the target tissue (e.g. prostate, breast, etc.). For example, in some embodiments, the reservoir and/or anode of an interventional drug delivery system, as described herein, may have one or more radiation sources imbedded therein to simultaneously administer radiotherapy and local drug therapies. In another embodiment, a separate radiation source (e.g., brachytherapy) may be positioned within the patient near or within the target tissue and an interventional drug delivery system may also be positioned near or within the target tissue such that both localized treatments may be used synergistically.

In some embodiments, radioisotope therapy may also be administered to a patient along with the interventional drug treatments discussed herein. Additionally or alternatively, the interventional drug delivery system itself may be configured to internally administer ionizing radiation using the aforementioned iontophoretic methods to deliver radioisotopes to the target tissue.

Some embodiments of the present invention may be used as a neo-adjuvant treatment to further facilitate resection of cancerous tissue. For example, in some embodiments, the interventional drug delivery system may be used to shrink a target tumor to an operable size to allow the tumor to be removed. Additionally or alternatively, radiotherapy may be administered to reduce the tumor to a resectable size. As discussed above, the present invention may combine interventional drug delivery with radiotherapy to improve the treatment of a target tissue, which may improve resectability. Embodiments of the present invention may be applied to a tumor to allow previously impossible tumor shrinkage in order to facilitate resection of the tumor.

Many modifications and other embodiments of the invention will come to mind to one skilled in the art to which this invention pertains having the benefit of the teachings presented in the foregoing description; and it will be apparent to those skilled in the art that variations and modifications of the present invention can be made without departing from the scope or spirit of the invention. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

EXPERIMENTAL

The following examples are presented by way of illustration, not by way of limitation:

Example 1

Drug Delivery Device Development

An iontophoretic interventional drug delivery device was tested by altering several parameters of the device to determine the effect of the parameters on drug transport on several orthotopic mouse models. The experimental drug delivery device included an electrode directly connected to a gemcitabine drug solution with a polyurethane or polydimethylsiloxane reservoir surrounding the electrode and an inlet and outlet for continuous drug flow through the reservoir. The tested parameters include drug influx rate, electrode material, drug concentration, and applied current.

A drug influx of 50 µL/min or greater was found to result in the largest amount of gemcitabine delivered into tissue surrogates (2 wt % agarose gels) at 2 mA while maintaining a low voltage, as shown in FIG. 21A. Various conducting devices, including platinum, silver, and poly(3,4-ethylenedioxythiophene) (PEDOT), were evaluated as possible electrodes as shown in FIG. 21B. Of these possible materials, silver was found to be the most efficient material for drug transport into tissue surrogates; however, the electrochemical reaction at the silver anode prohibited long-term use due to a buildup of silver chloride. Platinum was chosen for long-term implanted device studies, with silver being used for short-term, non-implanted device studies. Three concentrations of gemcitabine, 40, 20, and 10 mg/mL resulted in large differences in drug transport with 40 mg/mL producing the highest and 10 mg/mL producing the lowest concentration transported using 2 mA of current for 10 minutes, as shown in FIG. 21D. Additionally, 2 mA of current resulted in a 1.44-fold greater drug transport than a 1 mA current, as shown in FIG. 21C. FIGS. 22A and 22B show illustrations of the murine models of pancreatic and breast cancers respectively that were used for the respective gemcitabine and cisplatin studies discussed herein.

Example 2

Drug Transport in Ex Vivo PDXs

Figure 23:
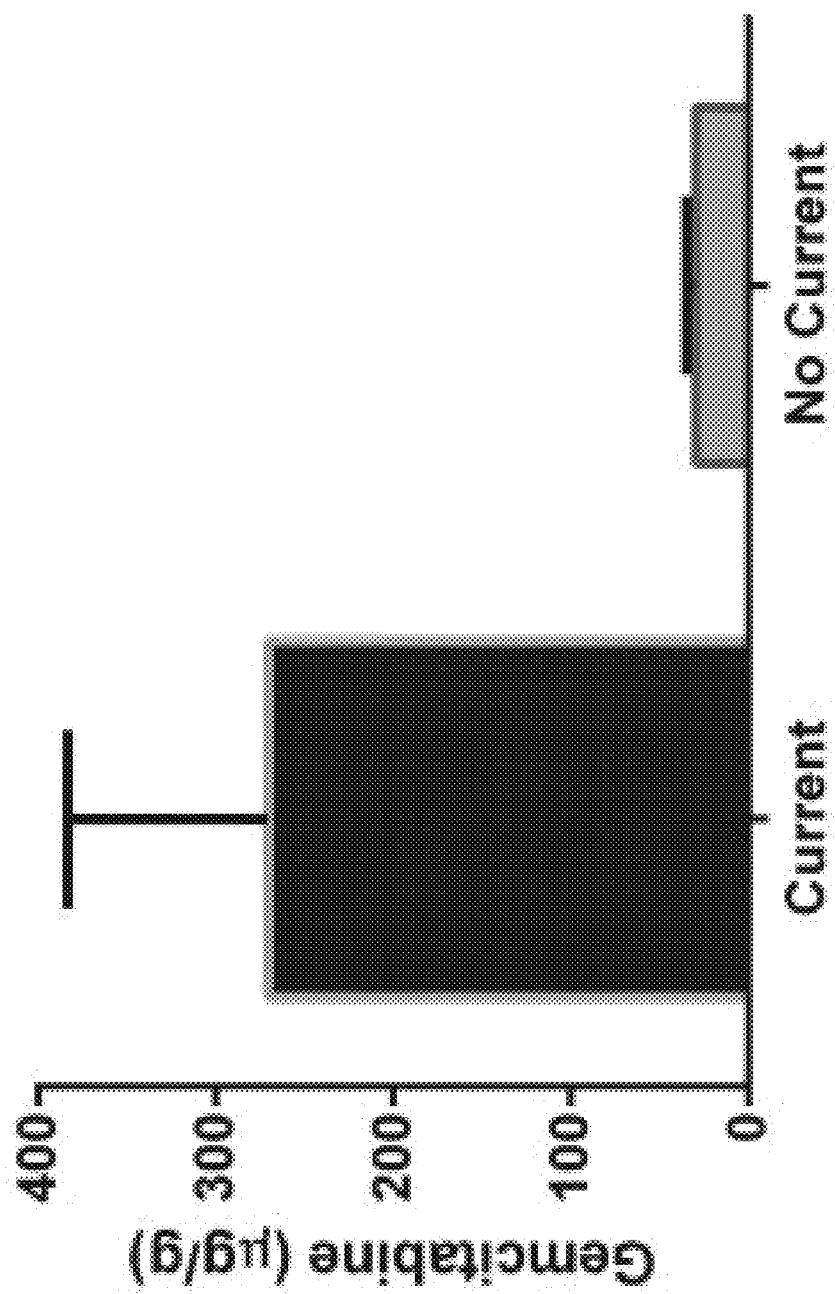
FIG. 23 illustrates experimental results of gemcitabine transport through PDX tumor tissue as a function of current for 2 mA and 0 mA according to one embodiment of the present disclosure.

Ex vivo drug transport studies were conducted using pancreatic cancer patient-derived xenografts (PDXs). Test drug transport devices were sutured onto the ex vivo PDX tumors and a counter electrode was placed on the contralateral side of the tumor. 2 or 0 mA of current was applied for 10 minutes and the tumors were subsequently snap frozen, processed, and analyzed by UV-high performance liquid chromatography (HPLC). The application of a current resulted in a 9.1-fold increase in drug transport compared to the passive diffusion control (0 mA), as shown in FIG. 23.

Example 3

Drug Transport in Ex Vivo Human Skin

Figure 24:
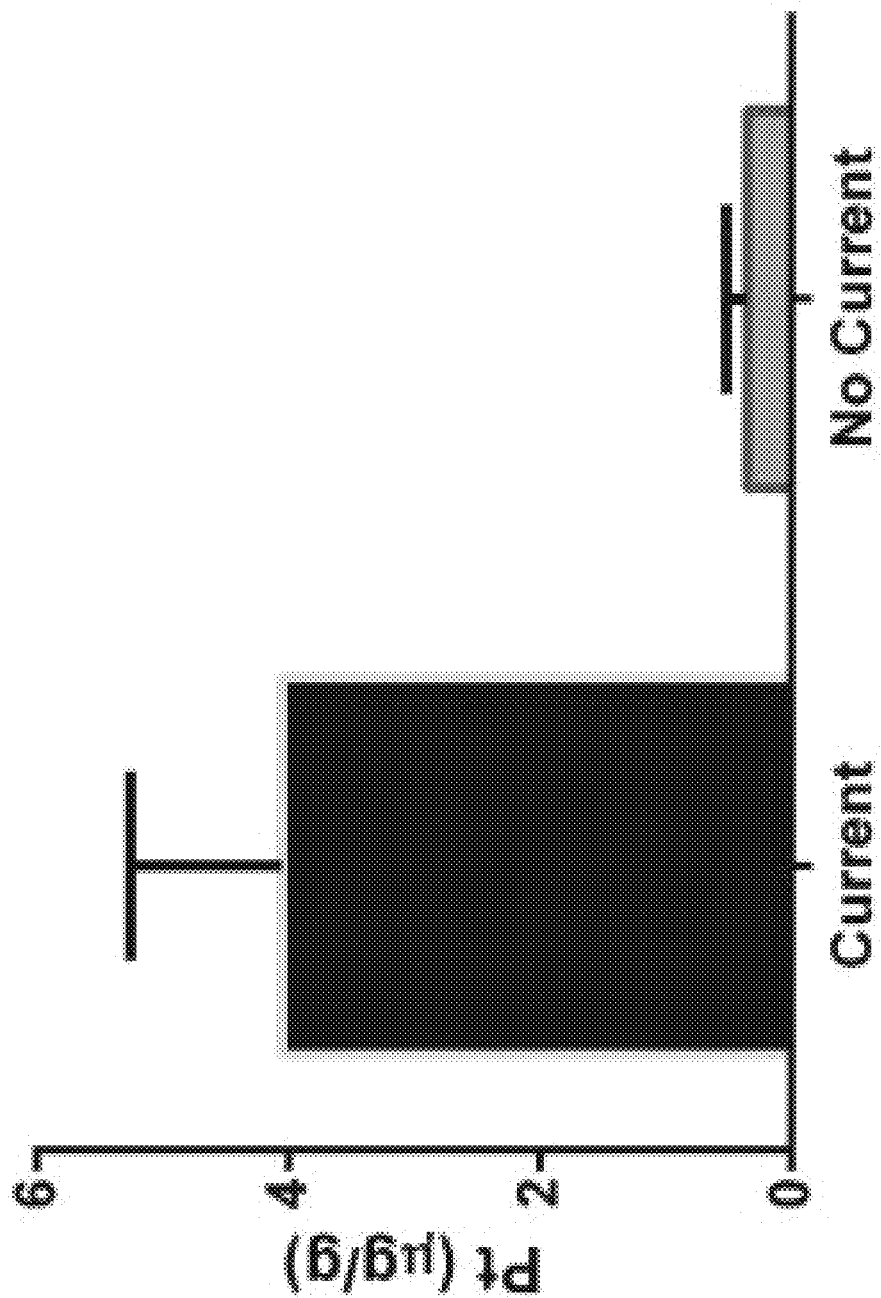
FIG. 24 illustrates experimental results of cisplatin transport through human skin as a function of current for 1 mA and 0 mA according to one embodiment of the present disclosure.
Figures 25A, 25B:
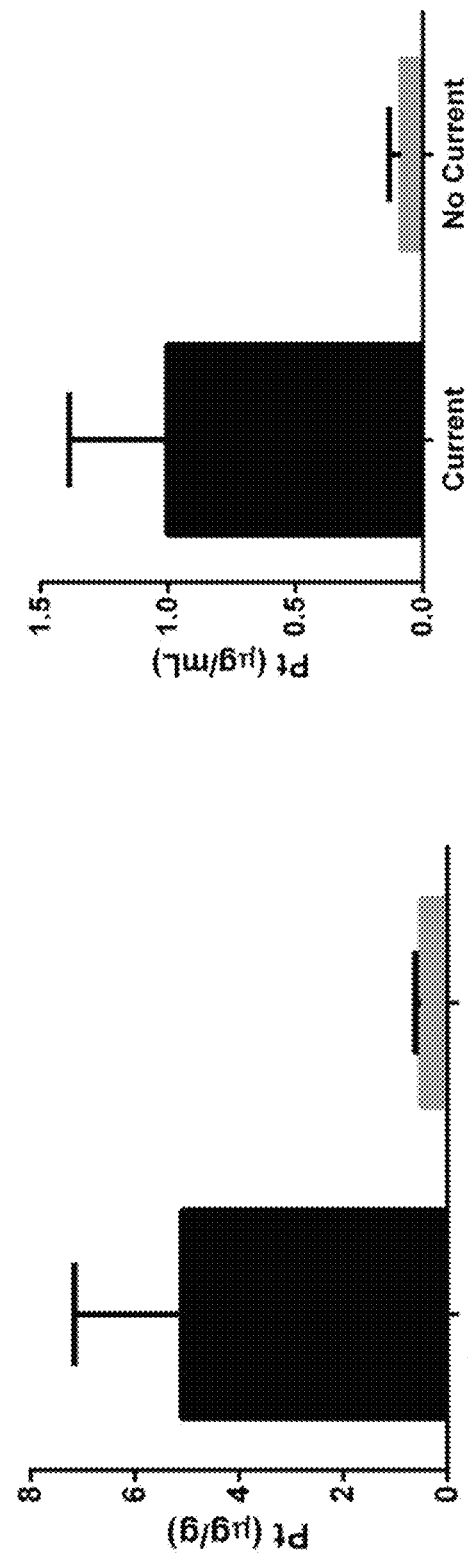
FIG. 25A illustrates experimental results of cisplatin transport into murine skin according to one embodiment of the present disclosure.
FIG. 25B illustrates experimental results of cisplatin transport through murine skin according to one embodiment of the present disclosure.

Ex vivo drug transport studies were also conducted by transporting cisplatin into ~1 mm thick human skin and were evaluated using a modified Franz diffusion cell with the test drug transport device directly above the skin instead of a donor chamber. During the testing, 1 or 0 mA of current was applied for 25 minutes, and the skin and solution were snap frozen, processed, and analyzed by inductively coupled plasma-mass spectrometry (ICP-MS). The application of a current (1 mA) resulted in an 11.4-fold increase in platinum transported into the human skin compared to passive diffusion (0 mA), as shown in FIG. 24. 24.82±18.81 ng/mL platinum was found in the receptor compartment when current was applied, but no detectable amount of platinum was detected for the passive diffusion control. A similar murine skin test revealed similar drug transport into the skin but with larger transport through the skin. FIGS. 25A and 25B show cisplatin transport into and through the murine skin respectively.

Example 4

PK Study of Device Gemcitabine Versus IV Gemcitabine

Figure 27B:
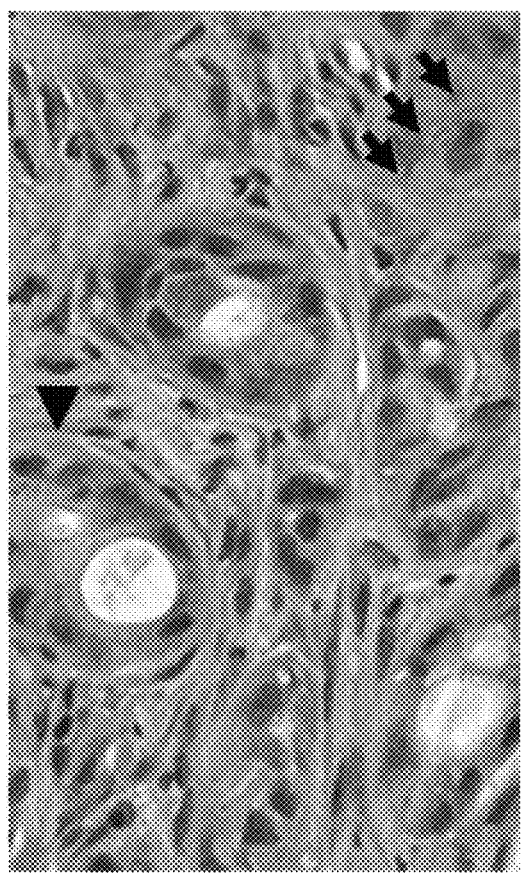
FIGS. 27A and 27B are 20× magnified views of PDX tumors showing hematoxylin and eosin staining at the time of operation and passage 2 respectively according to one embodiment of the present disclosure.
Figure 27A:
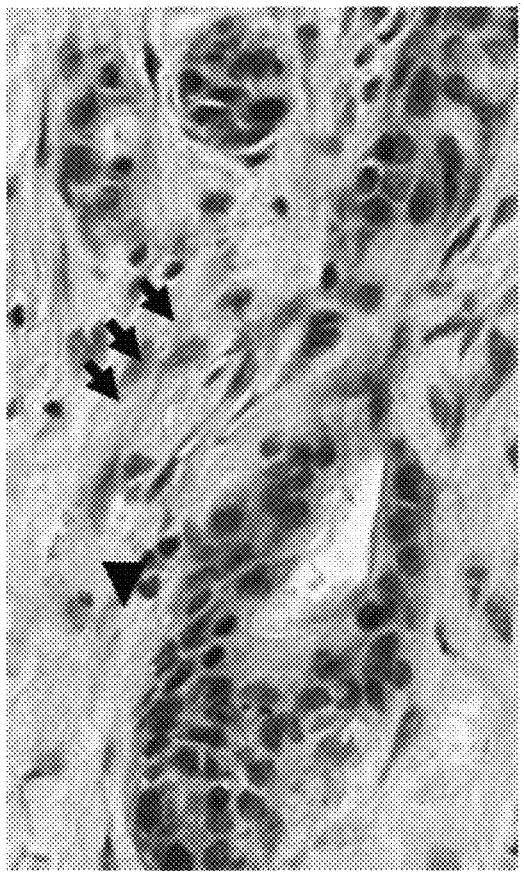
Figure 28B:
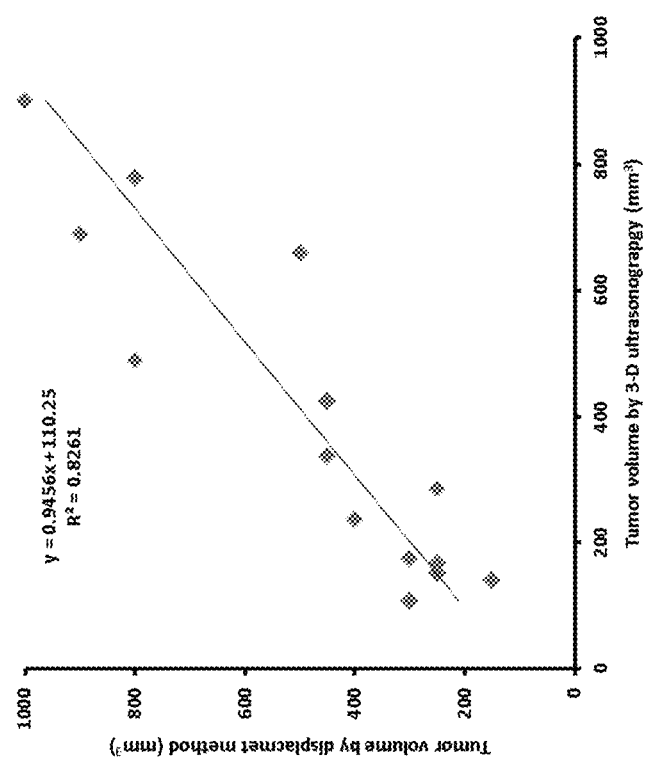
FIG. 28B illustrates experimental results of a comparison between tumor volume measurements obtained with 3D ultrasonography and with displacement according to one embodiment of the present disclosure.
Figure 28A:
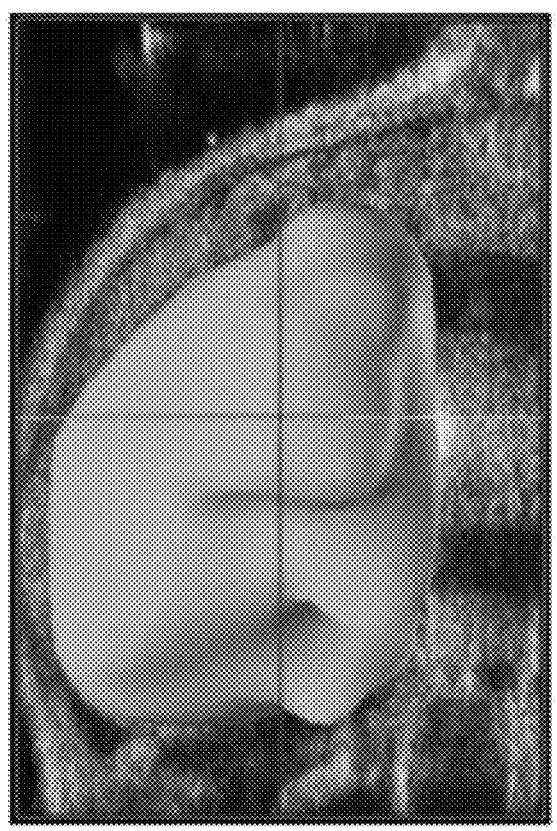
FIG. 28A is a 3D high-resolution ultrasound of a tumor according to one embodiment of the present disclosure.

Orthotopic PDX models of pancreatic cancer were used to characterize iontophoretic delivery of gemcitabine with respect to pharmacokinetics (PK). In each of the orthotopic PDX models, devices were surgically implanted when the tumor reached a median size of 200 mm$^3$, as determined by high resolution 3D ultrasound that correlated well with volume displacement. (FIG. 28A shows 3D high-resolution ultrasound and FIG. 28B shows a comparison of 3D ultrasound with traditional displacement methods of measuring volume) The mice were allowed to recover for a week after device implantation, a single treatment was administered one week post-implantation, and tumors were harvested at designated time points. FIGS. 27A, 27B shows that the PDX tumors retain heterogeneity of the original tumors and their original histological characteristics. FIG. 27A shows hematoxylin and eosin staining of a pancreatic tumor at the time of operation and FIG. 27B shows the same patient tumor at passage 2, with the arrowheads indicating the tumors and the arrows indicating the surrounding stroma.

Figure 26:
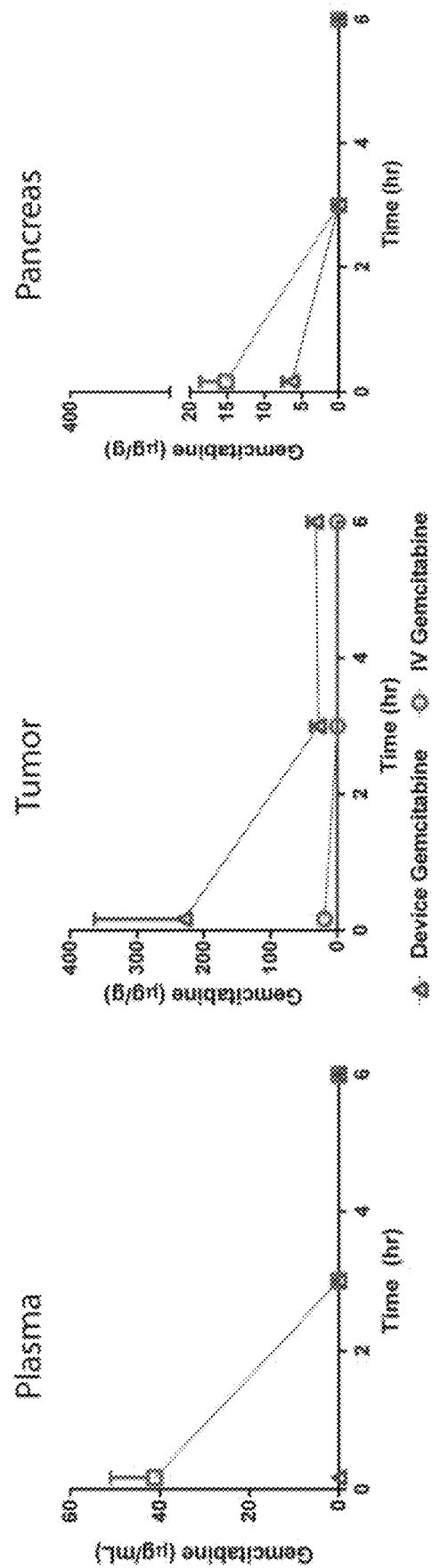
FIG. 26 illustrates experimental results of gemcitabine delivered into a PDX model of pancreatic cancer.

In the present example, IV delivery of gemcitabine was compared to local iontophoretic delivery of gemcitabine. For IV delivery of gemcitabine, the maximum tolerated dose of 80 mg/kg was chosen with the resulting plasma exposure, as measured by the area under the concentration vs. time curve (AUC), being 65.24 hr*µg/mL and there being no detectable gemcitabine in the plasma of the device arm. Gemcitabine tumor AUC was 348.07 hr*µg/mL for iontophoretic delivery and 30.78 hr*µg/mL for IV delivery. Using iontophoretic delivery, gemcitabine was detected 4.7 mm away from the devices at 0 hours and 3 mm at 3 and 6 hours. For IV gemcitabine-treated mice, gemcitabine was detected throughout the entirety of the tumor at significantly lower drug concentrations. FIG. 26 shows plasma, tumor, and pancreas plots of the PK of gemcitabine delivered iontophoretically into the PDX model of pancreatic cancer.

Figure 29B:
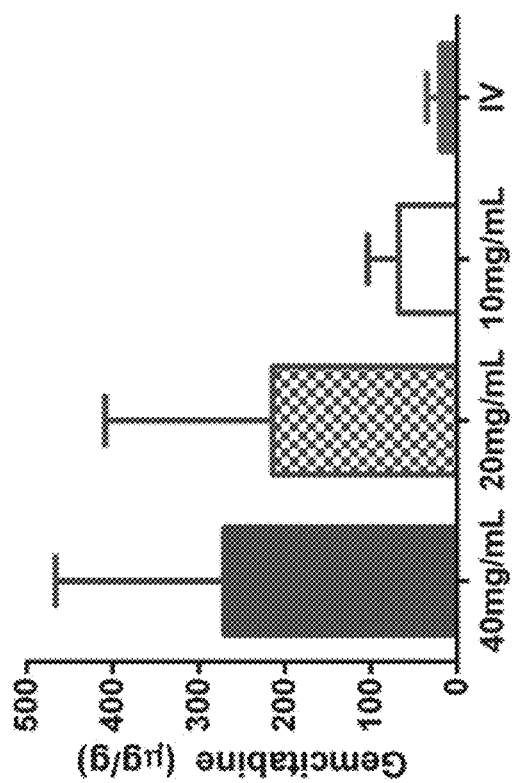
FIG. 29B illustrates experimental results of gemcitabine concentrations delivered into plasma according to one embodiment of the present disclosure.
Figure 29A:
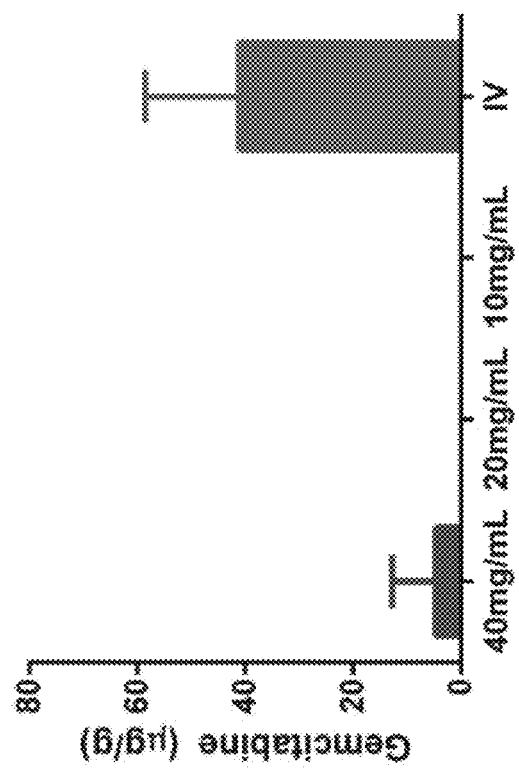
FIG. 29A illustrates experimental results of gemcitabine concentrations delivered into a tumor according to one embodiment of the present disclosure.
Figure 29C:
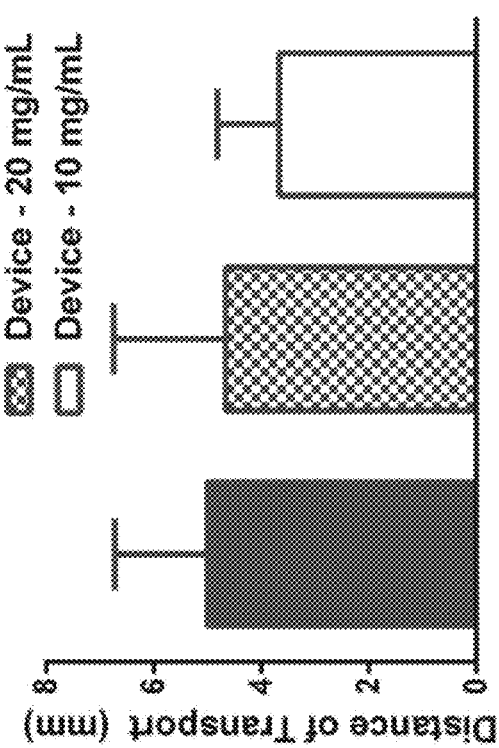
FIG. 29C illustrates experimental results of gemcitabine transport distances in PDX tumors directly after therapy according to one embodiment of the present disclosure.

Additionally, single time point PK of the device delivery of 40 or 10 mg/mL gemcitabine (n=3, each) was evaluated directly after treatment revealing 11.6-fold and 2.4-fold higher amounts of gemcitabine in the tumor and significantly lower plasma exposure compared to IV delivery. FIGS. 29A, 29B show the concentrations of gemcitabine delivered to the plasma (FIG. 29A) and tumor (FIG. 29B) respectively. The average distances that gemcitabine was detected in the tumors in the direction away from the devices was 5.0 mm for 40 mg/mL gemcitabine and 3.7 mm for 10 mg/mL gemcitabine, as shown in FIG. 29C. Drug accumulation in the tumor and distance of drug transport was dependent upon the influx gemcitabine concentration, which correlated with the in vitro drug transport results. In these examples, device delivery results in greater amounts of drug delivered to the tumor and significantly lower plasma exposure.

Example 5

Biodistribution Using Device Delivery and/or IV Delivery of Cisplatin

Figure 30:
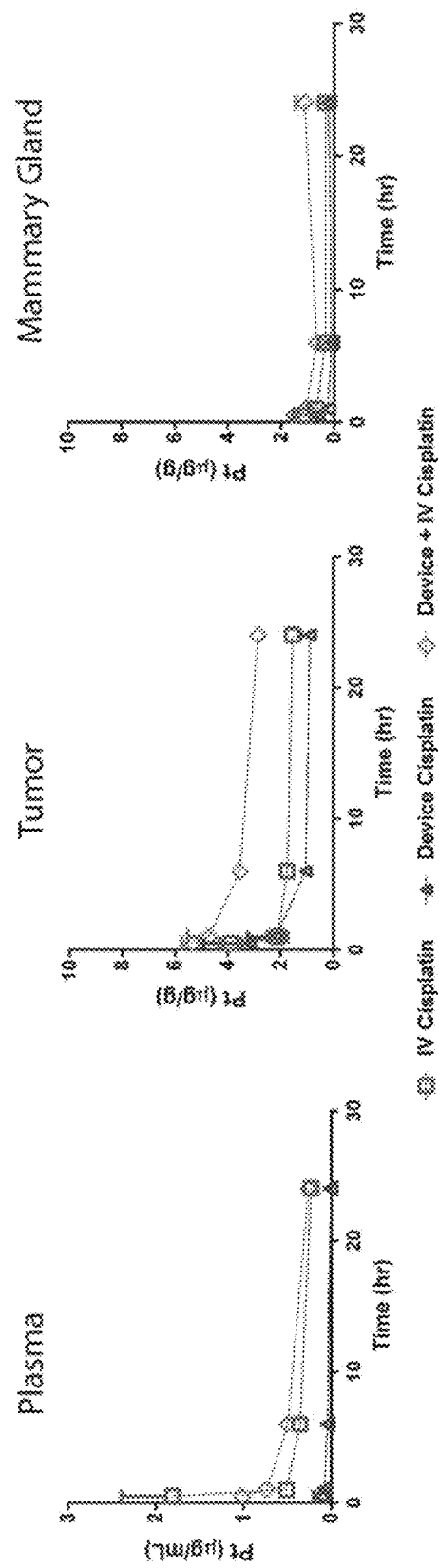
FIG. 30 illustrates experimental results of cisplatin delivered into a SUM149 cell orthotopic xenograft of breast cancer according to one embodiment of the present disclosure.

Device delivery of cisplatin was evaluated using an orthotopic SUM149 cell xenograft model of breast cancer. In addition to studying iontophoretic delivery as compared to IV delivery of the cisplatin, concurrent device and IV delivery was added as an arm of the study based upon the low systemic exposure of cisplatin. In the study, a single treatment was administered after adhesion of the device to the skin above the tumor. FIG. 30 shows plasma, tumor, and mammary gland plots of the PK of cisplatin delivered iontophoretically into the SUM149 cell orthotopic xenograft of breast cancer. Platinum plasma exposure and tumor exposure, as measured by AUC, are shown in the following table:

|  | Platinum Plasma Exposure (hr * µg/mL) | Platinum Tumor Exposure (hr * µg/mL) |
| --- | --- | --- |
| Device Delivery | 1.99 | 30.20 |
| IV (5 mg/kg) Delivery | 9.91 | 42.36 |
| Device + IV (5 mg/kg) Delivery | 10.65 | 83.40 |

Figure 31:
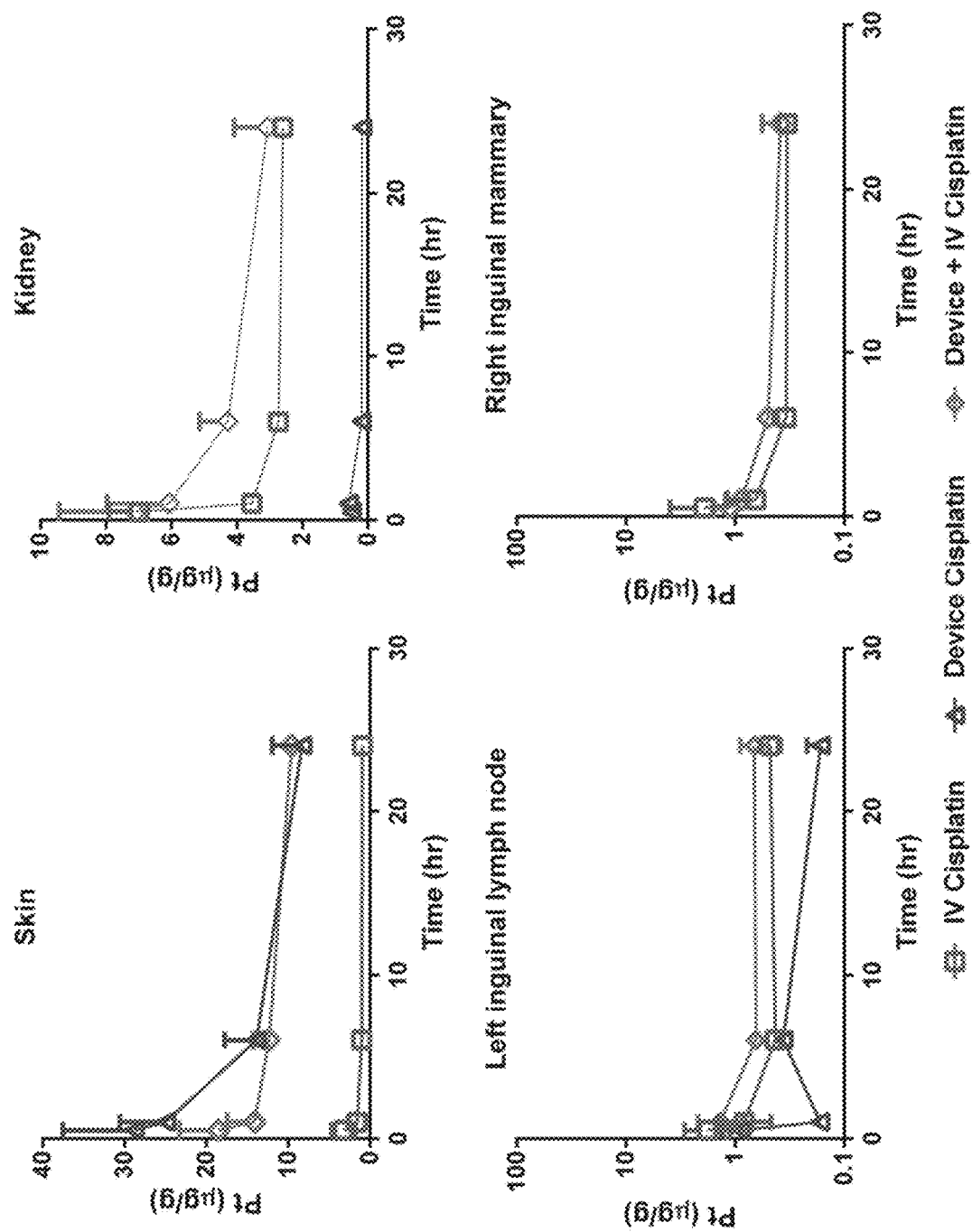
FIG. 31 illustrates experimental results of cisplatin measured at the skin, kidney, left inguinal lymph node, and right inguinal lymph node according to one embodiment of the present disclosure.

There were significant differences in cisplatin accumulation in the left inguinal mammary and kidney, skin, inguinal lymph node, and right inguinal mammary for the two different routes of cisplatin administration. FIG. 31 shows a PK of iontophoretically delivered cisplatin in the skin, kidney, right inguinal mammary gland, and left inguinal mammary gland of each animal.

Example 6

Tumor Treatment Efficacy of Gemcitabine Using Iontophoretic Devices

Iontophoretic devices were surgically implanted into orthotopic PDX tumors when their size reached ~200 mm$^3$, as determined by high resolution 3D ultrasound. Mice were treated twice a week for up to 7 weeks with device gemcitabine (20 mg/mL), device saline (0.9% NaCl), IV Gemcitabine (80 mg/kg), or IV saline. Tumor volumes were measured by volume displacement after completion of the scheduled treatment due to the interference of implanted devices with ultrasound imaging. Device gemcitabine resulted in significant tumor regression in 7 out of 7 mice, outperforming IV gemcitabine and the control arms of IV and device saline over the 52-day study, as shown in FIGS. 32A, 32B.

Mice treated with the device gemcitabine had mean log$_2$-fold change in tumor volume of −0.8 compared to a mean log$_2$-fold change in tumor volume of 1.1 for IV gemcitabine, 3.0 for IV saline, and 2.6 for device saline groups (p<0.01). Device gemcitabine was better tolerated based on greater body weight gain compared to IV gemcitabine with minimal changes in alanine transaminase and lipase. FIGS. 33A-D show the body weights for PDX mice (FIG. 33A), T11 orthotopic syngeneic mice with radiation (FIG. 33B), SUM149 orthotopic xenograft mice (FIG. 33C), and T11 orthotopic syngeneic mice (FIG. 33D). FIGS. 34A-F show an evaluation of HCT (FIG. 34A), WBC (FIG. 34B), Lipase (FIG. 34C-D), AST (FIG. 34E), and BUN (FIG. 34F) for gemcitabine treatment in an orthotopic PDX model of pancreatic cancer. Device gemcitabine resulted in tumor regression in 7/7 mice compared to no regression (0/7) in the IV gemcitabine group while maintaining low systemic exposure of gemcitabine. Histological samples from the tumors post treatment revealed a decrease in Ki-67 staining from device gemcitabine-treated mice compared with tumors from mice that received IV gemcitabine, IV saline, or device saline.

Example 7

Tumor Treatment Efficacy of Cisplatin Using Iontophoretic Devices

Iontophoretic delivery of cisplatin in was tested in both SUM149 cell xenograft and T11 syngeneic orthotopic breast cancer models. For both models, the efficacies of device cisplatin, IV cisplatin, device+IV cisplatin, device saline, and IV saline were compared.

Figure 36:
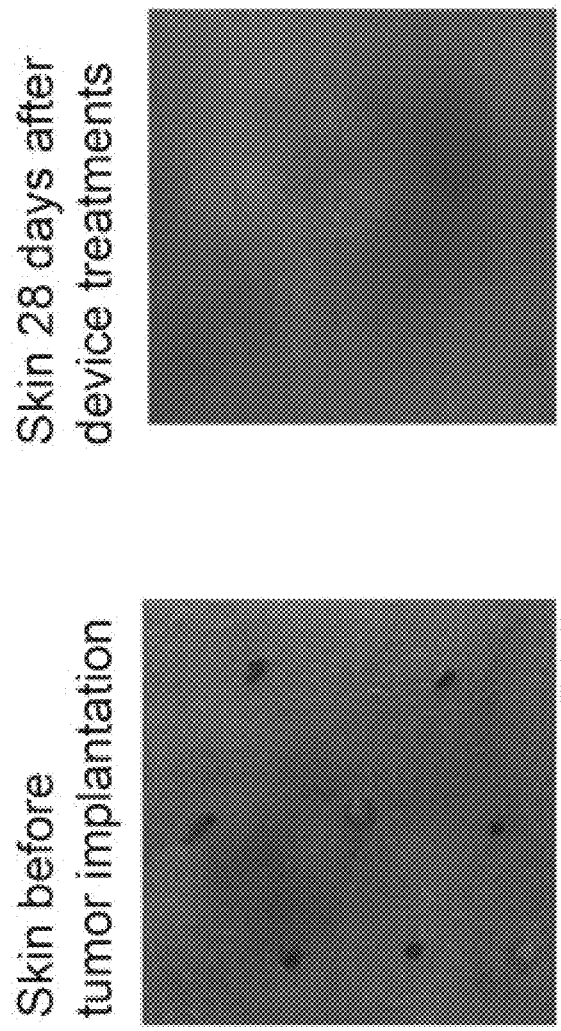
FIG. 36 depicts images of murine skin before and after four weeks of device treatment according to one embodiment of the present disclosure.

For the SUM149 xenograft model, once the tumors reached ~50 mm$^3$, the mice were treated with device cisplatin, IV cisplatin (5 mg/kg), device+IV cisplatin (5 mg/kg), device saline, or IV saline every week for four total doses, as shown in FIGS. 35A and 35B. FIG. 36 shows representative images of the murine skin before and after four weeks of device treatment. For the T11 model, mice received two doses of device cisplatin, IV cisplatin (5 mg/kg), device+IV cisplatin (5 mg/kg), device saline, or IV saline every week for two total doses beginning five days after inoculation (~20 mm$^3$), as shown in FIGS. 35C and 35D. The number of treatments varied between tumor models because of the differences in tolerability of treatments.

Device cisplatin resulted in significant tumor growth inhibition over the study, performing similarly to IV cisplatin in the SUM149 and T11 models until days 42 and 9 respectively. Device+IV cisplatin resulted in significant tumor growth inhibition, outperforming device cisplatin and IV cisplatin.

Figure 37:
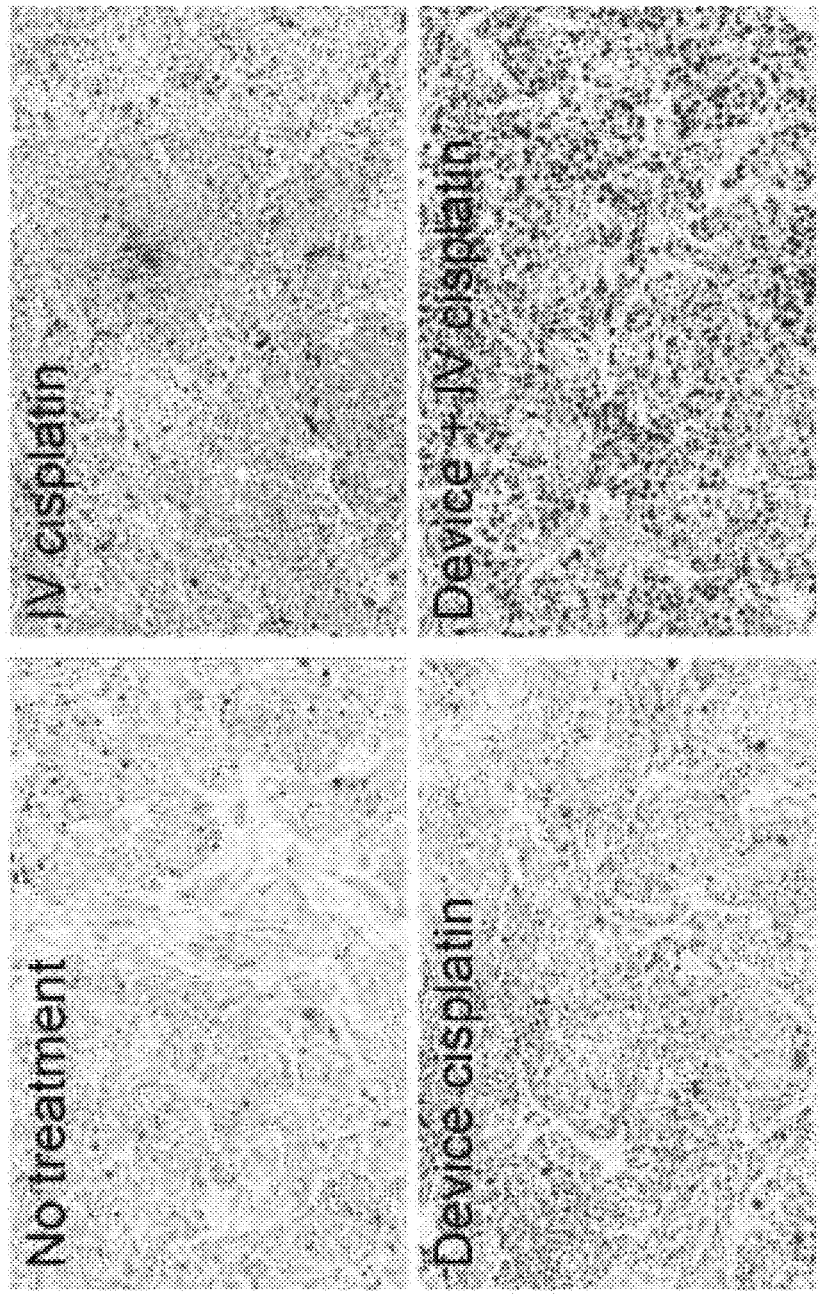
FIG. 37 depicts images of histological staining of tumors for γH2AX harvested from SUM149 cell xenograft mice 24 hours after a single treatment according to one embodiment of the present disclosure.
Figure 38:
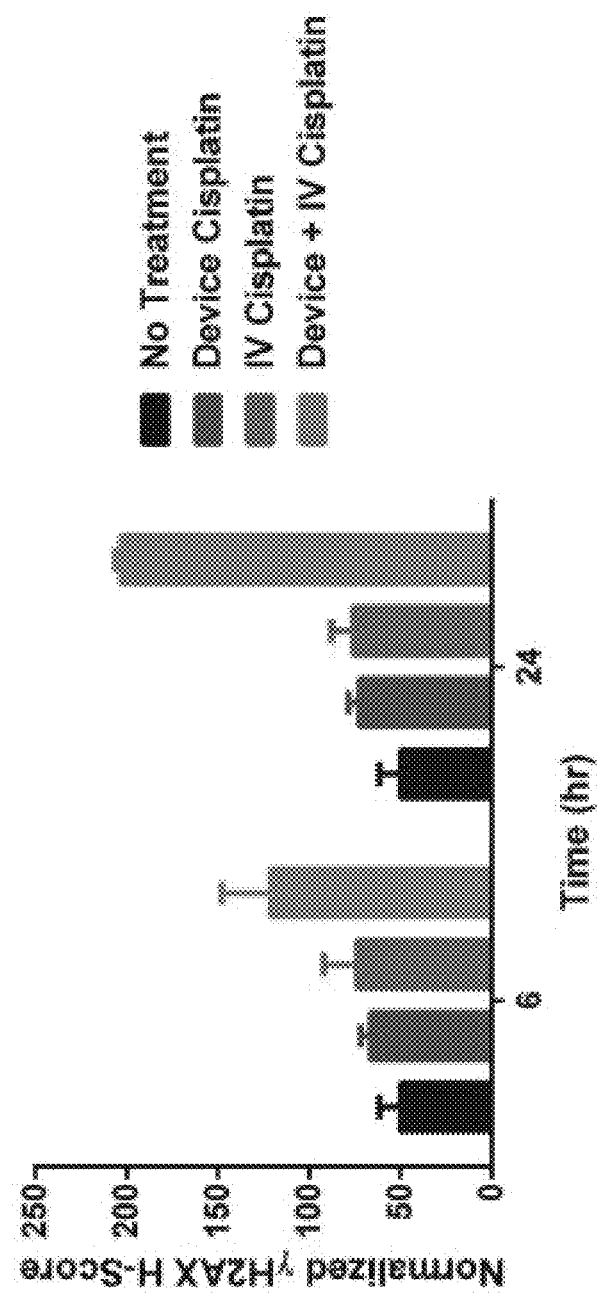
FIG. 38 illustrates experimental results of the γH2AX staining shown in FIG. 37 according to one embodiment of the present disclosure.
Figure 39:
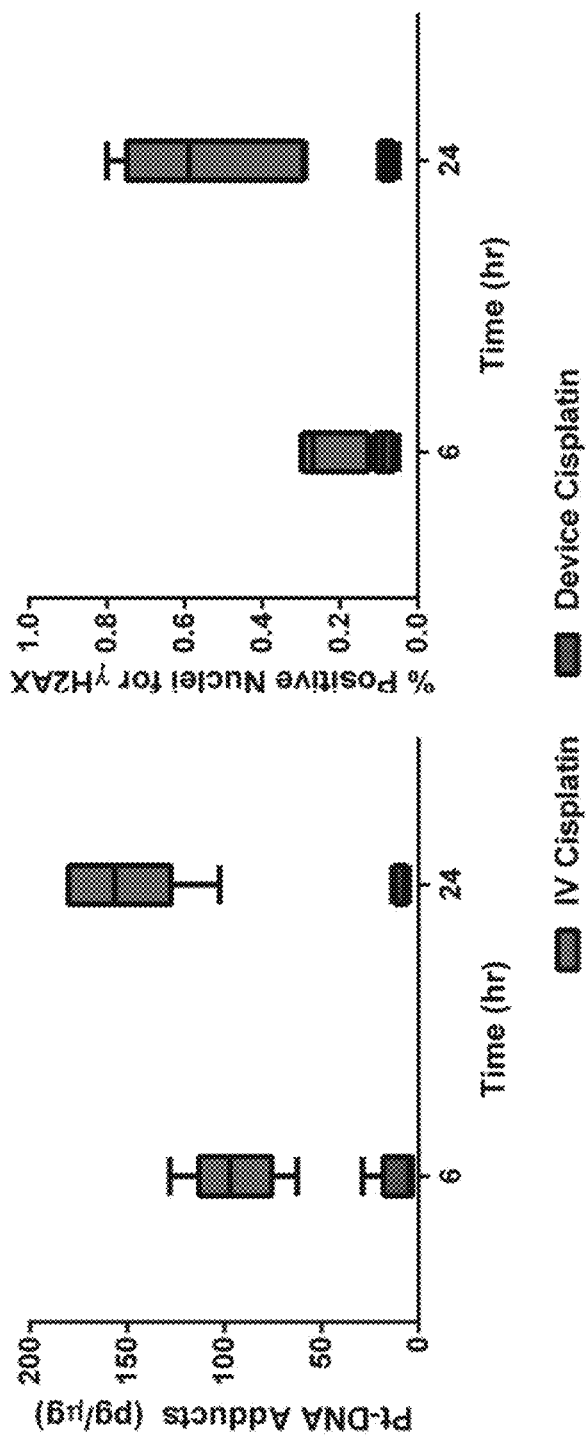
FIG. 39 illustrates experimental results of cisplatin efficacy with Platinum-DNA adducts and γH2AX staining within the kidney in a SUM149 breast cancer xenograft model according to one embodiment of the present disclosure.

The study also considered the effects of device treatment on overall survival of the orthotopic breast cancer models. Device cisplatin, IV cisplatin, and device+IV cisplatin extended the lifespan from a median of 49 days to 60, 68, and past 100 respectively, in the SUM149 model (p<0.0001). Device cisplatin, IV cisplatin, and device+IV cisplatin extended the lifespan from a median of 10 days to 20, 22, and 32 days, respectively, in the T11 model (p<0.0001). The skin of the mice after four weekly device treatments showed no scarring or deformation. Device cisplatin was better tolerated based on histological staining of the kidneys for a sensitive molecular marker of DNA damage and repair, γH2AX, compared to IV cisplatin and device+IV cisplatin, as shown in FIG. 39. In addition, histological samples from tumors post treatment revealed almost equivalent γH2AX staining from device cisplatin and IV cisplatin-treated mice and greater γH2AX staining in device+IV cisplatin-treated mice. FIG. 37 shows histological staining of tumors for γH2AX harvested from SUM149 cell xenograft mice 24 hours after a single treatment, and FIG. 38 shows quantification of γH2AX staining according to H-score as a function of treatment.

Example 8

Figure 40:
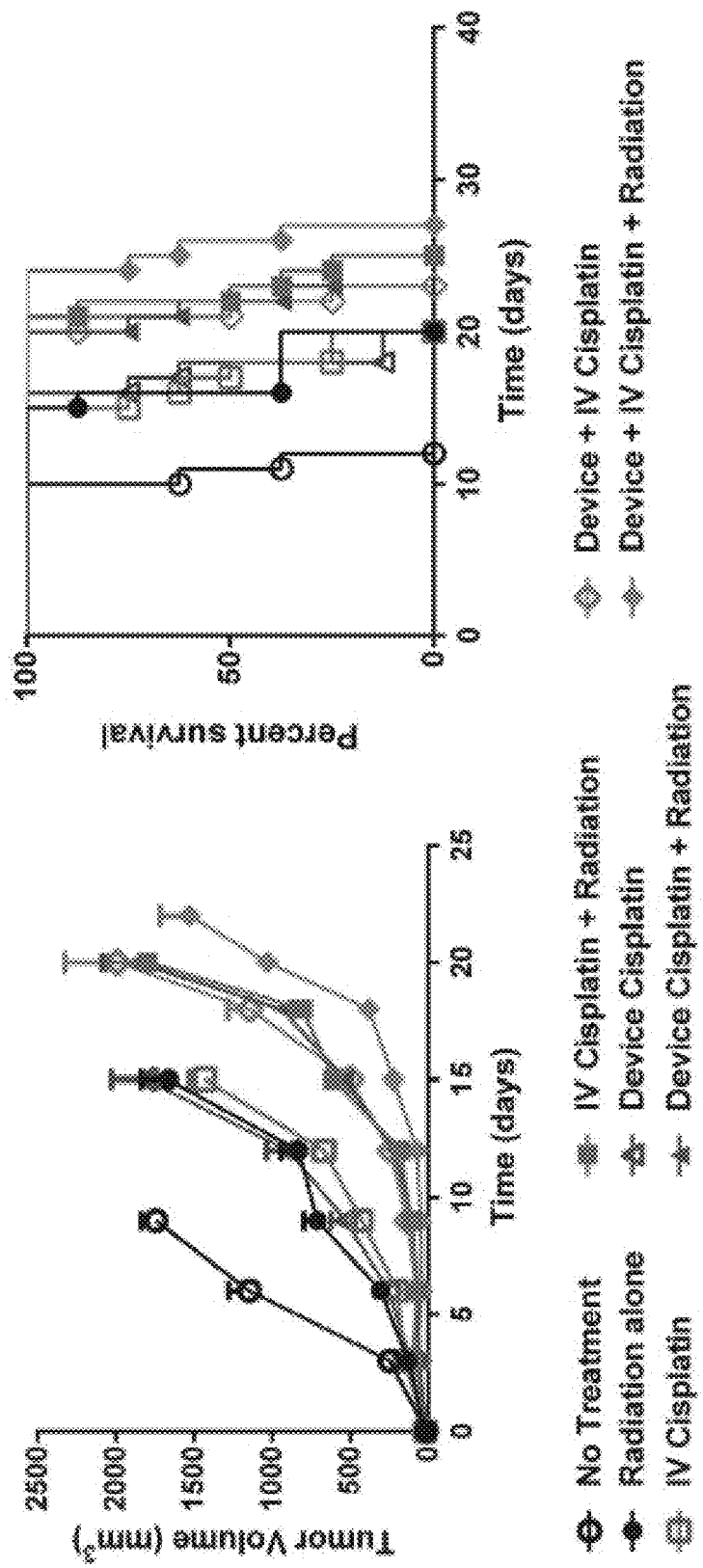
FIG. 40 illustrates experimental results of cisplatin and/or radiation treatment according to one embodiment of the present disclosure.

Combined Treatment Efficacy of Cisplatin Using Iontophoretic Devices and/or Radiation Using T11 syngeneic orthotopic breast cancer models, radiotherapy was tested as an alternative and/or additional treatment method to device and IV cisplatin to compare the therapeutic effects of the various treatments. Mice received a single dose of radiation (10 Gy), device cisplatin, device cisplatin+radiation (10 Gy), IV cisplatin (5 mg/kg), IV cisplatin+radiation (10 Gy), device+IV cisplatin (5 mg/kg), and device cisplatin+IV cisplatin (5 mg/kg)+radiation (10 Gy) five days after inoculation (~20 mm$^3$). There were two major cohorts of response: mice treated with a single dose of radiation, device cisplatin, and IV cisplatin had similar tumor growth rates and survival; mice treated with a single dose of device cisplatin+radiation, IV cisplatin+radiation, and device+IV cisplatin had similar delay in tumor growth and survival, indicating that the addition of radiotherapy improved tumor growth inhibition. Device+IV cisplatin+radiation outperformed all other treatment groups in tumor growth inhibition and survival, but more generally, the addition of radiation to device cisplatin, IV cisplatin, and device+IV cisplatin significantly improved survival (p<0.0001). The results of these studies are shown in FIG. 40.

Example 9

PK Study in Large Animals (Dogs)

Figure 41:
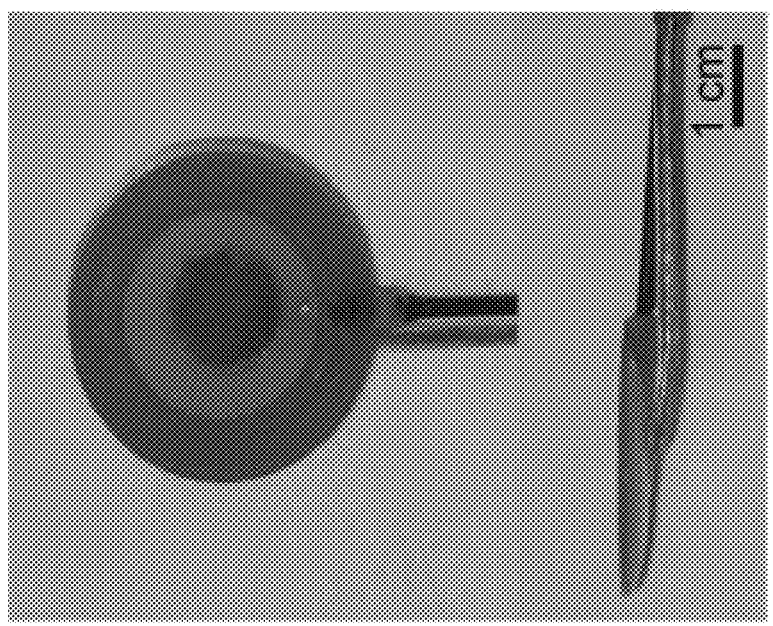
FIG. 41 is a partial view of an implantable iontophoretic device for attachment to canine pancreases according to one embodiment of the present disclosure.
Figure 42:
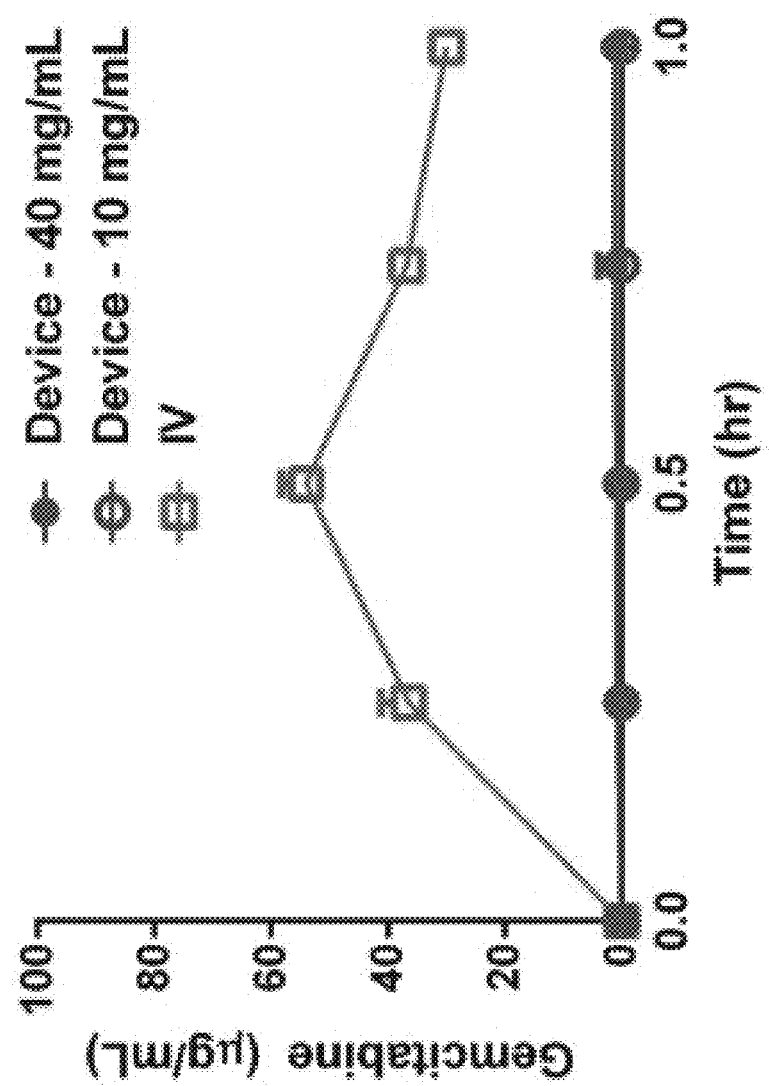
FIG. 42 illustrates experimental results of gemcitabine treatment of a canine pancreas according to one embodiment of the present disclosure.
Figures 43A, 43B:
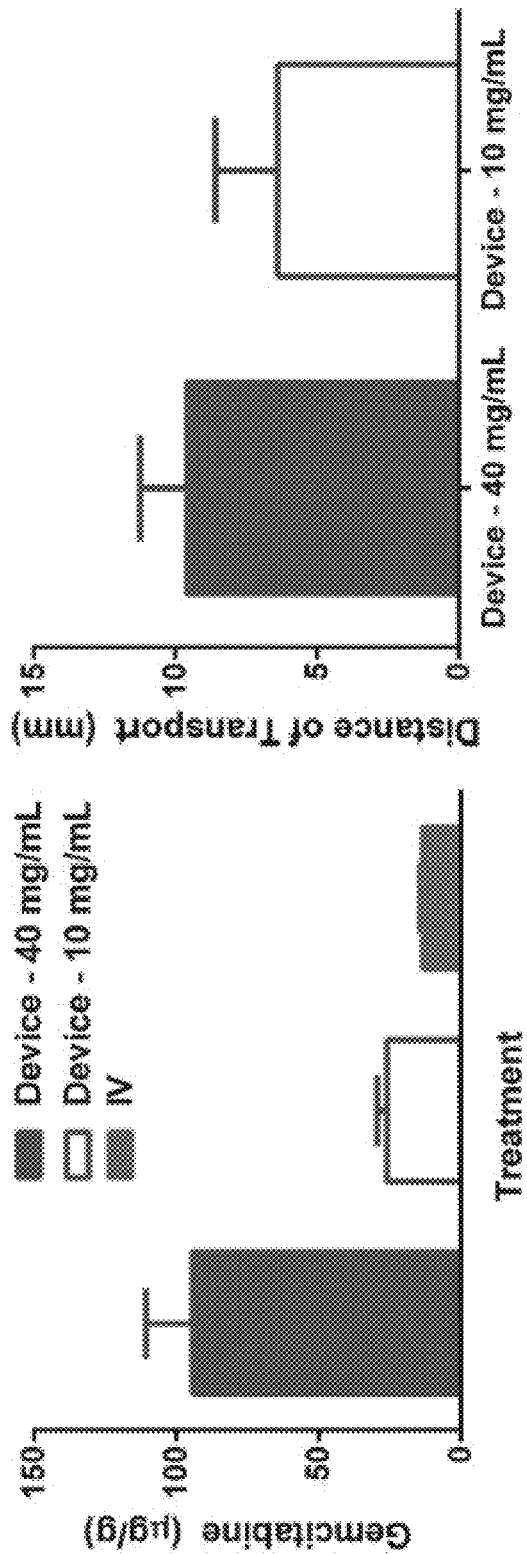
FIG. 43A illustrates experimental results of the amount of gemcitabine in canine pancreases after gemcitabine treatment according to one embodiment of the present disclosure.
FIG. 43B illustrates experimental results of the distance of gemcitabine transport away from a delivery system and into pancreatic tissue in canine models according to one embodiment of the present disclosure.

Since there was no readily available large animal model for pancreatic cancer, a representative non-tumor bearing large animal model (Dogs) for humans was used. A laparotomy was performed and iontophoretic devices (shown in FIG. 41) were sutured directly onto the pancreas. A constant current of 10 mA was applied for 60 minutes using either 40 or 10 mg/mL gemcitabine (n=5, per group). FIG. 42 shows a plasma PK of gemcitabine after the single device treatment in which organs were removed one hour after treatment. For the IV treatment arm (n=4, per group), clinical protocol was followed for gemcitabine administration, which was an infusion of a 1 g/m$^2$ dose for thirty minutes, and the animal was euthanized 60 minutes after the start of the infusion. The plasma was sampled at 15 minute increments before, during, and after therapy. After therapy, the tissues were removed, flash-frozen, and analyzed by UV-HPLC. There was no drug detected in the plasma of the animals at any time when 10 mg/mL gemcitabine was used in the device treatment. The plasma of 2 out of 5 dogs treated with 40 mg/mL gemcitabine delivered by the device had detectable levels of gemcitabine, but the levels of gemcitabine detected were at least 25-fold less than the IV treatment. Gemcitabine was detected in the plasma of all dogs that received IV gemcitabine. There was a 7.1- and 2.0-fold increase in the concentration of gemcitabine in the normal canine pancreas after device delivery using 40 and 10 mg/mL, respectively, compared to IV administration, as shown in FIG. 43A. The distance of gemcitabine transport after device treatment using 40 and 10 mg/mL gemcitabine was 9.6 mm and 6.3 mm away from the electrode respectively, as shown in FIG. 43B.

What is claimed is:

1. A method of delivering a cargo to a target site of body tissue in combination with radiotherapy, the method comprising:
    disposing a source electrode proximate to a target site of body tissue in vivo;
    disposing a counter electrode spaced from the source electrode such that the source electrode and counter electrode are configured to receive tissue of the target site therebetween, the counter electrode in electrical communication with the source electrode and being configured to cooperate with the source electrode to form a localized electric field proximate to the target site;
    disposing a cargo proximate the electric field and capable of being delivered to the target site when exposed to the localized electric field formed between the source electrode and the counter electrode;

securing to the target site a surgically implantable housing defining a reservoir to carry the cargo and capable of interacting with the localized electric field to release the cargo, wherein the localized electric field is configured to deliver at least a portion of a cargo to the target site by applying a voltage potential across the source and counter electrodes to form the localized electric field;

applying the voltage potential across the source and counter electrodes to form the localized electric field, thereby delivering at least a portion of the cargo to the target site;

and applying a radiation to the target site from a radiation source external to the body.

2. The cargo delivery method as recited in claim 1, wherein the method is for the treatment of treatment of cancer selected from pancreatic cancer, breast cancer, lung cancer, esophageal cancer, bladder cancer, colorectal cancer, liver cancer, hepatic metastases, bile duct cancer, renal cancer, cervical cancer, prostate cancer, ovarian cancer, thyroid cancer, uterine cancer, leukemia and combinations thereof.

3. The cargo delivery method as recited in claim 1, wherein the step of delivering at least a portion of the cargo to the target site comprises delivering the cargo to the cranial cavity.

4. The cargo delivery method as recited in claim 3, wherein the step of delivering the cargo to the cranial cavity is for the treatment of brain cancers.

5. The cargo delivery method as recited in claim 1, wherein the step of delivering at least a portion of the cargo to the target site comprises delivering the cargo to the oral cavity.

6. The cargo delivery method as recited in claim 5, wherein the method is for the treatment of treatment of cancer selected from head cancer, neck cancer, thyroid cancers and combinations thereof.

7. The cargo delivery method as recited in claim 1, wherein the step of delivering at least a portion of the cargo to the target site comprises delivering the cargo to the thoracic cavity or mediastinum.

8. The cargo delivery method as recited in claim 7, wherein the method is for the treatment of treatment of cancer selected from thymus cancer, esophageal cancers and combinations thereof.

9. The cargo delivery method as recited in claim 7, wherein the method is for the treatment of heart disease.

10. The cargo delivery method as recited in claim 1, wherein the step of delivering at least a portion of the cargo to the target site comprises delivering the cargo to the pleural cavity.

11. The cargo delivery method as recited in claim 10, wherein the method is for the treatment of lung cancer.

12. The cargo delivery method as recited in claim 10, wherein the method is for the treatment of treatment of cystic fibrosis, pulmonary fibrosis, emphysema, adult respiratory distress syndrome (ARDS), sarcoidosis and combinations thereof.

13. The cargo delivery method as recited in claim 1, wherein the step of delivering at least a portion of the cargo to the target site comprises delivering the cargo to the abdominopelvic cavity or peritoneal cavity.

14. The cargo delivery method as recited in claim 13, wherein the method is for the treatment of pancreatic cancer, liver cancer and metastases, stomach cancer, small bowel cancer, genital warts, renal cancers and metastases, splenic cancer, Hodgkin's disease and combinations thereof.

15. The cargo delivery method as recited in claim 13, wherein the method is for the treatment of inflammatory bowel disease, including Crohn's disease and ulcerative colitis.

16. The cargo delivery method as recited in claim 1, wherein the step of delivering at least a portion of the cargo to the target site comprises delivering the cargo to the pelvic cavity.

17. The cargo delivery method as recited in claim 16, wherein the method is for the treatment of testicular cancer, prostate cancer, ovarian cancer, fallopian tube cancer, cervical cancer, endometrial cancer, uterine cancer, Kaposi's sarcoma, colorectal cancers, urinary bladder cancer and combinations thereof.

18. A system for treating a target site of body tissue, the system comprising:

a source electrode proximate to a target site of body tissue in vivo;

a counter electrode in electrical communication with the source electrode, the counter electrode being configured to cooperate with the source electrode to form a localized electric field proximate to the target site;

a cargo capable of being delivered through the tissue of the target site when exposed to the localized electric field formed between the source electrode and the counter electrode;

a surgically implantable housing adapted to be secured to the target site, wherein the housing defines a reservoir to carry the cargo and is capable of interacting with the localized electric field to release the cargo;

means for securing the housing to the tissue of the target site, wherein the counter electrode is spaced from the housing and the source electrode, wherein the localized electric field is configured to deliver at least a portion of a cargo to the target site by applying a voltage potential across the source and counter electrodes to form the localized electric field; and a radiation source external to the body and configured to apply a radiation to the target site.

19. The treatment system as recited in claim 18, wherein the housing comprises the source electrode.

20. The treatment system as recited in claim 18, wherein the housing comprises the counter electrode.

21. The treatment system as recited in claim 18, wherein the source electrode is external to the body.

22. The treatment system as recited in claim 18, wherein the counter electrode is external to the body.

23. The treatment system as recited in claim 18, wherein the housing comprises a polyurethane shell.

24. The treatment system as recited in claim 18, wherein the housing comprises a polydimethylsiloxane shell.

25. The treatment system as recited in claim 18, further comprising a power source connected to the source electrode and the counter electrode for delivering a current and generating the localized electric field.

26. The treatment system as recited in claim 25, wherein the current is DC in a range of about 2-20 mA.

27. The treatment system as recited in claim 25, wherein the power source comprises a function generator for delivering pulsed waveforms.

28. The treatment system as recited in claim 27, wherein the waveforms are selected from triangular, sawtooth, square, multi-step and combinations thereof.

29. The treatment system as recited in claim 28, wherein the source electrode is formed from material selected from wire, foil, mesh, pellets, disc, stent, clamp, prongs, clips, needles, hollow tube or combinations thereof.

\* \* \* \* \*